(12) United States Patent
Locke

(10) Patent No.: US 10,667,735 B2
(45) Date of Patent: Jun. 2, 2020

(54) APPARATUSES AND METHODS FOR INLINE COLLECTION OF A FLUID SPECIMEN

(71) Applicant: KCI Licensing, Inc., San Antonio, TX (US)

(72) Inventor: Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 1138 days.

(21) Appl. No.: 14/488,498

(22) Filed: Sep. 17, 2014

(65) Prior Publication Data
US 2015/0088035 A1   Mar. 26, 2015

Related U.S. Application Data

(60) Provisional application No. 61/882,386, filed on Sep. 25, 2013.

(51) Int. Cl.
*A61B 5/15*   (2006.01)
*A61B 10/00*   (2006.01)
*A61M 39/22*   (2006.01)

(52) U.S. Cl.
CPC .. *A61B 5/150267* (2013.01); *A61B 5/150946* (2013.01); *A61B 5/150969* (2013.01); *A61B 10/0045* (2013.01); *A61M 39/223* (2013.01)

(58) Field of Classification Search
CPC ... A61M 25/02; A61M 1/0088; Y10S 128/26; A61F 2013/00519; A61F 13/023; F16L 41/021; F16L 41/023
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |

(Continued)

FOREIGN PATENT DOCUMENTS

| | | |
|---|---|---|
| AU | 550575 A1 | 3/1986 |
| AU | 745271 | 4/1999 |

(Continued)

OTHER PUBLICATIONS

International Search Report and Written Opinion for corresponding application PCT/US2014/056121, dated Feb. 24, 2015.

(Continued)

*Primary Examiner* — Patrick Fernandes

(57) ABSTRACT

An apparatus, system, and method for sampling a fluid from a tissue site is described. The system includes a collection fitting, a reduced-pressure source, and a specimen container. The collection fitting includes a tee-fitting having a first arm having a first union, a second arm having a second union, and a third arm. At least one lumen extends through the tee-fitting from the first arm to the third arm, and at least one lumen extends through the tee-fitting from the second arm to the third arm. A container union is coupled to the third arm. The reduced-pressure source is configured to be fluidly coupled to the first union, and the specimen container is configured to be coupled to the container union.

30 Claims, 26 Drawing Sheets

(56) References Cited

U.S. PATENT DOCUMENTS

| | | | |
|---|---|---|---|
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,807,444 A * | 4/1974 | Fortune | F16K 15/144 137/512.1 |
| 3,826,254 A | 7/1974 | Mellor | |
| 3,965,910 A * | 6/1976 | Fischer | A61M 39/02 604/249 |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,423,741 A | 1/1984 | Levy | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,691,737 A | 9/1987 | Sebo | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,894,057 A * | 1/1990 | Howes | A61B 5/02152 604/43 |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,363,860 A * | 11/1994 | Nakao | A61B 10/0045 600/573 |
| 5,417,673 A * | 5/1995 | Gordon | A61M 39/045 604/537 |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,971,021 A | 10/1999 | Graham | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,375,625 B1 | 4/2002 | French et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| RE39,334 E * | 10/2006 | Lynn | A61M 39/02 604/533 |
| 9,278,742 B2 | 3/2016 | Young | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2002/0195155 A1 * | 12/2002 | Debaisieux | B21C 37/14 138/116 |
| 2003/0181850 A1 * | 9/2003 | Diamond | A61M 39/223 604/30 |
| 2006/0079852 A1 | 4/2006 | Bubb et al. | |
| 2007/0149896 A1 | 6/2007 | Yang | |
| 2010/0174210 A1 | 7/2010 | Han et al. | |
| 2010/0324450 A1 | 12/2010 | Leach et al. | |
| 2011/0015591 A1 | 1/2011 | Hanson et al. | |
| 2012/0065482 A1 * | 3/2012 | Robinson | A61B 5/14532 600/309 |
| 2012/0095369 A1 * | 4/2012 | Teixeira | A61B 10/0051 600/582 |
| 2012/0316415 A1 | 12/2012 | Gilbert | |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0355302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| GB | 2458572 A | 9/2009 |
| JP | 4129536 | 4/1992 |

(56) References Cited

FOREIGN PATENT DOCUMENTS

| | | |
|---|---|---|
| SG | 71559 | 3/1999 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 0028889 A1 | 5/2000 |

OTHER PUBLICATIONS

International Search Report and Written Opinion for corresponding application PCT/US2014/056148, dated Jan. 21, 2015.
International Search Report and Written Opinion for corresponding application PCT/US2014/056136, dated Mar. 17, 2015.
Partial International Search Report for corresponding PCT/US2014/056121 dated Dec. 19, 2014.
N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

\* cited by examiner

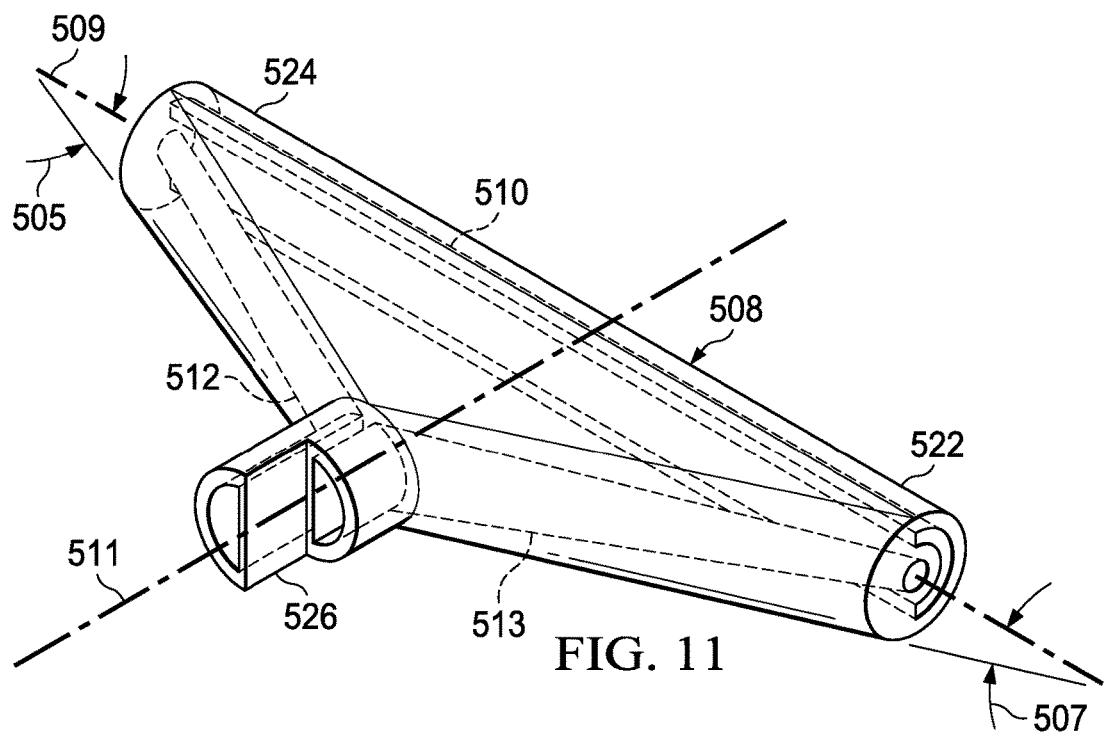
FIG. 11
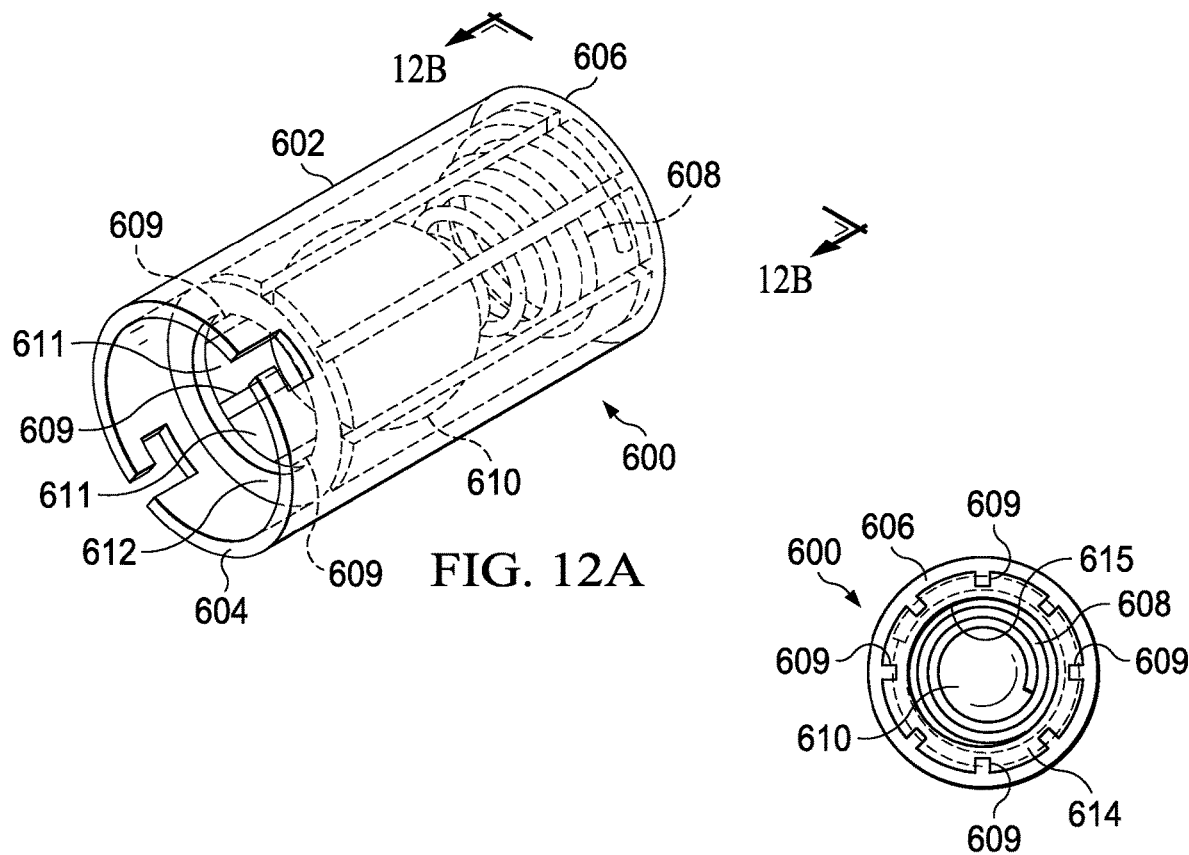
FIG. 12A
FIG. 12B

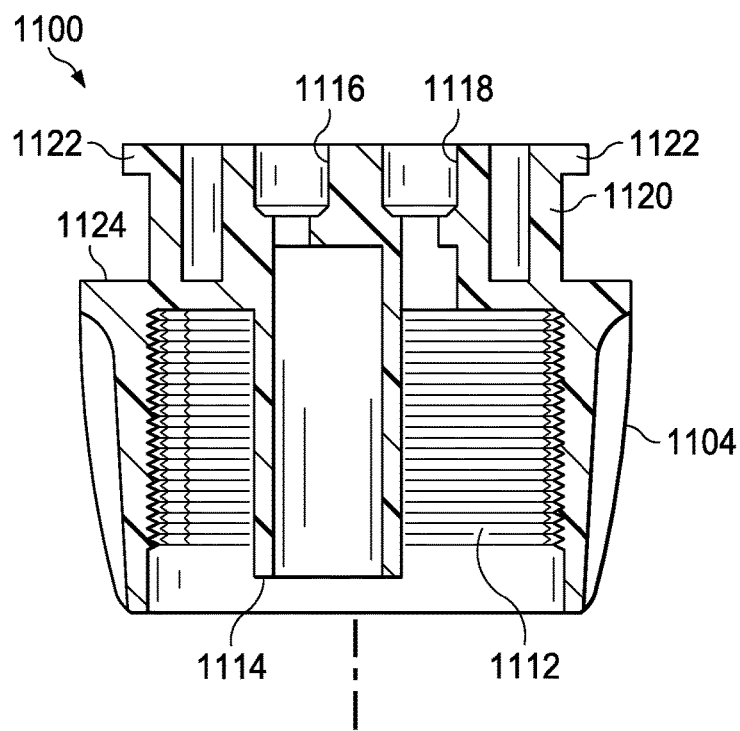
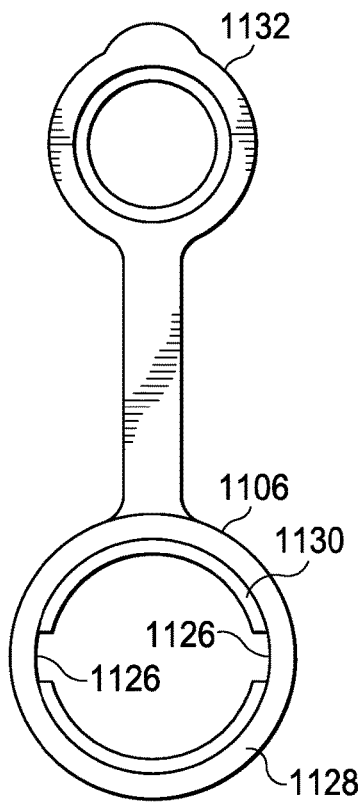
FIG. 29A
FIG. 29B

APPARATUSES AND METHODS FOR INLINE COLLECTION OF A FLUID SPECIMEN

RELATED APPLICATION

The present invention claims the benefit, under 35 USC § 119(e), of the filing of U.S. Provisional Patent Application Ser. No. 61/882,386, entitled "APPARATUSES & METHODS FOR INLINE COLLECTION OF A FLUID SPECIMEN," filed Sep. 25, 2013, which is incorporated herein by reference for all purposes.

TECHNICAL FIELD

The apparatuses and methods described herein relate generally to tissue treatment systems. More particularly, but without limitation, the apparatuses and methods relate to inline collection of a fluid specimen while providing reduced-pressure therapy.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds with reduced pressure may be commonly referred to as "negative-pressure therapy," but is also known by other names, including "negative-pressure wound therapy," "reduced-pressure wound therapy," "vacuum therapy," and "vacuum-assisted closure," for example. Negative-pressure therapy may provide a number of benefits, including migration of epithelial and subcutaneous tissues, improved blood flow, and microdeformation of tissue at a wound site. Together, these benefits can increase development of granulation tissue and reduce healing times.

While the clinical benefits of reduced-pressure therapy are widely known, the cost and complexity of reduced-pressure therapy can be a limiting factor in its application, and the development and operation of reduced-pressure therapy systems, components, and processes continues to present significant challenges to manufacturers, healthcare providers, and patients.

BRIEF SUMMARY

In one example embodiment, a collection fitting for sampling a fluid from a tissue site is described. The collection fitting may include a tee-fitting having a first arm, a second arm, and a third arm. At least one lumen may extend through the tee-fitting from the first arm to the third arm, and at least one lumen may extend through the tee-fitting from the second arm to the third arm. A container union may be coupled to the third arm.

In another example embodiment, a collection fitting for sampling a fluid from a tissue site is described. The collection fitting may include a connector having a first union configured to be fluidly coupled to the tissue site, a second union configured to be fluidly coupled to a reduced-pressure source, and a channel forming a fluid path from the first union to the second union. A container union may be formed in an exterior of the connector proximate to the channel and in fluid communication with the channel. A tube may be disposed in the channel, the tube having at least one lumen and an opening into the at least one lumen through a sidewall of the tube. The first union may be coupled to a first end of the tube and the second union may be coupled to a second end of the tube. The container union may include a boss having a passage and extending from the container union through the opening into the at least one lumen of the tube. A specimen container may be coupled to the container union and configured to be fluidly coupled to the at least one lumen through the passage of the boss.

In yet another example embodiment, a system for sampling a fluid from a tissue site is described. The system may include a collection fitting. The collection fitting may include a tee-fitting having a first arm having a first union, a second arm having a second union, and a third arm. At least one lumen may extend through the tee-fitting from the first arm to the third arm, and at least one lumen may extend through the tee-fitting from the second arm to the third arm. A container union may be coupled to the third arm. A reduced-pressure source may be configured to be fluidly coupled to the first union, and a specimen container may be configured to be coupled to the container union.

In still another example embodiment, a system for sampling a fluid from a tissue site is described. The system may include a collection fitting, a reduced-pressure source, and a specimen container. The collection fitting may include a connector having a first union configured to be fluidly coupled to the tissue site, a second union configured to be fluidly coupled to a reduced-pressure source, and a channel forming a fluid path from the first union to the second union. A container union may be formed in an exterior of the connector proximate to the channel and in fluid communication with the channel. A tube may be disposed in the channel, the tube having at least one lumen and an opening into the at least one lumen through a sidewall of the tube. The first union may be coupled to a first end of the tube and the second union is coupled to a second end of the tube. The container union may include a boss having a passage and extending from the container union through the opening into the at least one lumen of the tube. The specimen container may be coupled to the container union and be configured to be fluidly coupled to the at least one lumen through the passage of the boss. The reduced-pressure source may be configured to be fluidly coupled to the first union.

It another example embodiment, a method for sampling fluid from a tissue site is described. The method fluidly may couple a collection fitting inline between a tissue site and a storage container. The method may couple a specimen container to the collection fitting to receive fluids from the tissue site, and the method may uncouple the specimen container from the collection fitting.

In still another example embodiment, an apparatus for sampling a fluid from a tissue site is described. The apparatus may include a collection fitting having a first union configured to be fluidly coupled to the tissue site, a second union configured to be fluidly coupled to a reduced-pressure source, and a container union configured to be fluidly coupled to a specimen container. A fluid path from the first union to the second union may be in fluid communication with the container union.

In yet another example embodiment, an apparatus for sampling fluid from a tissue site is described. The apparatus may include a petcock fluidly coupled inline between a dressing and a storage container. In some embodiments, the apparatus may include a stopcock fluidly coupled inline between a dressing and a storage container.

Other objects, features, and advantages of the embodiments described herein will become apparent with reference to the drawings and detailed description that follow.

BRIEF DESCRIPTION OF THE DRAWINGS

FIG. 11 is a perspective view of an example embodiment of another tee fitting that may be used in place of the tee-fitting of FIG. 10;

FIG. 12A is a perspective view of an example embodiment of a sampling valve that may be used with a collection fitting such as the tee fitting of FIG. 10;

FIG. 12B is an end view of the illustrative sampling valve of FIG. 12A;

FIG. 29A is an exploded cross-sectional view of an example embodiment of a specimen container that may be used with a collection fitting such as the collection fitting of FIG. 23;

FIG. 29B is a top view of an example embodiment of a dust cap that may be used with a specimen container such as the specimen container of FIG. 29A;

DESCRIPTION OF EXAMPLE EMBODIMENTS

New and useful systems and methods for sampling fluid in a reduced-pressure therapy environment are set forth in the appended claims. Objectives, advantages, and a preferred mode of making and using the systems and methods may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. The claimed subject matter may also encompass alternative embodiments not specifically described in detail. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
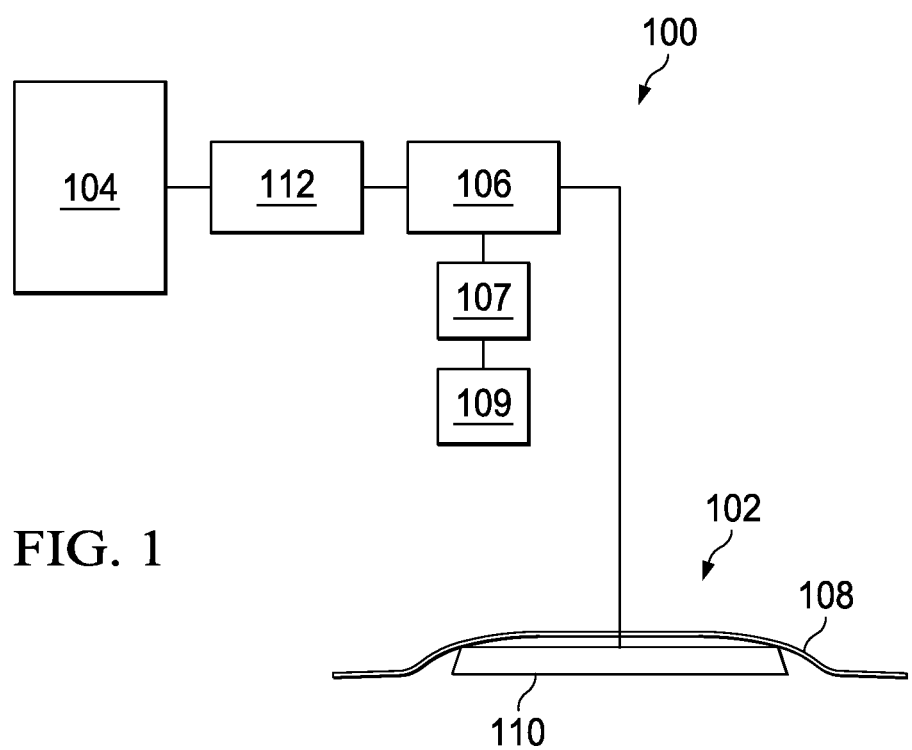
FIG. 1 is a functional block diagram of an example embodiment of a reduced-pressure therapy system that can sample fluid in accordance with this specification.

FIG. 1 is a simplified functional block diagram of an example embodiment of a reduced-pressure therapy system 100 that can sample fluid in accordance with this specification. As shown in some embodiments, the reduced-pressure therapy system 100 may include a dressing 102 fluidly coupled to a reduced-pressure source 104. An inline sampling apparatus, such as a collection fitting 106, may also be fluidly coupled to the dressing 102 and the reduced-pressure source 104. The dressing 102 generally includes a drape, such as a drape 108, and a tissue interface, such as a manifold 110. The reduced-pressure therapy system 100 may also include a fluid container, such as a storage container 112, coupled to the dressing 102 and the reduced-pressure source 104. The collection fitting 106 may include a sampling valve 107 fluidly coupled to the collection fitting 106 and a specimen container, such as a specimen container 109 adapted to be fluidly coupled to the sampling valve 107.

In general, components of the reduced-pressure therapy system 100 may be coupled directly or indirectly. For example, the reduced-pressure source 104 may be directly coupled to the collection fitting 106 and indirectly coupled to the dressing 102 through the collection fitting 106. Components may be fluidly coupled to each other to provide a path for transferring fluids (i.e., liquid and/or gas) between the components. In some embodiments, components may be fluidly coupled with a tube, for example. A "tube," as used herein, broadly refers to a tube, pipe, hose, conduit, or other structure with one or more lumina adapted to convey fluids between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical union (such as a chemical bond) in some contexts.

In operation, a tissue interface, such as the manifold 110, may be placed within, over, on, against, or otherwise adjacent to a tissue site. For example, the manifold 110 may be placed against a tissue site, and the drape 108 may be placed over the manifold 110 and sealed to tissue proximate to the tissue site. Tissue proximate to a tissue site is often undamaged epidermis peripheral to the tissue site. Thus, the dressing 102 can provide a sealed therapeutic environment proximate to a tissue site, substantially isolated from the external environment, and the reduced-pressure source 104 can reduce the pressure in the sealed therapeutic environment. Reduced pressure applied uniformly through the tissue interface in the sealed therapeutic environment can induce macrostrain and microstrain in a tissue site, as well as remove exudates and other fluids from a tissue site, which can be collected in the storage container 112 and disposed of properly.

Exudates may refer to fluid that filters from the circulatory system into lesions or areas of inflammation. Exudates may include water and dissolved solutes. Dissolved solutes may include blood, plasma proteins, white blood cells, platelets, and red blood cells. In some embodiments, exudates may include serum, fibrin, and white blood cells. In other embodiments, exudates may include pus having a thin protein-rich fluid and dead leukocytes.

The fluid mechanics of using a reduced-pressure source to reduce pressure in another component or location, such as within a sealed therapeutic environment, can be mathematically complex. However, the basic principles of fluid mechanics applicable to reduced-pressure therapy are generally well-known to those skilled in the art, and the process of reducing pressure may be described illustratively herein as "delivering," "distributing," or "generating" reduced pressure, for example.

In general, exudates and other fluids flow toward lower pressure along a fluid path. Thus, in the context of reduced-pressure therapy, the term "downstream" typically implies something in a fluid path relatively closer to a reduced-pressure source, and conversely, the term "upstream" implies something relatively further away from a reduced-pressure source. Similarly, it may be convenient to describe certain features in terms of fluid "inlet" or "outlet" in such a frame of reference. This orientation is generally presumed for purposes of describing various features and components of reduced-pressure therapy systems herein. However, the fluid path may also be reversed in some applications (such as by substituting a positive-pressure source for a reduced-pressure source) and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, reduced pressure may be used in certain tissue areas to grow additional tissue that may be harvested and transplanted to another tissue location.

"Reduced pressure" generally refers to a pressure less than a local ambient pressure, such as the ambient pressure in a local environment external to a sealed therapeutic environment provided by the dressing 102. In many cases, the local ambient pressure may also be the atmospheric pressure at which a patient is located. Alternatively, the pressure may be less than a hydrostatic pressure associated with tissue at the tissue site. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

A reduced-pressure source, such as the reduced-pressure source 104, may be a reservoir of air at a reduced pressure, or may be a manual or electrically-powered device that can reduce the pressure in a sealed volume, such as a vacuum pump, a suction pump, a wall suction port available at many healthcare facilities, or a micro-pump, for example. The reduced-pressure source may be housed within or used in conjunction with other components, such as sensors, processing units, alarm indicators, memory, databases, software, display devices, or user interfaces that further facilitate reduced-pressure therapy. While the amount and nature of reduced pressure applied to a tissue site may vary according to therapeutic requirements, the pressure typically ranges between −5 mm Hg (−667 Pa) and −500 mm Hg (−66.7 kPa). Common therapeutic ranges are between −75 mm Hg (−9.9 kPa) and −300 mm Hg (−39.9 kPa).

A tissue interface, such as the manifold 110, can be generally adapted to contact a tissue site. A tissue interface may be partially or fully in contact with a tissue site. If a tissue site is a wound, for example, a tissue interface may partially or completely fill the wound, or may be placed over the wound. A tissue interface may take many forms, and may have many sizes, shapes, or thicknesses depending on a variety of factors, such as the type of treatment being implemented or the nature and size of a tissue site. For example, the size and shape of a tissue interface may be adapted to the contours of deep and irregular shaped tissue sites.

Generally, a manifold, such as the manifold 110, for example, is a substance or structure adapted to distribute or remove fluids from a tissue site. A manifold may include flow channels or pathways that distribute fluids provided to and removed from a tissue site around the manifold. In one illustrative embodiment, the flow channels or pathways may be interconnected to improve distribution of fluids provided to or removed from a tissue site. For example, open-cell foam, porous tissue collections, and other porous material such as gauze or felted mat generally include structural elements arranged to form flow channels. Liquids, gels, and other foams may also include or be cured to include flow channels.

In one illustrative embodiment, the manifold 110 may be a porous foam pad having interconnected cells adapted to distribute reduced pressure across a tissue site. The foam may be either hydrophobic or hydrophilic. In one non-limiting example, the manifold 110 can be an open-cell, reticulated polyurethane foam, such as GranuFoam® dressing available from Kinetic Concepts, Inc. of San Antonio, Tex.

In an example in which the manifold 110 may be made from a hydrophilic material, the manifold 110 may also wick fluid away from a tissue site, while continuing to distribute reduced pressure to the tissue site. The wicking properties of the manifold 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

A tissue interface may further promote granulation at a tissue site if pressure within the sealed therapeutic environment is reduced. For example, any or all of the surfaces of the manifold 110 may have an uneven, coarse, or jagged profile that can induce microstrains and stresses at a tissue site if reduced pressure is applied through the manifold 110.

In one embodiment, a tissue interface may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface may further serve as a scaffold for new cell-growth, or a scaffold material may be used in conjunction with a tissue interface to promote cell-growth. A scaffold is generally a biodegradable or biocompatible substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The drape 108 is an example of a sealing member. A sealing member may be constructed from a material that can provide a fluid seal between two components or two environments, such as between a therapeutic environment and a local external environment. A sealing member may be, for example, an impermeable or semi-permeable, elastomeric film that can provide a seal adequate to maintain a reduced pressure at a tissue site for a given reduced-pressure source. For semi-permeable materials, the permeability generally should be low enough that a desired reduced pressure may be maintained. An attachment device may be used to attach a sealing member to an attachment surface, such as undamaged epidermis, a gasket, or another sealing member. An attachment device may take many forms. For example, an attachment device may be a medically-acceptable, pressure-sensitive adhesive that extends about a periphery, a portion, or an entire sealing member. Other example embodiments of an attachment device may include a double-sided tape, paste, hydrocolloid, hydrogel, silicone gel, organogel, or an acrylic adhesive.

A "container," such as the storage container 112 or the specimen container 109 in FIG. 1, broadly includes a canister, pouch, bottle, vial, or other fluid collection apparatus. The storage container 112 for example, can be used to manage exudates and other fluids withdrawn from a tissue site. In some embodiments, the storage container 112 may include substances to manage fluid in the storage container 112, such as isolyzers or absorbents, for example. In many environments, a rigid container may be preferred or required for collecting, storing, and disposing of fluids. In other environments, fluids may be properly disposed of without rigid container storage, and a re-usable container could reduce waste and costs associated with reduced-pressure therapy. In some embodiments, the specimen container 109 may be similar to the storage container 112. Generally, the specimen container 109 may receive and store a sample of fluids from the tissue site for testing or experimentation. Generally, the specimen container 109 may be free of fluid management substances, such as isolyzers or absorbents, for example. In some embodiments, the specimen container 109 may be smaller than the storage container 112 and be adapted to receive smaller amounts of fluid.

The reduced-pressure therapy system 100 may be used to treat tissue sites that are in various stages of healing, and exudate from a tissue site can be a useful diagnostic aid. Thus, it may be useful to collect exudate from a tissue site during the application of reduced-pressure therapy. For example, a sample of exudate from a tissue site may be tested to determine if bacteria is growing at the tissue site, the type of bacteria growing at the tissue site, and the amount of bacteria growing at the tissue site. In another example, exudate from a tissue site may be tested to determine if the tissue site is becoming necrotic or otherwise failing to respond in a desired manner.

Currently, exudate may be collected from a tissue site in a limited number of ways. For example, fluids may be sampled directly from a tissue site by stopping reduced-pressure therapy, removing the dressing from the tissue site, and attempting to retrieve a sample directly from the tissue site. This collection procedure may be unsuitable or undesirable for several reasons. For example, the process requires that reduced-pressure therapy must be stopped for an extended period of time while fluid is collected from the tissue site. Extended periods without reduced-pressure therapy may be detrimental to the healing of the tissue site and increase the total time required to heal. The process also risks contamination of the tissue site as the dressing must be removed from the tissue site, exposing the tissue site to the ambient environment. The process may also cause pain to the patient. For example, the adhesives of the dressing may cause pain to the patient if the dressing is removed. Sampling of the fluids from the tissue site by removing the dressing may also bring the tissue site into contact with instruments that may aggravate the damaged tissue.

Another way to obtain a sample of exudate from a tissue site is to take a sample from a container downstream from a dressing, such as from the storage container 112. To obtain a sample of fluids from a container downstream from a dressing, such as the storage container 112, the reduced-pressure therapy is typically stopped so that the container may be uncoupled from the reduced-pressure therapy system. A sample of the fluids from the tissue site can then be taken from the container for testing. The container may then be recoupled to the reduced-pressure therapy system, and reduced-pressure therapy restarted. Much like sampling fluids directly from the tissue site, obtaining fluids from the tissue site using a container such as the storage container 112 may cause the tissue site to do without reduced-pressure therapy for an extended time and increase the total healing time required.

A container such as the storage container 112 may also include an absorbent, isolyzer, or other substance configured to reduce the moisture content of the fluids from the tissue site that are collected in the container. The moisture-reducing substances may decrease the volume of the fluids in the container by decreasing the moisture content of the fluids in the container. The moisture-reducing substances may contaminate the fluids from the tissue site that are collected in the container. If the fluids from the tissue site in the storage container 112 become contaminated by the moisture-reducing substances, subsequent testing of the fluids sampled from the container may provide results having significant errors. The errors may make the testing process unreliable and hinder an accurate diagnosis.

The storage container 112 may also be used to collect fluids from the tissue site for an extended period of time, which can present another problem to testing fluids from the storage container 112. For example, the storage container 112 may collect fluids from the tissue site for several hours or several days depending on the amount of fluid being received from the tissue site. A sample taken from the storage container 112 after the storage container 112 has been used to collect fluids from the tissue site for a long duration may not represent the current condition of the tissue site. Again, obtaining a sample from the storage container 112 may introduce significant errors into any test results from the sample. The errors may make the testing process unreliable and hinder a proper diagnosis.

As disclosed herein, the reduced-pressure therapy system 100 can overcome these shortcomings and others by providing a collection fitting, such as the collection fitting 106, that enables collection of exudate specimens from a tissue site without interrupting reduced-pressure therapy. The collection fitting 106 may be used to sample exudate from the tissue site that is uncontaminated by other environments. The collection fitting 106 may also be used to sample exudate from a tissue site at a discrete moment in time. In an illustrative embodiment, the collection fitting 106 may include a stopcock or petcock fluidly coupled inline between the dressing 102 and the storage container 112. In some embodiments, the collection fitting 106 may have three couplings, such as three unions that allow quick and convenient disconnection to other components. For example, the collection fitting 106 may include a first union configured to permit fluid coupling with a dressing, a second union that may permit fluid coupling with the storage container 112, and a third union, which may also be referred to as a container union, having a valve, such as the sampling valve 107. Fluid communication may occur through the collection fitting 106 between the storage container 112 and the dressing 102. The sampling valve 107 may remain closed during normal operation of the reduced-pressure therapy system 100.

If an exudate specimen is desired, the specimen container 109 may be coupled to the third union, and the sampling valve 107 may be opened so that fluid communication may occur through the third union. While the specimen container 109 is coupled to the third union and the sampling valve 107 is opened, reduced-pressure therapy may continue. The collection fitting 106 preferably provides at least one fluid path between the dressing 102 and the storage container 112 in both the open and closed position. In some embodiments, the fluid path between the reduced-pressure source 104 and the dressing 102 may pass through the specimen container 109 if the sampling valve 107 is open. As fluids from the tissue site are collected, the fluids may flow through the collection fitting 106 and the specimen container 109 coupled to the collection fitting 106, depositing an exudate specimen in the specimen container 109. If a desired amount of exudate has been collected in the specimen container 109, the sampling valve 107 may be closed, and the specimen container 109 can be uncoupled from the third union. The exudate specimen collected in the specimen container 109 may then be tested using suitable diagnostic procedures.

Connector

Figure 2:
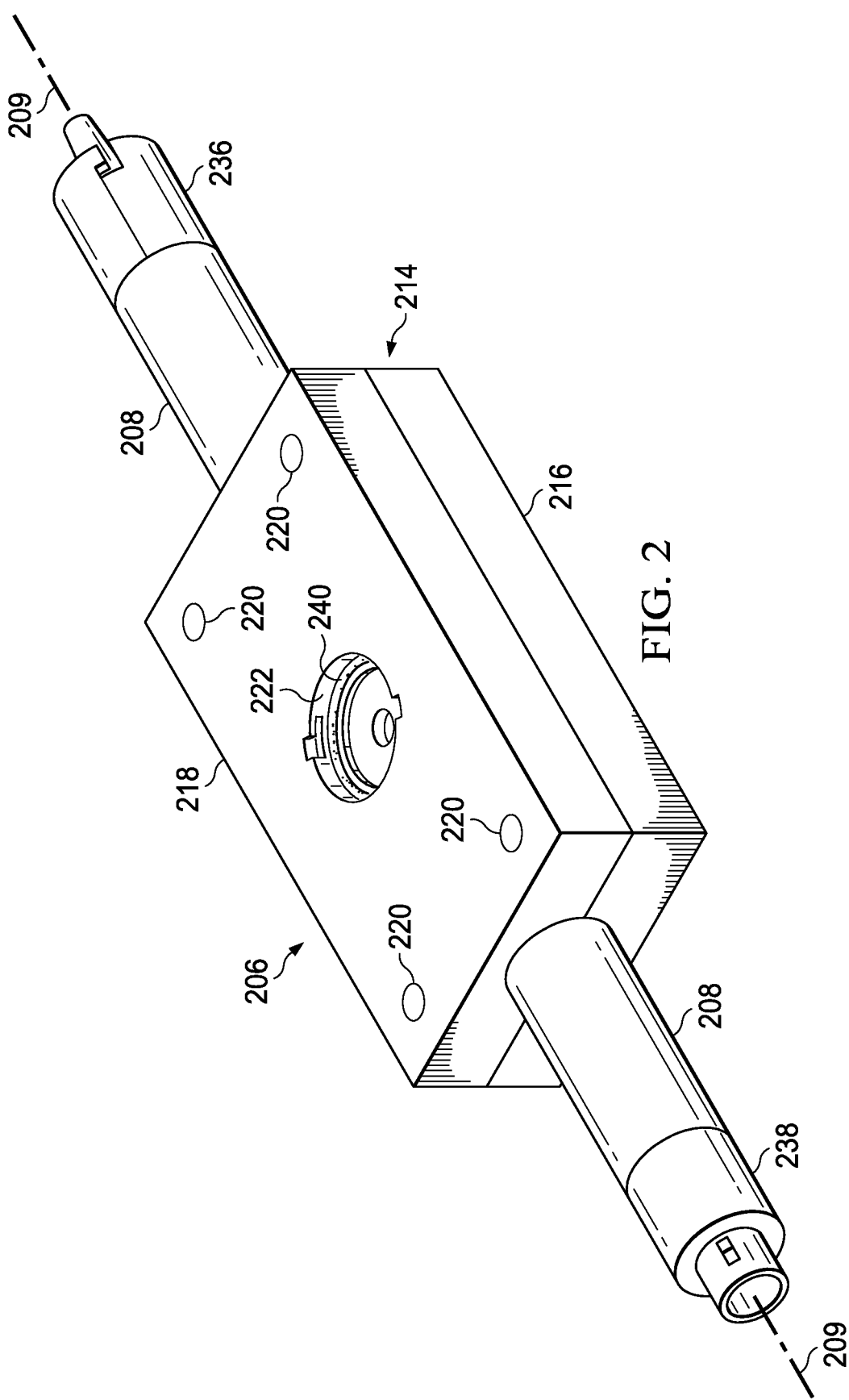
FIG. 2 is a perspective view illustrating additional details of an example embodiment of a collection fitting that may be associated with some embodiments of the reduced-pressure therapy system of FIG. 1.

FIG. 2 is a perspective view of a collection fitting 206 that may be used with a reduced-pressure therapy system, such as the reduced-pressure therapy system 100 of FIG. 1, for example. The collection fitting 206 may be an illustrative embodiment of the collection fitting 106 in FIG. 1. The collection fitting 206 may include a tube 208 and a connector 214. The collection fitting 206 may further include a first union 236 and a second union 238.

The connector 214 may include a retainer plate, such as a first plate 216, and an access plate, such as a second plate 218. In some embodiments, the first plate 216 and the second plate 218 may be rectangular plates and may be coextensive, having substantially equivalent exterior dimensions. In other embodiments, the first plate 216 and the second plate 218 may not be coextensive. The second plate 218 may also include one or more bores 220 that may extend through the second plate 218. In some embodiments, a container union 222 may be disposed in the second plate 218. In some embodiments, the container union 222 may be disposed in a center of the second plate 218. As shown in FIG. 2, the first plate 216 and the second plate 218 may be placed adjacent to each other to enclose a portion of the tube 208.

Figure 3:
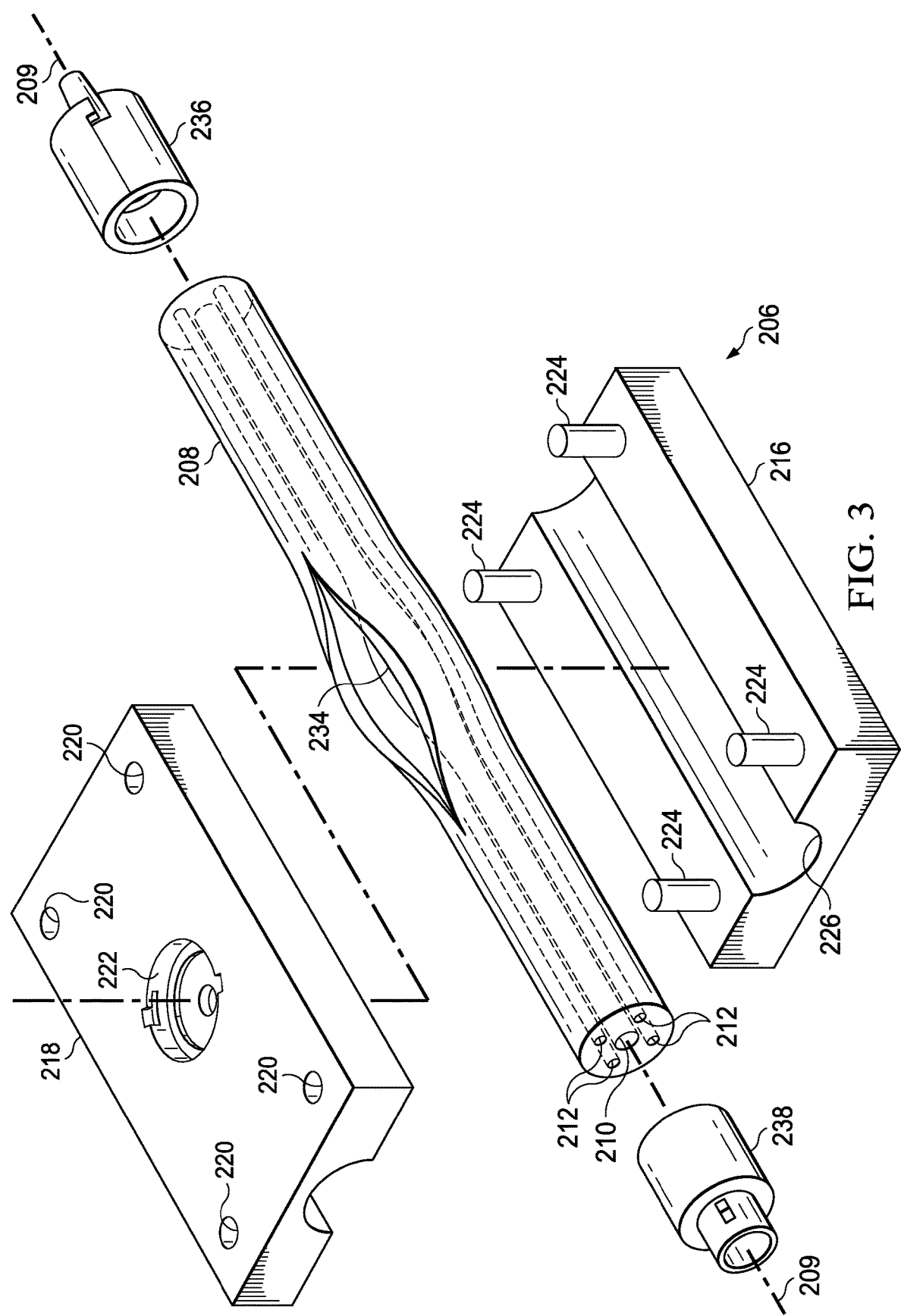
FIG. 3 is an exploded partial view illustrating additional details of the collection fitting of FIG. 2.

FIG. 3 is an exploded view of the collection fitting 206 illustrating additional details that may be associated with some embodiments. The tube 208 may be a multi-lumen conduit having a central lumen, such as a lumen 210, for example, and one or more peripheral lumens, such as lumens 212, for example. The lumen 210 may extend from the first end of the tube 208 to the second end of the tube 208. In some embodiments, the lumen 210 may be disposed proximate to a center of the tube 208. In some embodiments, the lumen 210 may be coaxial with an axis 209 of the tube 208. In other embodiments, the lumen 210 may be offset from the axis 209 of the tube 208. In some embodiments, the lumen 210 may provide a fluid path for reduced pressure between the dressing and the fluid collection apparatus.

The lumens 212 may also extend from the first end of the tube 208 to the second end of the tube 208. In some embodiments, the lumens 212 may be circumferentially spaced around the axis 209 of the tube 208. In other embodiments, the lumens 212 may not be circumferentially spaced around the axis 209 of the tube 208. For example, the lumens 212 may be disposed in one portion of the tube 208. Although four lumens 212 are shown in FIG. 3, other embodiments of the tube 208 may have more or fewer lumens 212. In some embodiments, each lumen 212 may have a major dimension, such as a diameter, less than a major dimension of the lumen 210.

As shown in FIG. 3, the first union 236 may be coupled to a first end of the tube 208, and the second union 238 may be coupled to a second end of the tube 208 opposite the first end. In some embodiments, both the second union 238 and the first union 236 may be multi-lumen connectors. In these embodiments, the second union 238 and the first union 236 may include one or more lumens configured to be coupled to the lumen 210 and the lumens 212 to provide an independent path of fluid communication for the lumen 210 and the lumens 212 through the second union 238 and the first union 236. In some embodiments, the second union 238 and the first union 236 may provide separate paths of fluid communication for each lumen 212. The second union 238 and the first union 236 may be configured to be coupled to a additional unions, respectively, to provide a fluid coupling to another device, such as a tube, a reduced-pressure source, a container, or a dressing, for example. In some embodiments, the first union 236 and the second union 238 may be male unions configured to be inserted into a female union. In some embodiments, the first union 236 and the second union 238 may be female unions configured to receive a male union. In other embodiments, the first union 236 and the second union 238 may be either a male union or a female union and configured to receive either a female union or a male union, respectively.

As shown in some embodiments of FIG. 3, the collection fitting 206 is disassembled so that a portion of the tube 208 enclosed by the connector 214 may be viewed. The tube 208 may include an opening 234 that may extend through a wall of the tube 208. In some embodiments, the opening 234 extends from an exterior of the tube 208 through the wall of the tube 208 and into the lumen 210. In some embodiments, the opening 234 may be fluidly isolated from the lumens 212. The opening 234 may be formed by cutting a slit into the tube 208. In other embodiments, the tube 208 may be manufactured to include the opening 234. The opening 234 may provide a fluid path into the lumen 210 through the wall of the tube 208.

The first plate 216 may include a channel 226 configured to received a portion of a tube, such as the tube 208. In some embodiments, for example, the channel 226 may have a semicircular profile and may extend a length of the first plate 216. In other embodiments, the channel 226 may have other profiles, such as square, or triangular, for example, to engage tubing of compatible geometry. As shown in some embodiments of FIG. 3, the channel 226 may be disposed along a major or minor axis of the first plate 216. A dimension, such as a diameter, for example, of the channel 226 may be substantially equal to an outer dimension of the tube 208 so that at least a portion of the tube 208 may be disposed in the channel 226.

The first plate 216 may also include one or more rods 224. The rods 224 may be cylindrical members projecting from an upper surface of the first plate 216 proximate to the channel 226. In other embodiments, the rods are not cylindrical. In other embodiments, the rods 224 may be distributed in other locations of the first plate 216. The rods 224 may have a height substantially equal to a width of the second plate 218. In some embodiments, the rods 224 may be distributed around a peripheral edge of the first plate 216, such as at each corner of the first plate 216.

Figure 4:
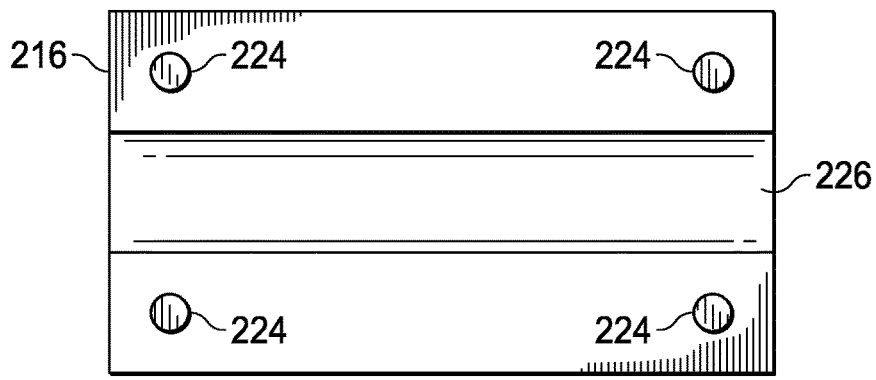
FIG. 4 is a top view of a retainer plate of the collection fitting of FIG. 2.

FIG. 4 is a top view of the first plate 216 illustrating additional details that may be associated with some embodiments of the collection fitting 206. In some embodiments, the first plate 216 includes four rods 224 and one rod 224 is positioned in each corner of the first plate 216. The rods 224 may be disposed on other locations of the first plate 216 on a surface having the channel 226. In other embodiments, the first plate 216 may have more or fewer rods 224.

Figure 5A:
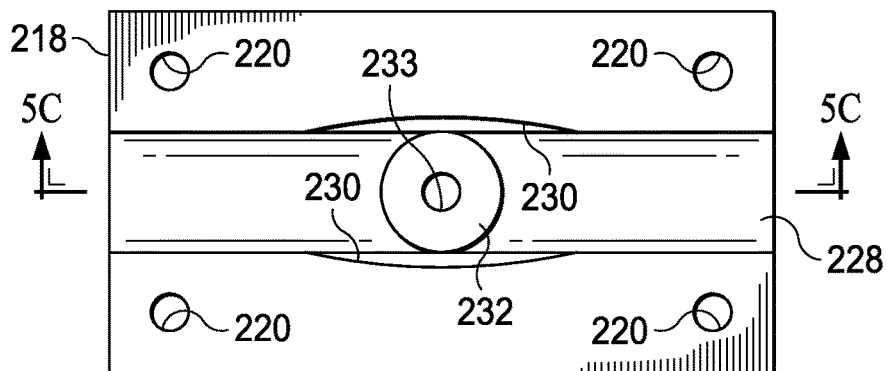
FIG. 5A is a bottom view of an access plate of the collection fitting of FIG. 2.

FIG. 5A is a bottom view illustrating additional details of the second plate 218. The second plate 218 may include the bores 220. The bores 220 may extend through the second plate 218 and may be dimensioned for an interference fit with the rods 224. In some embodiments, the second plate 218 includes four bores 220, each bore 220 positioned in a respective corner of the second plate 218. In other embodiments, there may be more or fewer bores 220. In other embodiments, the bores 220 may be disposed in other locations of the second plate 218. In some embodiments, the bores 220 may be located on the second plate 218 so that the bores 220 are substantially aligned with the rods 224 of the first plate 216 if the second plate 218 and the first plate 216 are engaged, as shown in FIG. 2.

The second plate 218 may also include a channel 228. The channel 228 may be similar to the channel 226 of the first plate 216. The channel 228 may extend from a first end to a second end of the second plate 218, and the channel 228 may be disposed along a major or minor axis of the second plate 218. In some embodiments, the channel 226 and the channel 228 may be positioned in the first plate 216 and the second plate 218, respectively, so that the channel 226 and the channel 228 may be substantially aligned. In some embodiments, the channel 226 and the channel 228 may be aligned so as to be coextensive. The channel 228 may have a semicircular profile having a diameter substantially equal to a diameter of the tube 208. In some embodiments, at least a portion of the tube 208 may be disposed within the channel 228. The channel 228 may also include recesses 230 formed in sidewalls of the channel 228. The recesses 230 may extend into the second plate 218 from a bottom surface of the second plate 218. The recesses 230 may be sized to accommodate portions of the wall of the tube 208 adjacent to the opening 234.

Figure 5B:
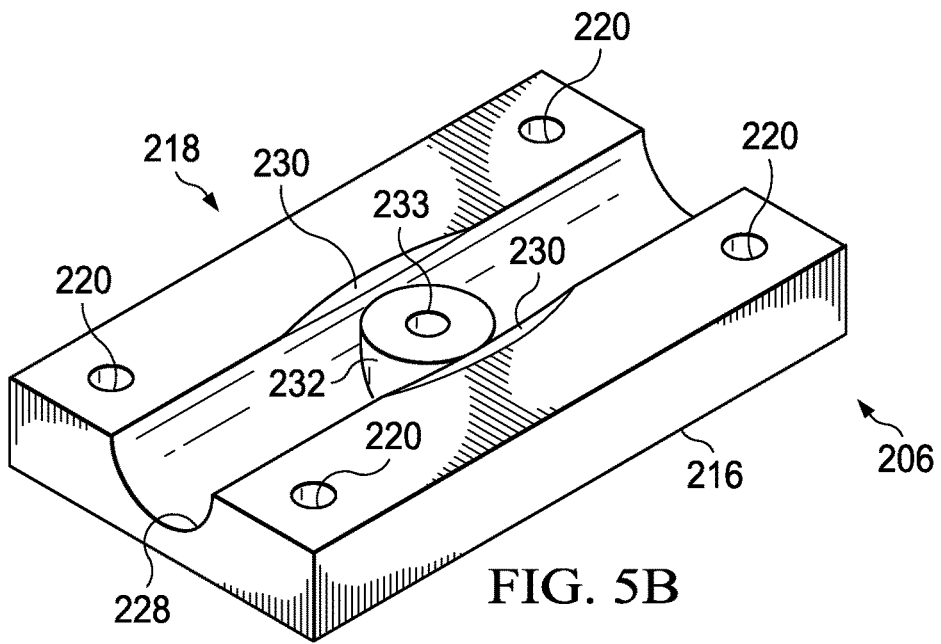
FIG. 5B is a bottom perspective view of the access plate of FIG. 5A.
Figure 5C:
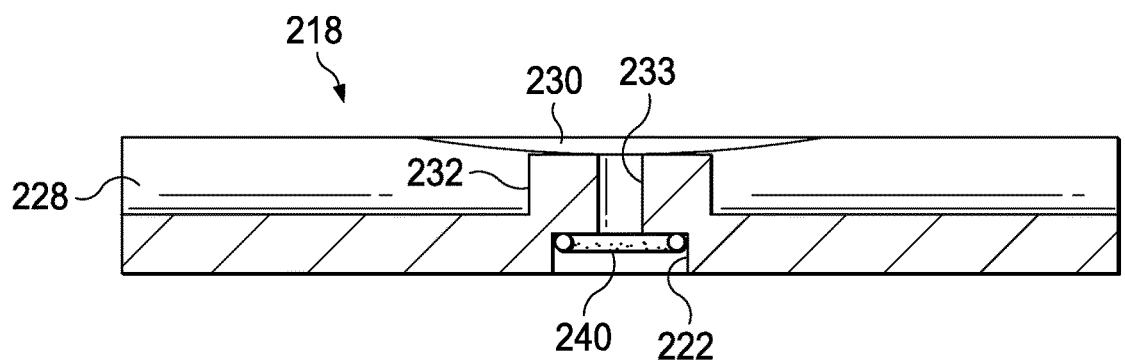
FIG. 5C is a cross-sectional view of the access plate of FIG. 5A taken along line 5C-5C.

FIG. 5B is a bottom perspective view of the second plate 218 illustrating additional details that may be associated with some embodiments; and FIG. 5C is a sectional view of the second plate 218 illustrating additional details that may be associated with some embodiments. The container union 222 may be disposed proximate to a center of the second plate 218 and extend through the second plate 218 into the channel 228. In some embodiments, the container union 222 includes a cylindrical boss 232. The cylindrical boss 232 is centrally disposed in the channel 228 adjacent to the recesses 230. In other embodiments, the container union 222 may be disposed in other portions of the channel 228. The cylindrical boss 232 may extend away from the channel 228, and in some embodiments, the cylindrical boss 232 may have a length extending into the channel 228 greater than a thickness of the wall of the tube 208. The cylindrical boss 232 may also include a passage 233 extending through the cylindrical boss 232 and providing a fluid path through the cylindrical boss 232 from the container union 222 to the channel 228.

Figure 6:
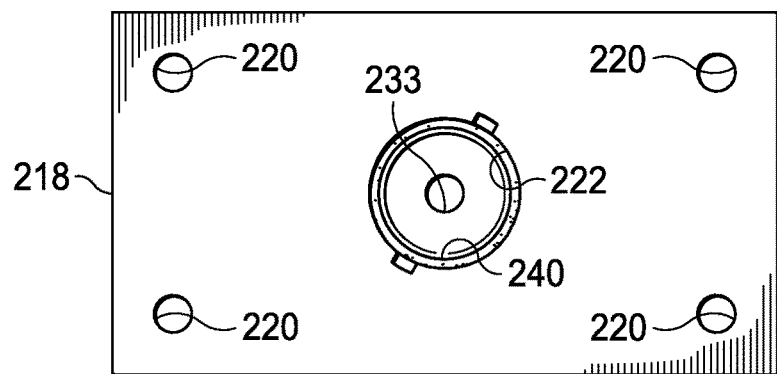
FIG. 6 is a top view of the access plate of the collection fitting of FIG. 2.

FIG. 6 is a top view illustrating additional details of the second plate 218. The container union 222 may be a union configured to receive a mating union. In some embodiments, the container union 222 may be a female union configured to receive a male union, allowing a male union to be coupled to the container union 222. In other embodiments, the container union 222 may be a male union, allowing a female union to be coupled to the container union 222. An O-ring 240 may be disposed in the container union 222. The O-ring 240 may be a sealing member configured to seal a mating union to the container union 222.

Figure 7:
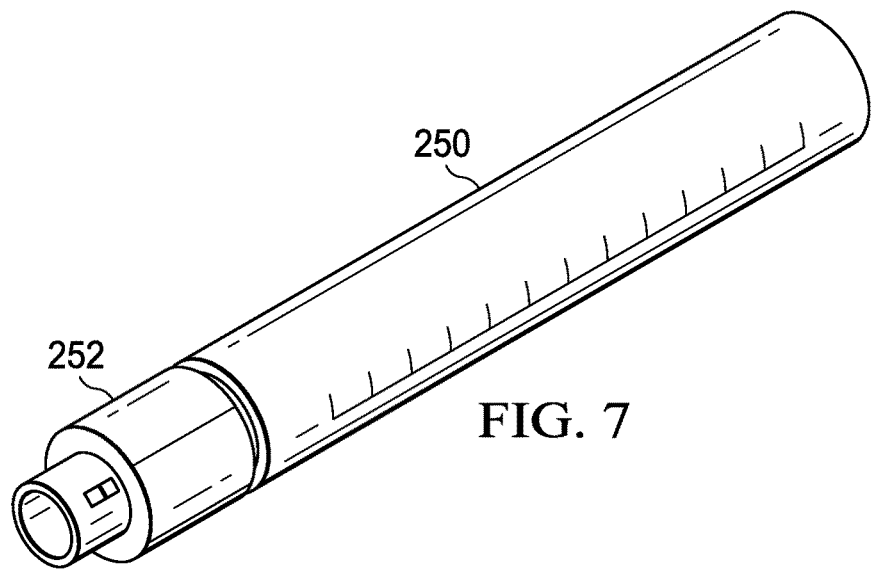
FIG. 7 is a perspective view of an example embodiment of a specimen container that may be used with a collection fitting such as the collection fitting of FIG. 2.

FIG. 7 is a perspective view illustrating additional details of a specimen container, such as a specimen container 250, that may be used with a fitting, such as the collection fitting 206. The specimen container 250 may be an illustrative embodiment of the specimen container 109. The specimen container 250 may be a tubular container having an open end and a closed end, and may be configured to receive and store a specimen or other fluid. In some embodiments, the specimen container 250 may include a top, such as a union 252 coupled to the open end of the specimen container 250. The union 252 may be configured to be coupled to the container union 222 and fluidly sealed to the O-ring 240. The union 252 may be male or female, depending on the gender of the container union 222. In some embodiments, the specimen container 250 may be graduated to determine a volume of fluid in the specimen container 250.

The collection fitting 206 may be assembled in the following manner. The tube 208 may be cut through the wall of the tube 208 to create the opening 234. Opposing sides of the opening 234 may be pulled apart so that the cylindrical boss 232 of the container union 222 may be inserted into the opening 234. The tube 208 may be positioned in the channel 228 so that the opening 234 is adjacent to the cylindrical boss 232 of the container union 222, and the cylindrical boss 232 may be inserted into the opening 234. The recesses 230 may accommodate portions of the tube 208 that have been separated to form the opening 234. The rods 224 may be inserted into the bores 220, positioning the tube 208 into the channel 226 of the first plate 216. The first plate 216 and the second plate 218 may be pressed together so that the opening 234 is completely enclosed by the connector 214. Adhesive may be applied to the bores 220 to couple the rods 224 of the first plate 216 to the bores 220 of the second plate 218, thereby securing the second plate 218 to the first plate 216 and enclosing the tube 208. In some embodiments, an adhesive may be applied to the first plate 216 adjacent to the channel 226 and to the second plate 218 adjacent to the channel 228. The adhesive may help to secure the second plate 218 to the first plate 216 while also providing a fluid seal between the second plate 218 and the first plate 216. In other embodiments, the rods 224 may be coupled to the bores 220 with an interference fit or with fasteners, for example. In still other embodiments, the rods 224 of the first plate 216 may be replaced with bores, and the second plate 218 and the first plate 216 may be secured with fasteners, for example.

In some embodiments, the collection fitting 206 may be assembled at a location where reduced-pressure therapy may be provided. For Example, the tube 208 may be fluidly coupled between a dressing and a reduced-pressure source. The connector 214 can be assembled around the tube 208, and a specimen can be collected from the tube 208 by coupling a specimen container, such as the specimen container 250, to the collection fitting 206. Thus, specimen collection may be provided where a reduced-pressure therapy system was not initially provided with a sampling location. In some embodiments, the collection fitting 206 may be assembled at a separate manufacturing location. For example, the tube 208 may be a section of tubing, the connector 214 may be assembled around the tube 208. The second union 238 and the first union 236 can join the section of tubing to other sections of tubing that are coupled between a dressing and a fluid collection apparatus. Thus, a treatment system may be provided that includes sampling from the initiation of treatment.

In operation, the collection fitting 206 may be fluidly coupled inline between a dressing and a reduced-pressure source or container, for example between the dressing 102 and the storage container 112 of FIG. 1. The fluid coupling of the collection fitting 206 inline between the dressing and the container allows fluid to flow from the dressing through the collection fitting 206 and into the container.

The union 252 of the specimen container 250 may be inserted into and coupled to the container union 222. The O-ring 240 may sealingly engage the union 252 to seal the container union 222 to the specimen container 250 and fluidly couple the specimen container 250 to the lumen 210 through the passage 233 of the container union 222. The reduced-pressure source may be operated to provide reduced pressure to the dressing through the lumen 210 of the tube 208. The fluid path may pass at least partially into the specimen container 250 through the container union 222. As fluids, including liquids from the tissue site, are drawn from the dressing through the lumen 210, the fluids may also be drawn into the specimen container 250. If a desired amount of fluid is in the specimen container 250, the reduced-pressure source may be paused, the specimen container 250 removed and replaced with another specimen container 250, and the reduced-pressure source may be resumed to continue reduced-pressure therapy.

In some embodiments, a valve may be coupled to the container union 222. The valve may be operated to selectively permit fluid communication through the container union 222. Consequently, the valve may permit the specimen container 250 to be coupled to and uncoupled from the collection fitting 206 without ceasing provision of reduced-pressure therapy.

Tee-Fitting

Figures 8A, 8B:
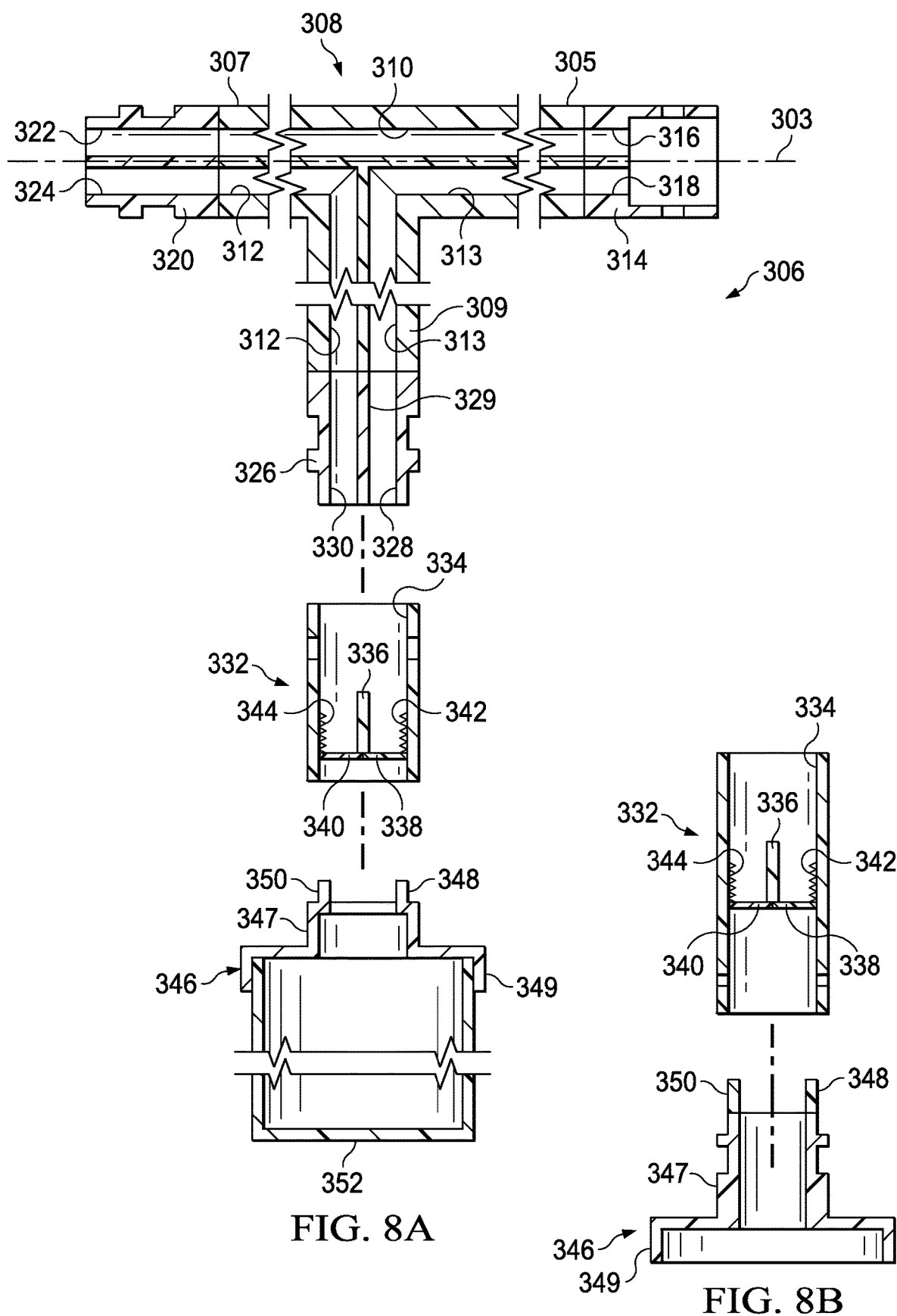
FIG. 8A is a cross-sectional view of another example embodiment of a collection fitting that may be associated with some embodiments of the reduced-pressure therapy system of FIG. 1 according to this specification.
FIG. 8B is a cross-sectional view of a portion of the collection fitting of FIG. 8A having another example of a union that may be associated with some embodiments.

FIG. 8A is a cross-sectional schematic diagram illustrating additional details that may be associated with an example embodiment of a collection fitting 306 that may be used with a reduced-pressure therapy system, for example, the reduced-pressure therapy system 100. The collection fitting 306 may include a three-way fitting, such as a tee-fitting 308, a first union 320, a second union 314, and a container union 326. The tee-fitting 308 may include at least three arms: a first arm 305, a second arm 307, and a third arm 309. The first arm 305 and the second arm 307 may be coaxial about an axis 303 of the tee-fitting 308 and opposite one another. In other embodiments, the first arm 305 and the second arm 307 are not coaxial. The third arm 309 may be perpendicular to the first arm 305 and the second arm 307. In some embodiments, the third arm 309 may be disposed between the first arm 305 and the second arm 307. In other embodiments, the first arm 305, the second arm 307, and the third arm 309 may be equidistantly spaced from each other. In these embodiments, no arm is coaxial with another and no arm may be perpendicular to another.

The tee-fitting 308 may include a plurality of lumens. For example, in some embodiments, the tee-fitting 308 may include a secondary lumen, such as a lumen 310, a first primary lumen, such as a lumen 312, and a second primary lumen, such as a lumen 313. In some embodiments, the lumen 310 may extend through the tee-fitting 308 from the first arm 305 to the second arm 307. The lumen 312 may extend through the tee-fitting 308 from the second arm 307 to the third arm 309, and the lumen 313 may extend through the tee-fitting 308 from the first arm 305 to the third arm 309.

The first union 320 may be coupled to the second arm 307 of the tee-fitting 308 as shown in some embodiments of FIG. 8A. The first union 320 may include a secondary lumen, for example, a lumen 322, and a central lumen, for example, a lumen 324. The first union 320 may be coupled to the second arm 307 of the tee-fitting 308, so that the lumen 322 is fluidly coupled to the lumen 310 and the lumen 324 of the first union 320 is fluidly coupled to the lumen 312. The first union 320 may be inserted into a union of opposite gender to secure the tee-fitting 308 to a tube, or another device.

The second union 314 may be coupled to the first arm 305 of the tee-fitting 308 as shown in some embodiments of FIG. 8A. The second union 314 may include a secondary lumen, for example, a lumen 316, and a primary lumen, for example, a lumen 318. The second union 314 may couple to the first arm 305 of the tee-fitting 308, so that the lumen 316 is fluidly coupled to the lumen 310 and the lumen 318 is fluidly coupled to the lumen 313. The second union 314 may be configured to receive a union of opposite gender to couple the second union 314 to an additional conduit or to another device.

The container union 326 may be coupled to the third arm 309 of the tee-fitting 308. The container union 326 may include a lumen 328 and a lumen 330. The container union 326 may be coupled to the third arm 309 of the tee-fitting 308 so that the lumen 328 may be fluidly coupled to the lumen 313, and the lumen 330 may be fluidly coupled to the lumen 312. The lumen 328 and the lumen 330 may be separated by a wall 329 extending a length of the container union 326. The lumen 328 may be sized to accommodate a flow rate that is substantially equivalent to a flow rate through the lumen 313. Similarly, the lumen 330 may be sized to accommodate a flow rate that is substantially equivalent to a flow rate through the lumen 312. The container union 326 may be inserted into a union of opposite gender to fluidly couple the third arm 309 of the tee-fitting 308 to a tube or another device.

The collection fitting 306 may also include a valve, such as a valve 332. The valve 332 may include a passage 334 and a wall 336. The passage 334 may be sized to accommodate a flow rate that is substantially equivalent to a flow rate through the lumen 328 and the lumen 330. The valve 332 may have a first end configured to be coupled to the container union 326. The wall 336 may be disposed within the passage 334 proximate to a second end of the valve 332. In some embodiments, the wall 336 may bisect the passage 334 into two semicircular halves proximate to the second end of the valve 332. The wall 336 may have a length such that, if the valve 332 is coupled to the container union 326, an end of the wall 336 may contact the wall 329.

A flap 338 may be disposed in the passage 334 proximate to the second end. The flap 338 may have a dimension, for example a diameter or width, substantially equal to a portion of the bisected passage 334. In some embodiments, the flap 338 may have a semicircular shape. The flap 338 may block fluid flow through at least half of the passage 334 if in a closed position, as shown in some embodiments of FIG. 8A. The flap 338 may be hinged so that the flap 338 may pivot between the closed position and an open position that allows fluid flow through a portion of the passage 334. In some embodiments, the flap 338 may be hinged proximate to an outer wall of the valve 332 so that a first end of the flap 338, may pivot toward the outer wall of the valve 332. In some embodiments, a vertex of the flap 338 may be coupled to a biasing mechanism, for example, a spring 342. In some embodiments, the spring 342 may be coupled to the outer wall of the valve 332 and be positioned so that the spring 342 is in a relaxed state if the flap 338 is in the closed position. In other embodiments, the flap 338 may be coupled to the spring 342 so that the spring 342 resists opening of the flap 338.

Similarly, a flap 340 may be disposed in the passage 334 adjacent to the flap 338. The flap 340 may have a dimension, for example a diameter, substantially equal to a portion of the bisected passage 334. In some embodiments, the flap 340 may have a semicircular shape and block passage through at least half of the passage 334 if in a closed position of FIG. 8A. In some embodiments, the flap 340 and the flap 338 may each block a respective half of the passage 334 in the closed position of FIG. 8A. The flap 340 may be hinged so that the flap 340 may pivot between the closed position blocking fluid flow through a portion of the passage 334 and an open position that allows fluid flow through a portion of the passage 334. In some embodiments, the flap 340 may be hinged proximate to an outer wall of the valve 332 so that a first end of the flap 340 may pivot toward the outer wall of the valve 332. In some embodiments, a vertex of the flap 340 may be coupled to a biasing mechanism, for example, a spring 344. In some embodiments, the spring 344 may be coupled to the outer wall of the valve 332 and be positioned so that the spring 344 is in a relaxed state if the flap 340 is in the closed position. In some embodiments, the flap 340 may be coupled to the spring 344 so that the spring 344 resists opening of the flap 340.

In some embodiments, the collection fitting 306 may also include an actuator, such as an actuator 346, for example. In some embodiments, the actuator 346 may be configured as a lid or cap for a container, such as a specimen container 352. The actuator 346 may have a first end 347 having a first dimension, such as a diameter, for example, and a second end 349 having a second dimension, such as a diameter, for example. In some embodiments, the second dimension is greater than the first dimension. In other embodiments, the first dimension and the second dimension may be substantially equal. The actuator 346 may also be a substantially tubular body. The actuator 346 may include a first rod 348 and a second rod 350. The first rod 348 may be positioned on an inner diameter of the first end 347 of the actuator 346 and may extend away from the actuator 346 so that the first rod 348 protrudes from the actuator 346. Similarly, the second rod 350 may also be positioned on the inner diameter of the first end 347 of the actuator 346. The second rod 350 may also extend away from the actuator 346 so that the second rod 350 protrudes from the first end 347 of the actuator 346. In some embodiments, the first rod 348 and the second rod 350 may be opposite one another on the first end 347 of the actuator 346. In other embodiments, the first rod 348 and the second rod 350 may not be opposite one another.

The first end 347 of the actuator 346 may have an outer diameter substantially equivalent to an outer diameter of the valve 332. An inner diameter of the first end 347 of the actuator 346 may be dimensioned so that an interior of the first end 347 of the actuator 346 may be coextensive with the passage 334. In some embodiments, the first rod 348 and the second rod 350 may be positioned so that they are substantially aligned with the spring 342 and the spring 344 of the valve 332 if the first end 347 of the actuator 346 is proximate to the valve 332.

The specimen container 352 may be a tubular body having a closed end and an open end. In some embodiments, the specimen container 352 may be translucent. In some embodiments, the specimen container 352 may be opaque. In some embodiments, the specimen container 352 may be graduated so that a volume of fluid in the specimen container 352 may be measured. The second end 349 of the actuator 346 may have an inner diameter that may be coextensive with the open end of the specimen container 352. In some embodiments, the inner diameter of the actuator 346 may be threaded to receive a threaded open end of the specimen container 352.

FIG. 8B is a sectional view of the actuator 346 illustrating another embodiment that may be used with some embodiments of the collection fitting 306. In some embodiments, the actuator 346 may include a male union, similar to the container union 326, proximate to the rod 348 and the rod 350. In these embodiments, the rod 348 and the rod 350 may be disposed on an end of the male union so that the male union may be inserted into a respective female union. In these embodiments, the rod 348 and the rod 350 may be coupled to an end of the male union, rather than on an inner diameter of the first end 347 of the actuator 346.

Figures 9A, 9B:
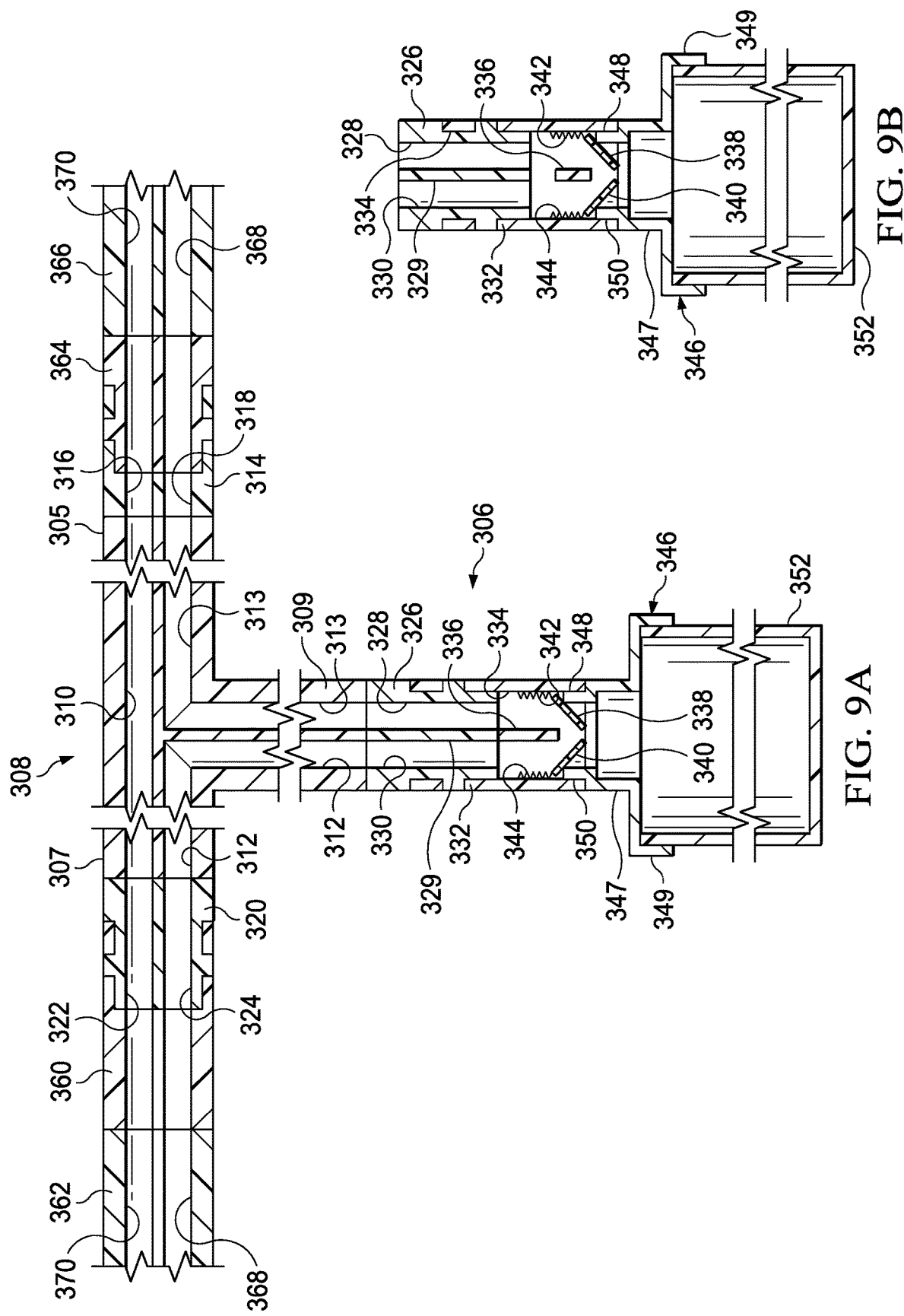
FIG. 9A is a cross-sectional view of the collection fitting of FIG. 8A coupled to one or more components of a reduced-pressure therapy system.
FIG. 9B is a cross-sectional view of a portion of the collection fitting of FIG. 8A having another example embodiment of a valve.

FIG. 9A is a sectional view of the collection fitting 306 illustrating additional details that may be associated with some embodiments. In some embodiments, the collection fitting 306 may be fluidly coupled inline between a dressing and a container or reduced-pressure source. For example, the first union 320 may be fluidly coupled through a union 360 to a tube 362 and then to a container, such as the storage container 112, for example, which may be fluidly coupled to a reduced-pressure source, for example, the reduced-pressure source 104. Similarly, the second union 314 may be fluidly coupled through a union 364 to a tube 366 and then to a dressing, for example, the dressing 102. The tube 362 and the tube 366 may be multi-lumen conduits having a primary lumen 368 and one or more secondary lumens 370. In some embodiments, the first union 320 and the second union 314 may fluidly couple the secondary lumens 370 of the tube 362 and the tube 366 to the lumen 310. The first union 320 may also fluidly couple the primary lumen 368 of the tube 362 to the lumen 312, and the second union 314 may fluidly couple the primary lumen 368 of the tube 366 to the lumen 313.

The valve 332 may be coupled to the container union 326 so that the passage 334 of the valve 332 is fluidly coupled to both the lumen 328 and the lumen 330. Coupling the valve 332 to the container union 326 places the passage 334 in fluid communication with the lumen 312 and the lumen 313 of the third arm 309.

The actuator 346 may be coupled to the specimen container 352 and brought proximate to the valve 332. The first end 347 of the actuator 346 may be adjacent to the valve 332 so that the first rod 348 and the second rod 350 may insert into the passage 334. If the first rod 348 and a second rod 350 insert into the passage 334, the first rod 348 and the second rod 350 may move the flap 338 and the flap 340, respectively, upwards into the passage 334. In some embodiments, the upward movement may pivot the flap 338 and the flap 340 to the open position, permitting fluid flow through the valve 332 and the actuator 346 into the specimen container 352.

In some embodiments, a reduced-pressure source may be fluidly coupled to the lumen 312, and a dressing may be fluidly coupled to the lumen 313 through the secondary lumens 370 of the tube 362 and the tube 366, respectively. Reduced pressure may flow through the primary lumen 368 of the tube 362, the lumen 312, the lumen 330 of the container union 326, the passage 334 of the valve 332, and into the specimen container 352. Reduced pressure may flow to the tissue site from the specimen container 352, through the passage 334 of the valve 332, the lumen 328 of the container union, the lumen 313, and the primary lumen 368 of the tube 366 to provide reduced-pressure therapy to the tissue site through the collection fitting 306.

The flow of reduced pressure through the collection fitting 306 may draw fluids, including liquids from the tissue site, into and through the specimen container 352. Liquids from the tissue site may collect in the specimen container 352. If a desired amount of liquids from the tissue site has been collected in the specimen container 352, the actuator 346 and the specimen container 352 may be uncoupled from the valve 332. In response, the rod 348 and the rod 350 may be removed from the passage 334. The spring 342 and the spring 344 may push the flap 338 and the flap 340 to the closed position as shown in some embodiments of FIG. 8A, preventing further fluid communication through the valve 332.

In some embodiments, a fluidly coupled reduced-pressure source may be capable of determining a pressure at a tissue site. For example, a reduced-pressure source may be able to determine whether a pressure applied at a tissue site is about a desired pressure for reduced-pressure therapy. In these embodiments, the lumen 310 may be fluidly coupled to a reduced-pressure source through the secondary lumen 370 of the tube 362 and further fluidly coupled to a dressing through the secondary lumen 370 of the tube 366. In some embodiments, the lumen 310 may act as a sensing lumen that communicates a pressure at a tissue site to a reduced-pressure source. The lumen 310 may be an independent path of fluid communication so that the lumen 310 may be unaffected by sampling with the specimen container 352.

FIG. 9B is a sectional view of a portion of the collection fitting 306 illustrating additional details that may be associated with some embodiments. For example, the wall 336 may have a length such that the end of the wall 336 may not contact the wall 329. As shown in FIG. 9, there may be a gap between the wall 336 and the wall 329. In these embodiments, fluid communication may occur between the lumen 328 and the lumen 330 through the gap if the actuator 346 is not engaged with the valve 332. In other embodiments, as shown in FIG. 9A, there may be no gap, and no fluid communication may occur between the lumen 328 and the lumen 330 if the actuator 346 is not engaged with the valve 332.

In some embodiments, the valve 332 may be coupled to the container union 222 of the connector 214 described above with respect to FIG. 2 through FIG. 7. In those embodiments, the specimen container 250 may have the actuator 346 coupled to the open end of the specimen container 250. The valve 332 and the actuator 346 may operate to selectively permit fluid communication through the container union 222.

Figure 10:
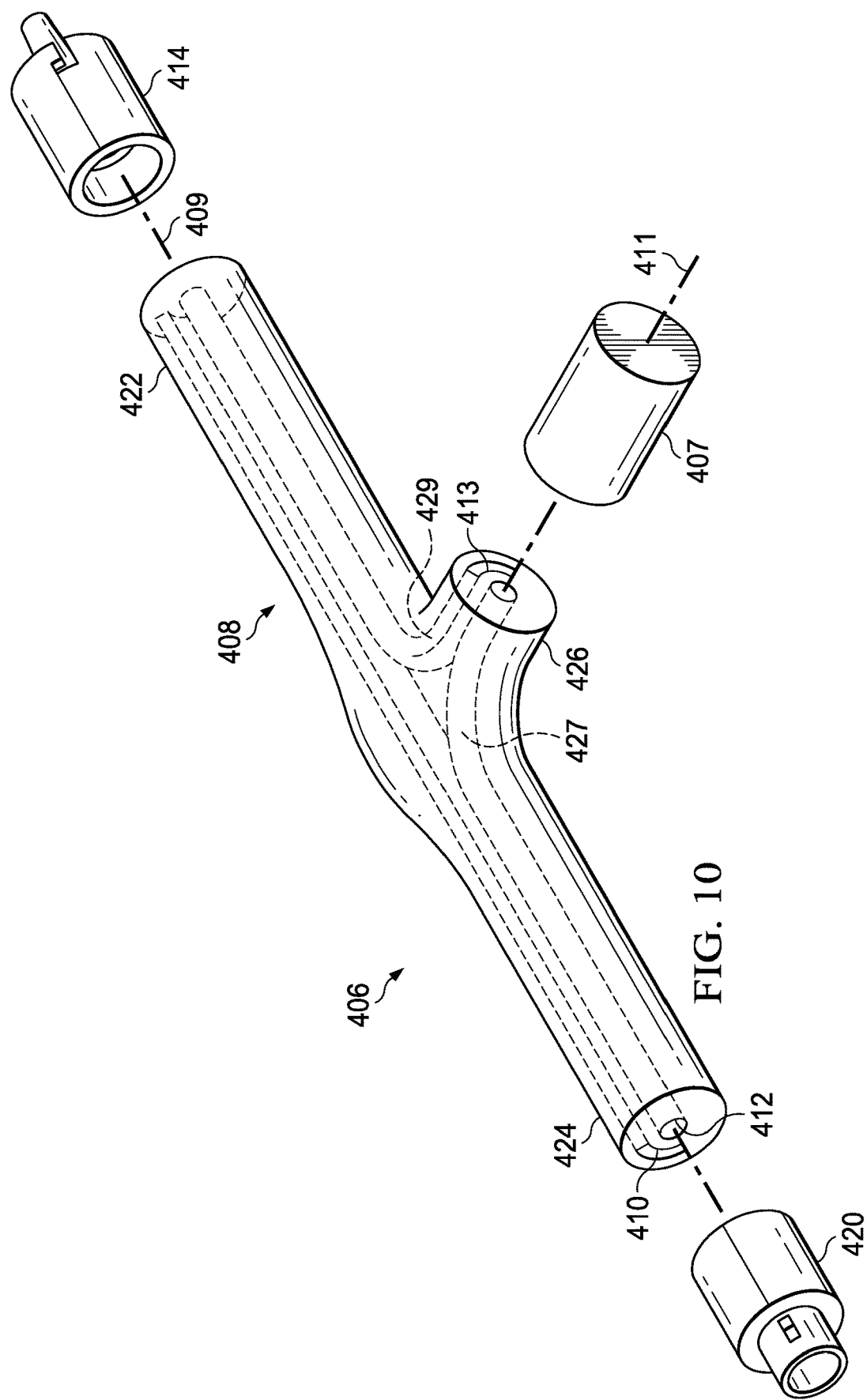
FIG. 10 is a perspective view of another example embodiment of a collection fitting having a tee-fitting that may be associated with some embodiments of the reduced-pressure therapy system of FIG. 1 according to this specification.

FIG. 10 is a perspective view illustrating additional details of a collection fitting 406 that may be used with a reduced-pressure therapy system, for example, the reduced-pressure therapy system 100. The collection fitting 406 may include a tee-fitting 408, a first union 414, and a second union 420. The tee-fitting 408 may have a first arm 422, a second arm 424, and a third arm 426. The first arm 422 and the second arm 424 may be coaxial about an axis 409 and opposite one another. The third arm 426 may have an axis 411 that may be perpendicular to the axis 409 of the first arm 422 and the second arm 424. In other embodiments, the axis 411 of the third arm 426 may be at a non-perpendicular angle to the axis 409 of the first arm 422 and the second arm 424. In some embodiments, the first arm 422, the second arm 424, and the third arm 426 may be equidistantly separated from each other so that no arm is perpendicular or coaxial with any other arm. In some embodiments, the third arm 426 may be disposed proximate to a center of the tee-fitting 408. In other embodiments, the third arm 426 may be disposed in other locations of the tee-fitting 408.

The tee-fitting 408 may also have a plurality of lumens. In some embodiments, the tee-fitting 408 may include one or more peripheral lumens, for example, a lumen 410. The lumen 410 may be a fluid path that extends from the first arm 422 to the second arm 424 of the tee-fitting 408. In some embodiments, the lumen 410 may be separated from the axis 409. The lumen 410 may have an outer boundary having a radius extending a first distance from the axis 409. The lumen 410 may have an inner boundary having a radius extending a second distance from the axis 409. In some embodiments, the first distance may be greater than the second distance. The lumen 410 may have an arcuate length that is a portion of a circumference of the tee-fitting 408 about the axis 409. In some embodiments, the lumen 410 extends through the tee-fitting 408 from the first arm 422 to the second arm 424 and does not pass through the third arm 426.

The tee-fitting 408 may also include a first primary lumen, for example, a lumen 412 and a second primary lumen, for example, a lumen 413. The lumen 412 extends through the tee-fitting 408 from the second arm 424 to the third arm 426. In some embodiments, the lumen 412 may be disposed proximate to a center of the second arm 424 and may have a circular cross-section. In some embodiments, the portion of the lumen 412 in the second arm 424 may be coaxial with the axis 409. The portion of the lumen 412 in the third arm 426 may be disposed proximate to a center of the third arm 426 and may have a circular cross-section. In some embodiments, the lumen 412 may have a portion that is coaxial with the axis 411 of the third arm 426. The lumen 412 may include an elbow 427 proximate to the union of the third arm 426 and the second arm 424. In some embodiments, the elbow 427 may have a radius of curvature causing the lumen 412 to turn about 90°.

The lumen 413 may extend through the tee-fitting 408 from the first arm 422 to the third arm 426. The lumen 413 may be coaxial with the axis 409 and have a circular cross-section. The lumen 413 may be coaxial with the axis 411 and may have a non-circular cross-section proximate to an end of the third arm 426. In some embodiments, the lumen 413 may be separated from the lumen 412 in the third arm 426. For example, the lumen 413 may have an outer boundary having a radius extending from the axis 411 of the third arm 426 a first distance. The lumen 413 may have an inner boundary having a radius extending from the axis 411 of the third arm 426 a second distance. In some embodiments, the first distance may be greater than the second distance. The lumen 413 may have an arcuate length that is a portion of a circumference of the third arm 426. The lumen 413 may have an elbow 429 that transitions the lumen 413 from a circular to a non-circular cross-section proximate to the union of the first arm 422 and the third arm 426. In some embodiments, the elbow 429 may have a radius of curvature of about 90°. The lumen 412 and the lumen 413 may be adjacent to one another in the third arm 426 so that the inner boundary of the lumen 413 may partially circumscribe the lumen 412.

The first union 414 may be coupled to the first arm 422, and the second union 420 may be coupled to the second arm 424. Both the first union 414 and the second union 420 may include lumens configured to fluidly couple with the respective lumens of the tee-fitting 408. The second union 420 may be coupled with another union to fluidly couple the collection fitting 406 to a reduced-pressure source, a dressing, or other device. Similarly, the first union 414 may be coupled with another union to fluidly couple the collection fitting 406 with a dressing, a reduced-pressure source, or other device.

In some embodiments, a valve 407 may be coupled to the third arm 426. In some embodiments, the valve 407 may be a valve assembly coupled to the third arm 426 and be operable to selectively permit fluid communication through the third arm 426. In some embodiments, the valve 407 may be fluidly coupled to a specimen container, such as a vial, a graduated cylinder, or a bottle, for example. In these embodiments, the valve 407 may selectively permit fluid communication into and through the specimen container. In some embodiments, the valve 407 may be similar to and operate in a manner similar to the valve 332.

FIG. 11 is a perspective view illustrating additional details of another tee-fitting 508 that may be used with a collection fitting, such as the collection fitting 306 or the collection fitting 406, for example. In some embodiments, the tee-fitting 508 may be a generally triangular-shaped body. The tee-fitting 508 may include a first arm 522, a second arm 524, and a third arm 526. The first arm 522 and the second arm 524 may be coaxial about an axis 509 and opposite one another. The first arm 522, the second arm 524, and the third arm 526 may all have generally circular cross-sections proximate to ends of each respective arm. The third arm 526 may be a cylindrical body having an axis 511 that is perpendicular to the axis 509 of the first arm 522 and the second arm 524. In other embodiments, the third arm 526 may be at a non-perpendicular angle to the axis 509. In some embodiments, the third arm 526 may be disposed proximate to a center of the tee-fitting 508. In other embodiments, the third arm 526 may be disposed in other locations of the tee-fitting 508. In some embodiments, the tee-fitting 508 may have a triangular shape. The first arm 522, the second arm 524, and the third arm 526 may be positioned on a respective vertex of the triangularly-shaped tee-fitting 508. The tee-fitting 508 may have a partially cylindrical outer surface extending between the first arm 522 and the second arm 524. The tee-fitting 508 may have exterior surfaces extending between the first arm 522 and the third arm 526 that may form an angle 507 to the axis 509. In some embodiments, the angle 507 may be about 30 degrees. Similarly, the tee-fitting 508 may have exterior surfaces extending between the second arm 524 and the third arm 526 that may form an angle 505 to the axis 509. In some embodiments, the angle may be about 30 degrees.

The tee-fitting 508 may also have a plurality of lumens. In some embodiments, the tee-fitting 508 may include one or more peripheral lumens, for example, a lumen 510. The lumen 510 may be a fluid path that extends through the tee-fitting 508 from the first arm 522 to the second arm 524 of the tee-fitting 508. In some embodiments, the lumen 510 may be separated from the axis 509. The lumen 510 may have an outer boundary having a first radius from the axis 509. The lumen 510 may have an inner boundary having a second radius from the axis 509. In some embodiments, the first radius may be greater than the second radius. The lumen 510 may have an arcuate length that is a portion of a circumference of the tee-fitting 508 adjacent to the ends of the first arm 522 and the second arm 524.

The tee-fitting 508 may also include a first primary lumen, for example, a lumen 512 and a second primary lumen, for example, a lumen 513. The lumen 512 may extend through the tee-fitting 508 from the second arm 524 to the third arm 526. In some embodiments, the lumen 512 maybe be disposed proximate to a center of the second arm 524 and may have a circular cross-section. The lumen 512 may also have a semicircular cross-section proximate to the third arm 526. The lumen 512 may have a shape that transitions the lumen 512 from the circular cross-section proximate to an end of the second arm 524 to the semicircular cross-section proximate to an end of the third arm 526. In some embodiments, the lumen 512 forms an angle with the axis 509 between the second arm 524 and the third arm 526. In some embodiments, the angle may be about 30° to the axis 509. The portion of lumen 512 in the third arm 526 may be perpendicular to the axis 509.

The lumen 513 may extend through the tee-fitting 508 from the first arm 522 to the third arm 526. In some embodiments, the lumen 513 may be disposed proximate to a center of the first arm 522 and may have a circular cross-section. The lumen 513 may also have a semicircular cross-section proximate to an end of the third arm 526. The lumen 513 may have a shape that transitions the lumen 513 from the circular cross-section proximate to an end of the first arm 522 to the semicircular cross-section proximate to an end of the third arm 526. In some embodiments, the lumen 513 forms an angle with the axis 509 between first arm 522 and the third arm 526. In some embodiments, the angle may be about 30° to the axis 509. The portion of lumen 513 in the third arm 526 may be perpendicular to the axis 509.

The tee-fitting 508 may be coupled to tubes, conduits, or other devices with unions, for example, the second union 420 and the first union 414 of FIG. 10. In this manner, the tee-fitting 508 may be fluidly coupled inline between a dressing and a container or a reduced-pressure source. In addition, the tee-fitting 508 may have a valve coupled to the third arm, such as the valve 407 of FIG. 10, for example.

In some embodiments, a fluidly coupled reduced-pressure source may be capable of determining a pressure at the tissue site. For example, the reduced-pressure source may be able to determine whether a pressure applied at the tissue site is about the desired reduced pressure for reduced-pressure therapy. In these embodiments, the lumen 410 of the collection fitting 406 and the lumen 510 of the collection fitting 506 may be fluidly coupled to the reduced-pressure source and further fluidly coupled to the dressing through the second union 420 and the first union 414. In some embodiments, the lumen 410 and the lumen 510 may be a sensing lumen that communicates the pressure at the tissue site to the reduced-pressure source so that the reduced-pressure source may determine whether additional reduced pressure should be supplied. The lumen 410 and the lumen 510 may be independent paths of fluid communication so that the lumen 410 and the lumen 510 may be unaffected by sampling with a specimen container.

FIG. 12A is a perspective view of a valve 600 having internal components shown in hidden lines that may be used with the container union 222 of the connector 214 of FIG. 2, the third arm 309 of the tee-fitting 308 of FIG. 8A, the third arm 426 of the tee-fitting 408 of FIG. 10, or the third arm 526 of the tee-fitting 508 of FIG. 11. The valve 407 of FIG. 10 may be similar to and operate as described below with respect to the valve 600 of FIG. 12A. The valve 600 includes a valve housing 602, a valve spring 608, and a ball 610. The valve housing 602 may be a tubular member having a first end 604 and a second end 606. The first end 604 may include a connector. A retainer ring 612 may be coupled to an inner surface of the valve housing 602. The retainer ring 612 may be separated a distance from the first end 604. The retainer ring 612 may have an inner diameter less than a diameter of the ball 610. In some embodiments, the valve housing 602 may have rails 609 formed on the inner diameter surface of the valve housing 602. The rails 609 may be parallel to an axis of the valve housing 602 and extend from the retainer ring 612 to the second end 606 of the valve housing 602. The rails 609 extend radially into the valve housing 602 from the inner diameter of the valve housing 602. The rails 609 may form passages 611 between adjacent rails 609.

The ball 610 may be a spherical body having a diameter that is less than a distance between radial ends of opposing rails 609. For example, in some embodiments, the ball 610 may have a diameter such that an outer surface of the ball 610 may contact opposing rails 609 and move freely relative to the rails 609. The ball 610 may be disposed inside of the valve housing 602 and may be configured to move axially along the length of the valve housing 602 between the retainer ring 612 and the second end 606.

The valve spring 608 may be a biasing member disposed between the ball 610 and the second end 606. The valve spring 608 may bias the ball 610 against the retainer ring 612 so that the ball 610 may sealingly engage the retainer ring 612. In some embodiments, the retainer ring 612 may have a sealing member positioned on a surface opposite the first end 604.

FIG. 12B is an end view illustrating additional details of the valve 600. The second end 606 may include a spring plate 614 coupled to the valve housing 602 proximate to the second end 606. The spring plate 614 may be an annular body having peripheral portions coupled to the inner diameter surface of the valve housing 602 and the rails 609. In some embodiments, the spring plate 614 forms an end of the passages 611 of FIG. 12A. As shown in FIG. 12B, the spring plate 614 may form an opening 615 that may be coaxial with the axis of the valve housing 602.

The valve spring 608 may have a first end in contact with the ball 610 and a second end in contact with the spring plate 614. In some embodiments, the valve spring 608 may be a conical spring having a wider diameter proximate to the second end 606 and a narrower diameter proximate to the ball 610. The wider diameter end of the valve spring 608 may be engaged with or be operatively coupled to the spring plate 614, and the narrower diameter end of the valve spring 608 may be engaged with or be operatively coupled to the ball 610. In other embodiments, the valve spring 608 may be a cylindrical spring. The operative engagement between the valve spring 608, the ball 610, and the spring plate 614 may permit an actuator force acting on the ball 610 in a direction along the axis of the valve housing 602 from the first end 604 toward the second end 606 to compress the valve spring 608 against the spring plate 614.

In some embodiments, the valve 600 may be coupled to the container union 222 of the connector 214, the third arm 309 of the tee-fitting 308, the third arm 426 of the tee-fitting 408, or the third arm 526 of the tee-fitting 508. In operation, the ball 610 may be pressed against the retainer ring 612 by the valve spring 608, sealing the ball 610 against the retainer ring 612. In this manner, the ball 610 may place the valve 600 in a closed position, preventing fluid communication through the valve 600. The actuator force may be exerted against the ball 610 in a direction parallel to the axis of the valve housing 602, moving from the first end 604 toward the second end 606. The actuator force may move the ball 610 axially into the valve housing 602 into an open position, where the ball 610 is out of sealing engagement with the retainer ring 612. Movement of the ball 610 into the valve housing 602 toward the spring plate 614 may open a fluid path through the valve 600. In some embodiments, the fluid path may flow through the opening 615 of the spring plate 614, through the passages 611 around the ball 610, through the opening of the retainer ring 612 and out of the valve 600. If the actuator force is removed, the valve spring 608, which may have been compressed a distance by the force, may exert a counterforce proportional to a spring constant of the valve spring 608 and the distance the valve spring 608 was compressed. The counterforce may return the ball 610 to the closed position into sealing engagement with the retainer ring 612.

Figure 13:
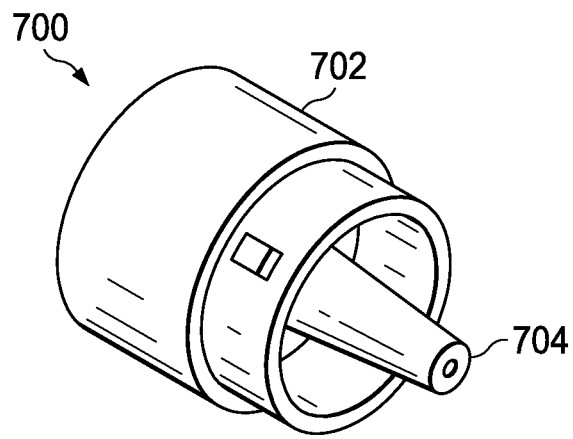
FIG. 13 and FIG. 14 are perspective views of an example embodiment of an actuator that may be used with the illustrative sampling valve of FIG. 12A.

FIG. 13 is a perspective view of an actuator 700 that may be used with some embodiments of the valve 600 of FIG. 12A and FIG. 12B by applying the actuator force. The actuator 700 may include a actuator housing 702 and a protrusion 704. The actuator housing 702 may be a tubular body having a length and a union. In some embodiments, the union may have suitable structures so that the union is configured to be coupled to the union of the first end 604 of the valve 600. An end of the actuator housing 702 opposite the union may be configured to be coupled to a specimen container, such as a vial, a graduated cylinder, or a bottle, for example.

In some embodiments, the protrusion 704 may be a frustum. In other embodiments, the protrusion 704 may be other shapes, such as a cylindrical shape, for example. The protrusion 704 may protrude from the union of the actuator housing 702. The protrusion 704 may have an interior end disposed within an interior of the actuator housing 702. In some embodiments, the protrusion 704 is hollow. In other embodiments the protrusion 704 is not hollow. The protrusion 704 may have an outer diameter less than the inner diameter of the actuator housing 702, thereby forming a fluid path between the protrusion 704 and the inner diameter surface of the actuator housing 702.

Figure 14:
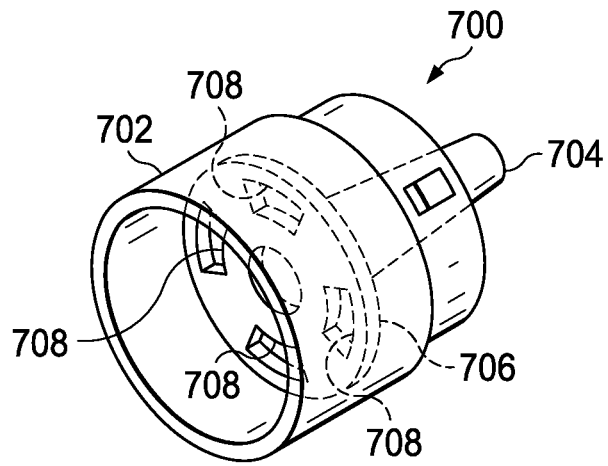

FIG. 14 is a perspective view of the actuator 700 having internal portions shown in hidden lines, illustrating additional details that may be associated with some embodiments. As shown in some embodiments of FIG. 14, the actuator 700 may also include a mounting plate 706. The mounting plate 706 may be disposed in the interior of the actuator housing 702 and may have peripheral portions coupled to the inner diameter surface of the actuator housing 702. The mounting plate 706 may be separated a distance from an end of the actuator housing 702. The protrusion 704 may have the interior end of the protrusion 704 coupled to the mounting plate 706 proximate to a center portion of the mounting plate 706. The protrusion 704 may extend from the mounting plate 706 out of the actuator housing 702 so that the protrusion 704 extends beyond the male end of the actuator housing 702. The mounting plate 706 may also include a plurality of holes 708. The holes 708 may extend through the mounting plate 706 to permit fluid communication through the mounting plate 706. The holes 708 may be circumferentially spaced around the mounting plate 706. In other embodiments, the holes 708 may not be circumferentially spaced around the mounting plate 706.

Figure 15:
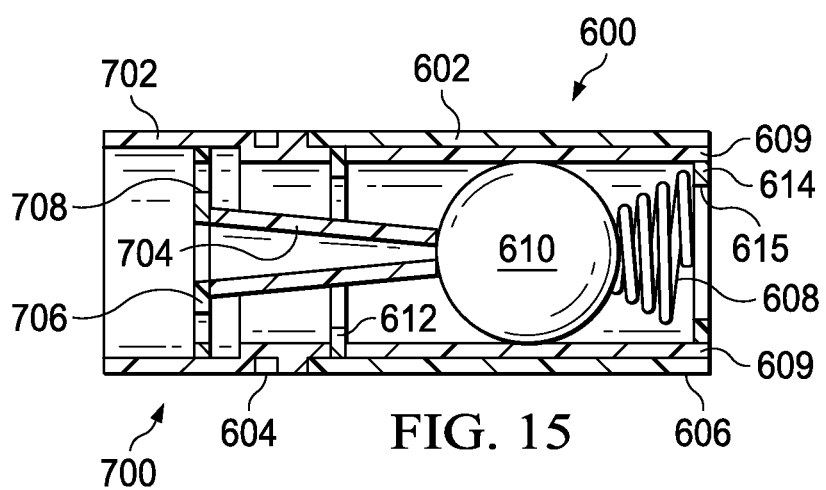
FIG. 15 is a cross-sectional view of the actuator of FIG. 13 engaged with the sampling valve of FIG. 12A.

FIG. 15 is a cross-section view of the valve 600 and the actuator 700 illustrating additional details that may be associated with some embodiments. In operation, the valve 600 may be coupled to a collection fitting, such as the collection fitting 206, the collection fitting 306, the collection fitting 406, or collection fitting 506, for example. In an illustrative embodiment, the valve 600 may be coupled to the container union 222 of the connector 214 of the collection fitting 206. In another illustrative embodiment, the valve 600 may be coupled to the third arm 309 of the tee-fitting 308 of the collection fitting 306. In still another illustrative embodiment, the valve 600 may be coupled to the third arm 426 of the tee-fitting 408 of the collection fitting 406. In yet another illustrative embodiment, the valve 600 may be coupled to the third arm 526 of the tee-fitting 508 of the collection fitting 506.

The actuator 700 may be coupled to a specimen container, such as a vial, a graduated cylinder, or a bottle, for example. In some embodiments, the actuator 700 may be coupled to the specimen container 250, for example. In other embodiments, the actuator 700 may be coupled to the specimen container 352, for example. As shown in FIG. 15, the protrusion 704 of the actuator 700 may be inserted into the first end 604 of the valve 600 so that an end of the protrusion 704 contacts the ball 610. The union of the actuator 700 may be coupled to the union of the valve 600 causing the protrusion 704 to push the ball 610 into the valve housing 602, exerting the actuator force and compressing the valve spring 608 against the spring plate 614. In this manner, a fluid path may be created through the valve 600 and the actuator 700, providing a fluid path from a collection fitting, such as the collection fitting 406, for example, to a specimen container. If the specimen container is full, the actuator 700 may be uncoupled from the valve 600, and the protrusion 704 may be removed from the valve 600, allowing the valve spring 608 to move the ball 610 into sealing engagement with the retainer ring 612. In some embodiments, the spring force of the valve spring 608 may be sufficient to seal the ball 610 against the retainer ring 612, thereby preventing fluid communication through the valve 600 if there is no actuator 700 present.

If the valve 600 is coupled to the third arm 426 of the collection fitting 406, for example, the valve 600 may permit fluid communication between a dressing and a fluidly coupled reduced-pressure source through the lumen 412 and the lumen 413. In some embodiments, if the ball 610 is in contact with the retainer ring 612, the lumen 413 and the lumen 412 may fluidly communicate in a space of the valve housing 602 between the ball 610 and the second end 606. In this manner, the valve 600 and the actuator 700 may allow for sampling of fluid, including liquids from the tissue site, without stopping the application of reduced-pressure therapy.

Figure 16:
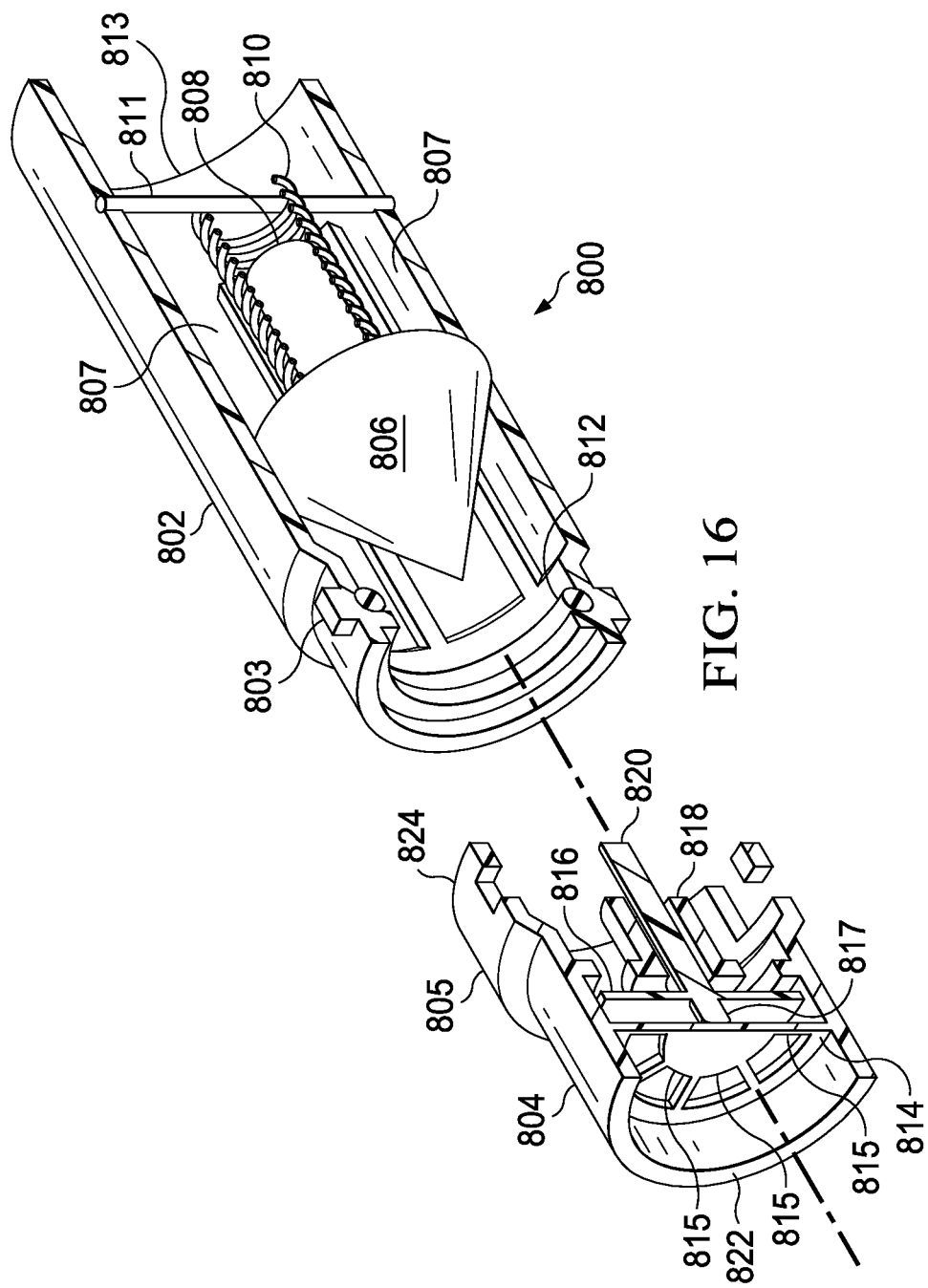
FIG. 16 is a perspective cross-sectional view of another example embodiment of a sampling valve that may be used with the tee fitting of FIG. 10.

FIG. 16 is a perspective cross-sectional view of a valve assembly 800 that may be used in some embodiments of a collection fitting, such as the collection fitting 206, the collection fitting 306, the collection fitting 406, or collection fitting 506, for example. The valve assembly 800 may include a valve housing 802 and an actuator housing 804. The valve housing 802 may be a tubular member. A first end of the valve housing 802 may include a union 803. A second end 813 of the valve housing 802 may be opposite the union 803. The valve housing 802 may include a plurality of passages 807 formed in an inner diameter wall of the valve housing 802 and extending a portion of an axial length of the valve housing 802 between the union 803 and the second end 813.

A valve member 806 may be disposed in the valve housing 802. The valve member 806 may be a conical member having a narrow end disposed proximate to the union 803. A wider end of the valve member 806, opposite the narrow end, may be disposed opposite the union 803 and may have a diameter substantially equivalent to the inner diameter of the valve housing 802 proximate to the union 803. The valve member 806 may include a cylindrical member 808 coupled to an end of the valve member 806. In some embodiments, the cylindrical member 808 may be coupled to the wider end of the valve member 806 and extend away from the union 803. A valve spring 810 may circumscribe the cylindrical member 808 so that a first end of the valve spring 810 may rest against the wider end of the valve member 806 and a second end of the valve spring 810 may be coupled to a retainer bar 811 that extends across the valve housing 802. The valve spring 810 may bias the valve member 806 towards the union 803.

The retainer bar 811 may be a cylindrical member having opposing ends coupled to the valve housing 802. In some embodiments, the retainer bar 811 may be coupled proximate to ends of the passages 807. A diameter of the retainer bar 811 may be sized to permit the retainer bar 811 to pass through the end of the valve spring 810. In addition, the diameter of the retainer bar 811 may be sized to create a gap between the cylindrical side of the retainer bar 811 and the inner diameter surface of the valve housing 802. The union 803 may include an O-ring 812 disposed on an inner diameter of the union 803. In some embodiments, the valve member 806 may be pressed against the O-ring 812 to seal the interior of the valve housing 802 to the valve member 806 and prevent fluid communication through the valve housing 802. The position may also be referred to as a closed position.

The actuator housing 804 may be a tubular member having a first end 822 and a second end 824. The second end of the actuator housing 804 may include a union 805. The union 805 may be configured to be coupled to the union 803 of the valve housing 802. The actuator housing 804 may include a retainer plate 814. The retainer plate 814 may have peripheral portions coupled to an inner diameter of the actuator housing 804. The retainer plate 814 may include a plurality of passages 815 circumferentially disposed around the retainer plate 814. The passages 815 may extend through the retainer plate 814, permitting fluid communication through the retainer plate 814. In some embodiments, the retainer plate 814 may have a dome-like shape. In other embodiments, the retainer plate 814 may be flat.

A baffle 816 having a boss 817 may be disposed in the actuator housing 804. The baffle 816 may be positioned between the retainer plate 814 and the union 805. The baffle 816 may be circular and have an outer diameter that is less than the inner diameter of the actuator housing 804 so that there may be a gap between the outer diameter of the baffle 816 and the inner diameter of the actuator housing 804. The boss 817 may be coupled to a first side of the baffle 816, and the boss 817 may rest on the retainer plate 814 to separate the retainer plate 814 and the baffle 816.

A pillar 820 may be coupled to the baffle 816 opposite the boss 817. In some embodiments, the pillar 820 may be a cylindrical member extending away from the baffle 816 toward the union 805. In some embodiments, the pillar 820 may have a diameter less than the inner diameter of the actuator housing 804 so that there may be a fluid path between the pillar 820 and the actuator housing 804. The pillar 820 may have a length such that an end of the pillar 820 may be proximate to the end of the union 805. In some embodiments, the pillar 820 may extend beyond the end of the union 805. In other embodiments, the end of the pillar 820 may be adjacent to the end of the union 805.

The actuator housing 804 may also include a guide member 818 coupled proximate to the union 805. The guide member 818 may be a tubular member having a length less than a length of the pillar 820. The guide member 818 may have an inner diameter greater than the outer diameter of the pillar 820. The pillar 820 may pass through the guide member 818. The pillar 820 may move radially within the guide member 818, but the guide member 818 may at least partially limit the radial movement of the pillar 820.

In operation, the valve housing 802 may be coupled to a collection fitting. In some embodiments, the valve housing 802 may be coupled to the container union 222 of the connector 214 of the collection fitting 206. In other embodiments, the valve housing 802 may be coupled to the third arm 309 of the tee-fitting 308 of the collection fitting 306. In still other embodiments, the valve housing 802 may be coupled to the third arm 426 of the tee-fitting 408 of the collection fitting 406. In yet other embodiments, the valve housing 802 may be coupled to the third arm 526 of the tee-fitting 508 of the collection fitting 506. The actuator housing 804 may be coupled to a specimen container, such as a vial, a graduated cylinder, or a bottle, for example. In some embodiments, the actuator housing 804 may be coupled to the specimen container 250 of FIG. 7. In other embodiments, the actuator housing 804 may be coupled to the specimen container 352 of FIG. 8A, for example.

Reduced pressure may be applied to a tissue site through the collection fitting. If no specimen container is present, fluid communication between the tissue site and the reduced-pressure source may occur between the valve member 806 and the second end 813 of the valve housing 802. For example, fluid communication may occur between the lumen 312 and the lumen 313 of the collection fitting 306 through the valve housing 802. If a sample is desired, the actuator housing 804, having a specimen container coupled to the first end 822, may be coupled to the valve housing 802. For example, the union 805 may be coupled to the union 803 of the valve housing 802. In response, the pillar 820 may contact the narrower end of the valve member 806, forcing the valve member 806 into the interior of the valve housing 802 and compressing the valve spring 810. This may place the valve assembly 800 in an open position. In response, fluid may flow past the valve member 806 through the passages 807 around the baffle 816 through the retainer plate 814 and into the specimen container. If the specimen container contains a desired amount of fluid, the union 805 and the union 803 may be uncoupled and the valve spring 810 may exert a counterforce proportional to a spring constant of the valve spring 810 and the amount the valve spring 810 was compressed, forcing the valve member 806 outwards into contact with the O-ring 812 and sealing the valve housing 802. If the valve member 806 is sealed to the O-ring 812 and the first end 822, the valve assembly 800 may be in a closed position that prevents further fluid communication with the specimen container.

Bypass Switch

Figure 17:
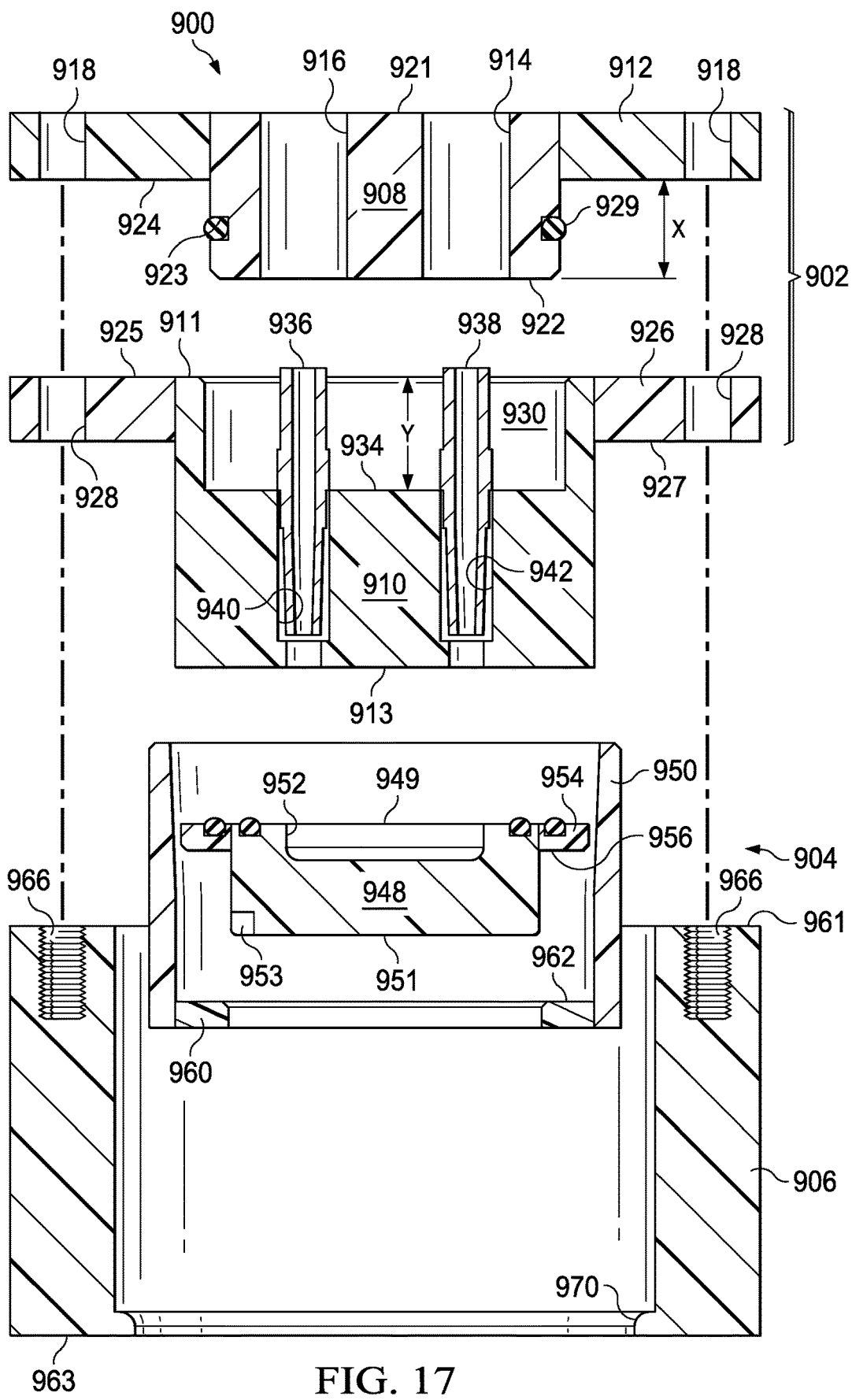
FIG. 17 is an exploded cross-sectional view of another example embodiment of a collection fitting that may be associated with some embodiments of the reduced-pressure therapy system of FIG. 1.

FIG. 17 is a sectional exploded view of a collection fitting 900 that may be used with a reduced-pressure therapy system, such as the reduced-pressure therapy system 100. The collection fitting 900 may be an example embodiment of the collection fitting 106. As shown in FIG. 17, the collection fitting 900 may include a head unit 902, a bypass switch 904, and a device housing 906. The head unit 902 may include a cap 908 and a switch fitting 910. The cap 908 may be a cylindrical body having a first end 921 and a second end 922. The cap 908 may have a flange 912 coupled to the first end 921 and extending outwardly from the cylindrical body of the cap 908. The cap 908 may have a first bore 916 and a second bore 914. The first bore 916 may extend through the cap 908 from the first end 921 to the second end 922, permitting fluid communication through the cap 908. Similarly, the second bore 914 may extend through the cap 908 from the first end 921 to the second end 922, permitting fluid communication through the second bore 914.

The flange 912 of the cap 908 may include one or more bores 918 disposed proximate to peripheral portions of the flange 912. The bores 918 may extend through the flange 912. The flange 912 may form a shoulder 924 that extends from the cap 908 to a peripheral portion of the flange 912. The cap 908 may have a length X that extends from the shoulder 924 to the second end 922. In some embodiments, the shoulder 924 may be an annular member. In some embodiments, the cap 908 may have an annular recess 923 proximate to the second end 922. The annular recess 923 may receive a sealing member 929, for example, an O-ring, permitting the cap 908 to be sealed to an adjoining member.

The switch fitting 910 may be a cylindrical body having a first end 911, a second end 913, and a cavity 930. The cavity 930 may be formed in the first end 911 proximate to a center of the first end 911 and extend into the switch fitting 910. In some embodiments, the cavity 930 may have an inner wall 934 forming a bottom of the cavity 930. In some embodiments, the cavity 930 may have a depth Y extending from the first end 911 of the switch fitting 910 to the inner wall 934. In some embodiments, the cavity 930 may have a generally cylindrical shape. In other embodiments, the cavity 930 may have a cuboid, pyramidal, conical, spherical, or amorphous shape.

The switch fitting 910 may further have a first passage 940 and a second passage 942. The first passage 940 and the second passage 942 may each open into the cavity 930 and extend through the switch fitting 910 from the cavity 930 to the second end 913. In some embodiments, the switch fitting 910 may include a first nipple 936 positioned within the first passage 940 and extending outwardly into and through the cavity 930. In some embodiments, the first nipple 936 may have a wider portion disposed within the first passage 940 and a narrower portion extending into and through the cavity 930. The first nipple 936 may be coupled to the first passage 940, such as with adhesives, fasteners, or an interference fit, for example. In some embodiments, an outer diameter of the first nipple 936 may be fluidly sealed to the first passage 940.

The switch fitting 910 may also include a second nipple 938 positioned within the second passage 942 and extending outwardly from the second passage 942 into and through the cavity 930. In some embodiments, the second nipple 938 may have a wider portion disposed within the second passage 942 and a narrower portion extending into and through the cavity 930. The second nipple 938 may be coupled to the second passage 942, such as with adhesives, fasteners, or an interference fit, for example. In some embodiments, an outer diameter of the second nipple 938 may be sealed to the second passage 942. Both the first nipple 936 and the second nipple 938 may extend upward from the inner wall 934 of the cavity 930. The first nipple 936 may be in fluid communication with the first passage 940, and the second nipple 938 may be in fluid communication with the second passage 942. The first nipple 936 and the second nipple 938 may each have a fluid path extending a length of the respective nipple.

The switch fitting 910 may have a flange 926 coupled to the first end 911 proximate to the cavity 930. The flange 926 may extend outwardly from the switch fitting 910. In some embodiments, the flange 926 may form a shoulder 927 and a shoulder 925, each extends between the cylindrical body of the switch fitting 910 and a peripheral portion of the flange 926. In some embodiments, the flange 926 may include bores 928 positioned proximate to peripheral portions of the flange 926. The bores 928 may extend through the flange 926.

In some embodiments, the head unit 902 may include both the cap 908 and the switch fitting 910. In other embodiments, the switch fitting 910 may not include the first nipple 936 and the second nipple 938. In still other embodiments, the head unit 902 may include the switch fitting 910 without the cap 908.

The bypass switch 904 may include a switch 948 and a switch retainer 950. The switch 948 may be a cylindrical member having a flange 954 coupled to a first end 949 of the switch 948. The flange 954 may extend outwardly from the switch 948 and may include a shoulder 956. The switch 948 may further include a bypass passage 952 formed in the first end 949 of the switch 948. The bypass passage 952 may recess into the first end 949 of the switch 948 and may have a length such that a first end of the bypass passage 952 may be disposed adjacent to the first passage 940 and a second end of the bypass passage 952 may be disposed adjacent to the second passage 942 if the collection fitting 900 is assembled. In some embodiments, the switch 948 may have annular recesses disposed in the flange 954 that may receive annular sealing members, for example, O-rings, to seal the switch 948 to the switch fitting 910. In some embodiments, the switch 948 may include a keyhole 953 formed in a second end 951 of the switch 948. The keyhole 953 may be disposed on an outer diameter portion of the second end 951 of the switch 948. In other embodiments, the keyhole 953 may be disposed on other portions of the second end 951 of the switch 948.

The switch retainer 950 may be a tubular member having a length greater than a length of the switch fitting 910. The switch retainer 950 may also have a flange 960 coupled to a lower end of the switch retainer 950. The flange 960 may be an annular flange and extend inwardly from an inner surface of the switch retainer 950. The flange 960 may form a shoulder 962 which is annular and that may have a width that is substantially equivalent to the width of the shoulder 956 of the flange 954 of the switch 948. In some embodiments, the shoulder 962 may be configured to receive the shoulder 956 so that the shoulder 962 may contact the shoulder 956. In some embodiments, the switch retainer 950 may have an inner diameter such that the outer diameter of the flange 954 may fit within the switch retainer 950, and the cylindrical portion of the switch fitting 910 may have a diameter substantially equal to the inner diameter of the switch retainer 950.

The device housing 906 may be a tubular member having a first end 961 and a second end 963. The device housing 906 may have one or more bores 966 disposed circumferentially around the first end 961 of the device housing 906. In some embodiments, the bores 966 may be threaded to receive a threaded member within the bores 966. The device housing 906 may have an inner diameter greater than the outer diameter of the switch retainer 950, the switch fitting 910, and the cap 908 so that portions of the above-described members may fit within the tubular member of the device housing 906. The device housing 906 may have a detent 970 on an inner diameter surface of the device housing 906 proximate to the second end 963. In some embodiments, the detent 970 may be an annular member. In other embodiments, the detent 970 may extend a portion of an arcuate distance of the inner diameter of the device housing 906.

Figure 18A:
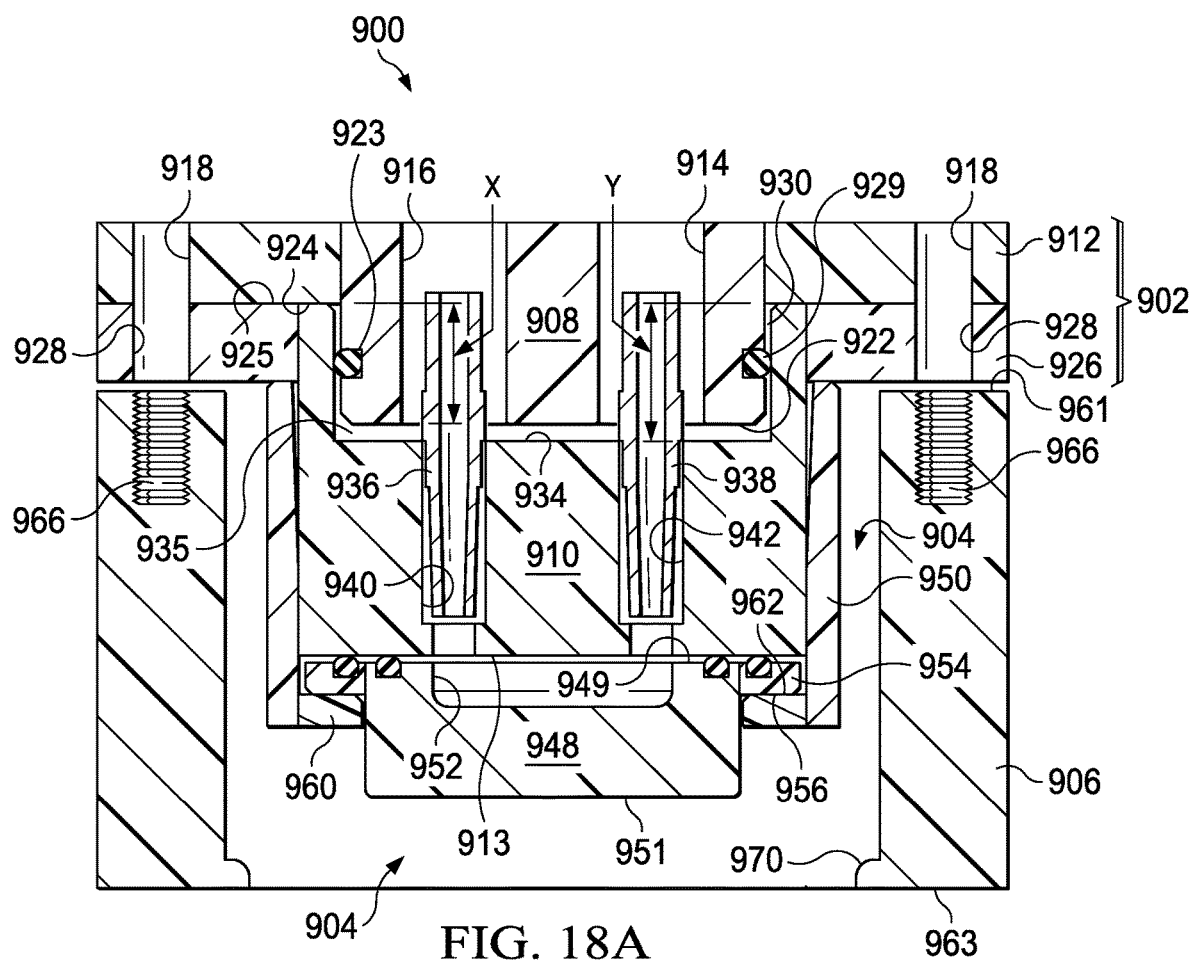
FIG. 18A is a cross-sectional view of the assembled collection fitting of FIG. 17 in a bypass position.

FIG. 18A is a sectional view of the collection fitting 900 illustrating additional details that may be associated with some embodiments. The cap 908 may be coupled to the switch fitting 910 so that the cap 908 may fit within the cavity 930 of the switch fitting 910. The shoulder 925 of the flange 926 may be in contact with the shoulder 924 of the flange 926. The bores 918 of the flange 912 may be substantially aligned with the bores 928 of the flange 926. The first nipple 936 and the second nipple 938 may pass into the first bore 916 and the second bore 914, respectively.

As may be seen in FIG. 18A, the distance X of the cap 908 between the flange 912 and the second end 922 is less than the depth Y of the cavity 930. If the cap 908 is coupled to the switch fitting 910, a gap 935 may be formed between the inner wall 934 of the cavity 930 and the second end 922 of the cap 908. The gap 935 may allow fluid communication between the first bore 916 and the second bore 914.

The switch 948 may be positioned within the switch retainer 950 so that the shoulder 956 of the flange 954 may be in contact with and rest on the shoulder 962 of the flange 960. The contact area between the shoulder 956 of the flange 954 and the shoulder 962 of the flange 960 may form a bearing, for example a plain bearing, that may permit the shoulder 956 and the shoulder 962 to slip relative to one another if a rotational force is applied to the switch 948. In other embodiments, the bearing may be a rolling element bearing, a fluid bearing, a magnetic bearing, or a flexure bearing, for example.

The switch retainer 950, having the switch 948 disposed therein, may be coupled to the switch fitting 910. In some embodiments, the cylindrical portion of the switch fitting 910 may be inserted into the switch retainer 950 until the second end 913 of the switch fitting 910 may contact the first end 949 of the switch 948. The switch retainer 950 may be secured to the switch fitting 910 by a suitable means, such as by welding, with adhesives, with fasteners, or with an interference fit, for example. The flange 960 may hold the switch 948 against the second end 913 of the switch fitting 910. The bypass switch 904 and the head unit 902 may be inserted into the interior portion of the device housing 906. In some embodiments, the bores 918 of the flange 912, the bores 928 of the flange 926, and the bores 966 of the device housing 906 may be substantially aligned. Fasteners may then be fitted through the bores 918, the bores 928, and the bores 966 to secure the head unit 902, bypass switch 904, and the device housing 906 to each other.

The switch 948 may move relative to the switch fitting 910 and the switch retainer 950. For example, the switch 948 may rotate coaxially relative to the switch fitting 910 and the switch retainer 950. As shown in FIG. 18A, the switch 948 may be in a bypass position. In the bypass position, the first end of the bypass passage 952 may be in fluid communication with the first nipple 936, and the second end of the bypass passage 952 may be in fluid communication with the second nipple 938. Fluid provided to the first nipple 936 may flow to the second nipple 938 through the bypass passage 952. Similarly, fluid provided to the second nipple 938 may flow to the first nipple 936 through the bypass passage 952.

Figure 18B:
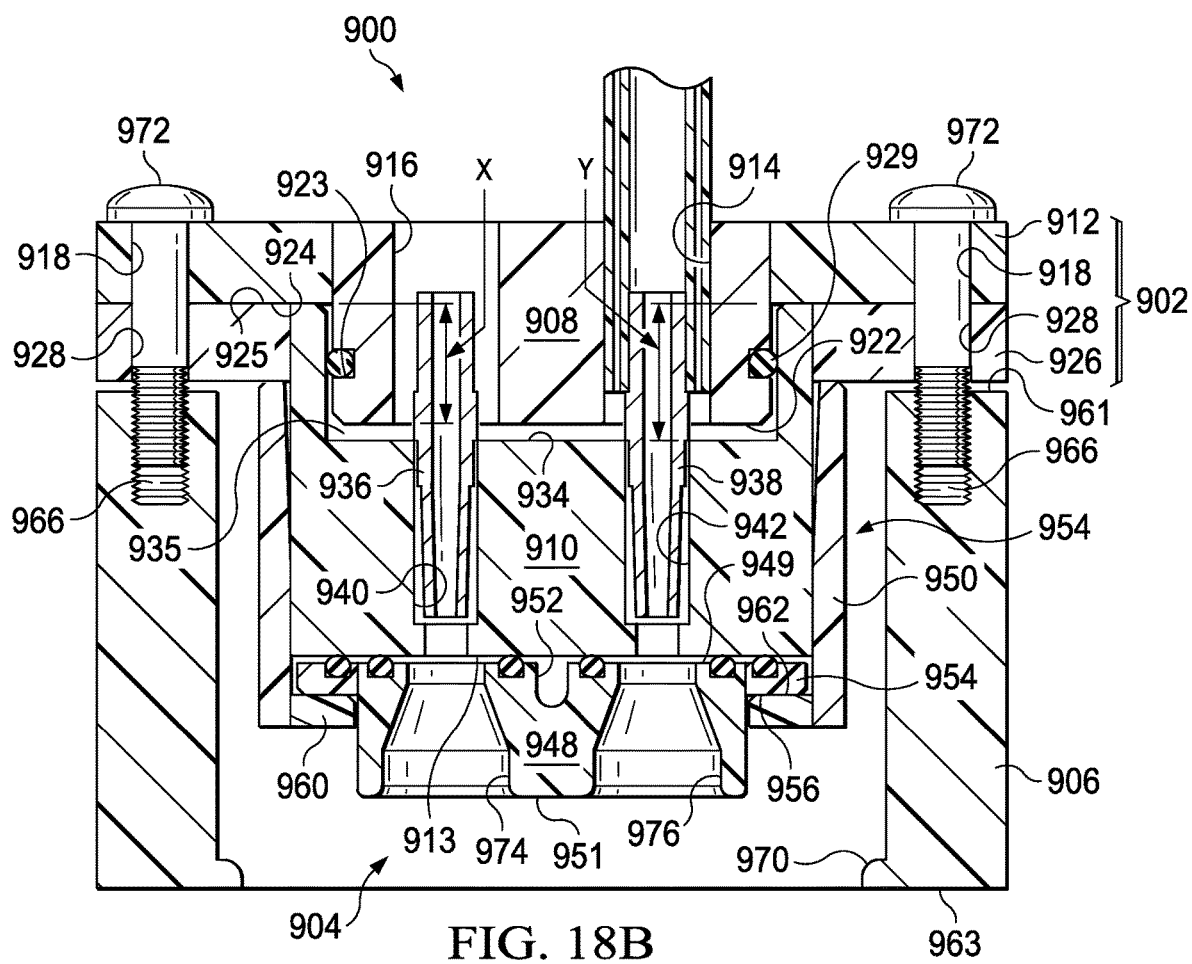
FIG. 18B is a cross-sectional view of the assembled collection fitting of FIG. 17 in a sampling position.

FIG. 18B is a sectional assembly view of the collection fitting 900 illustrating additional details that may be associated with some embodiments. In some embodiments, the collection fitting 900 may include fasteners 972 securing the head unit 902 to the device housing 906. The fasteners 972 may be passed through the bores 918 of the flange 912, the bores 928 of the flange 926, and thread to the bores 966 of the device housing 906. In some embodiments, the bypass switch 904 has been placed in a sampling position. In the sampling position, the switch 948 may further include a first passage 974 and a second passage 976. The first passage 974 and the second passage 976 may extend through the switch 948. If in the sampling position, the first passage 974 may be substantially aligned with the first passage 940, and the second passage 976 may be substantially aligned with the second passage 942. And the bypass passage 952 may not be in fluid communication with the first passage 940 or the second passage 942 of the switch fitting 910.

Figure 19:
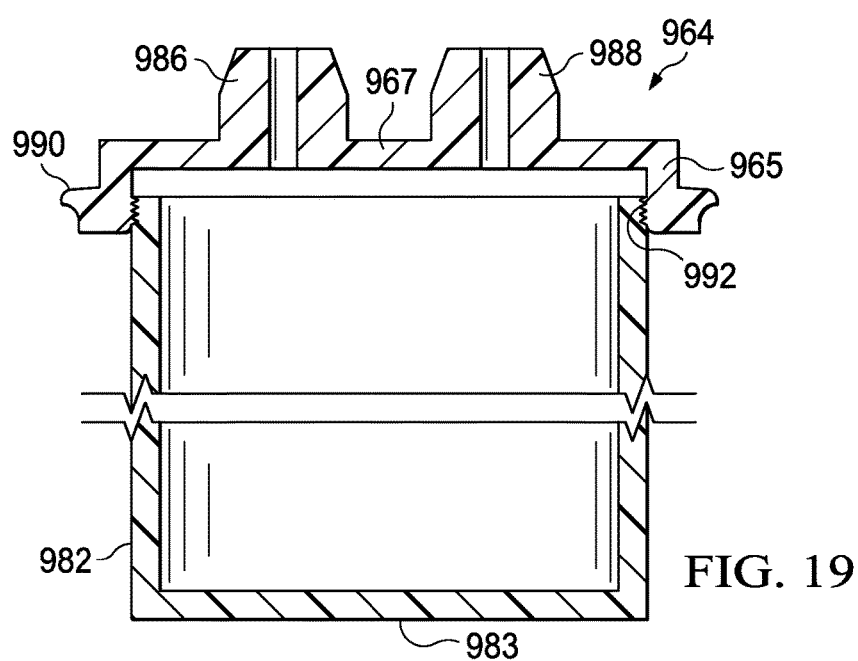
FIG. 19 is a cross-sectional view of a specimen container that may be used with a collection fitting such as the illustrative collection fitting of FIG. 17.

FIG. 19 is a cross-sectional view of a specimen container 982 that may be used with the collection fitting 900 of FIG. 17, FIG. 18A, and FIG. 18B. The specimen container 982 may be a tubular member having a closed end formed by a bottom wall 983. The specimen container 982 may also include a cap 964 that may be coupled to the open end of the specimen container 982 opposite the bottom wall 983. In some embodiments, the specimen container 982 may be secured to the cap 964 through a pair of mating threads 992, for example. In other embodiments, the specimen container 982 and the cap 964 may be coupled through welding, adhesives, or with an interference fit, for example.

The cap 964 may be a tubular body having a side wall 965 and a top wall 967. In some embodiments, the side wall 965 may be annular. The top wall 967 may have peripheral portions coupled to an end of the side wall 965 to form the cap 964. The cap 964 may further include a first nipple 986 and a second nipple 988. The first nipple 986 and the second nipple 988 may be cylindrical members coupled to the top wall 967 of the cap 964 and having a fluid passage extending a length of the cylindrical member through the top wall 967 of the cap 964. In some embodiments, the first nipple 986 and the second nipple 988 may have frustoconical portions on an end of the first nipple 986 and the second nipple 988 opposite the top wall 967. The first nipple 986 may have a size and shape such that the first nipple 986 may be inserted into the first passage 974 of the switch 948. Similarly, the second nipple 988 may have a size and shape such that the second nipple 988 may be inserted into the second passage 976 of the switch 948.

The side wall 965 of the cap 964 may have a detent 990 formed on an exterior surface of the side wall 965. In some embodiments, the detent 990 may extend outwardly from the side wall 965 of the cap 964. In some embodiments, the detent 990 may be an annular member. In some embodiments, the detent 990 may be configured to mate with the detent 970 of the device housing 906.

Figure 20:
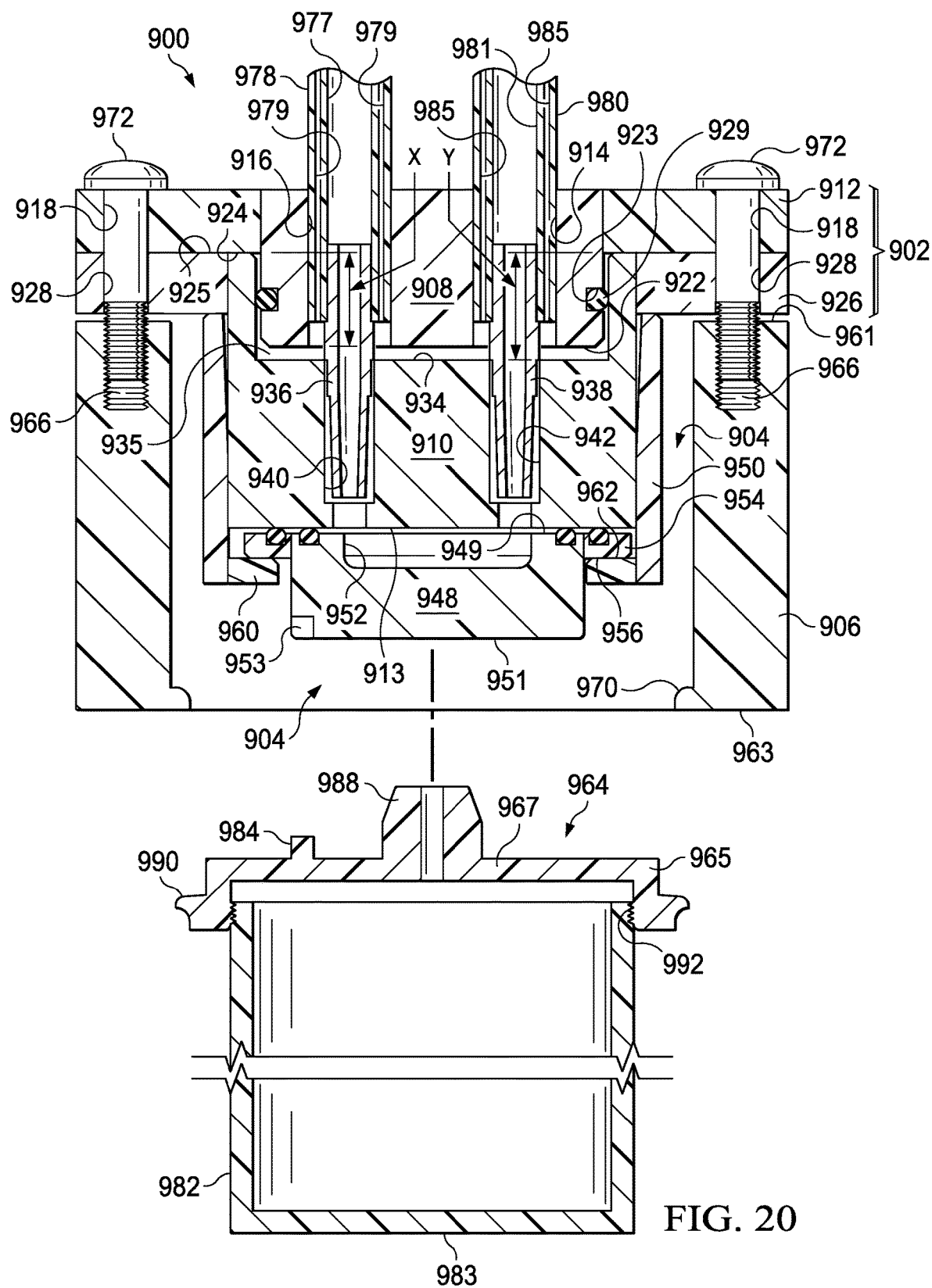
FIG. 20, FIG. 21, and FIG. 22 are cross-sectional views illustrating the use of the illustrative collection fitting of FIG. 17 with the illustrative specimen container of FIG. 19.
Figure 21:
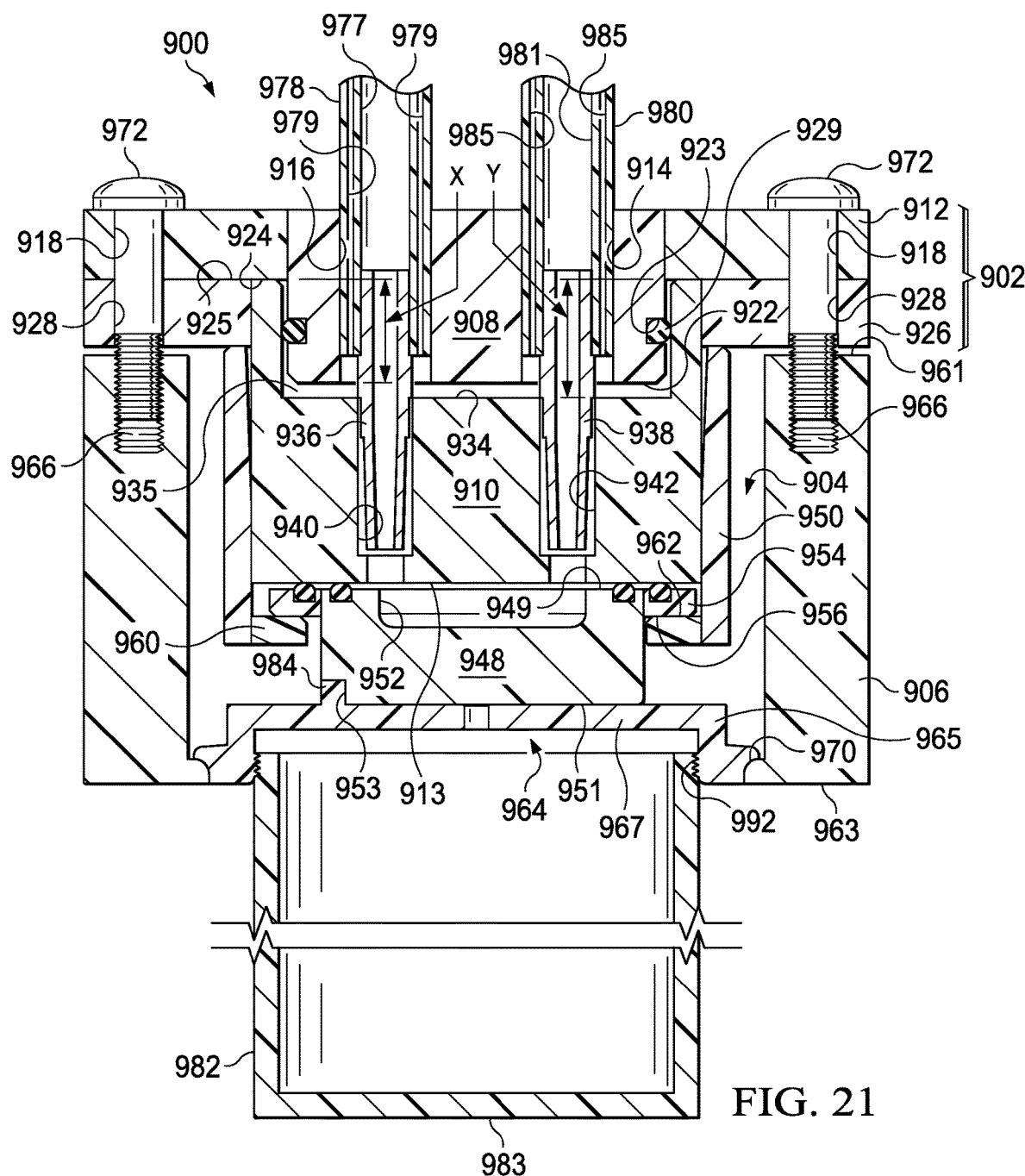
Figure 22:
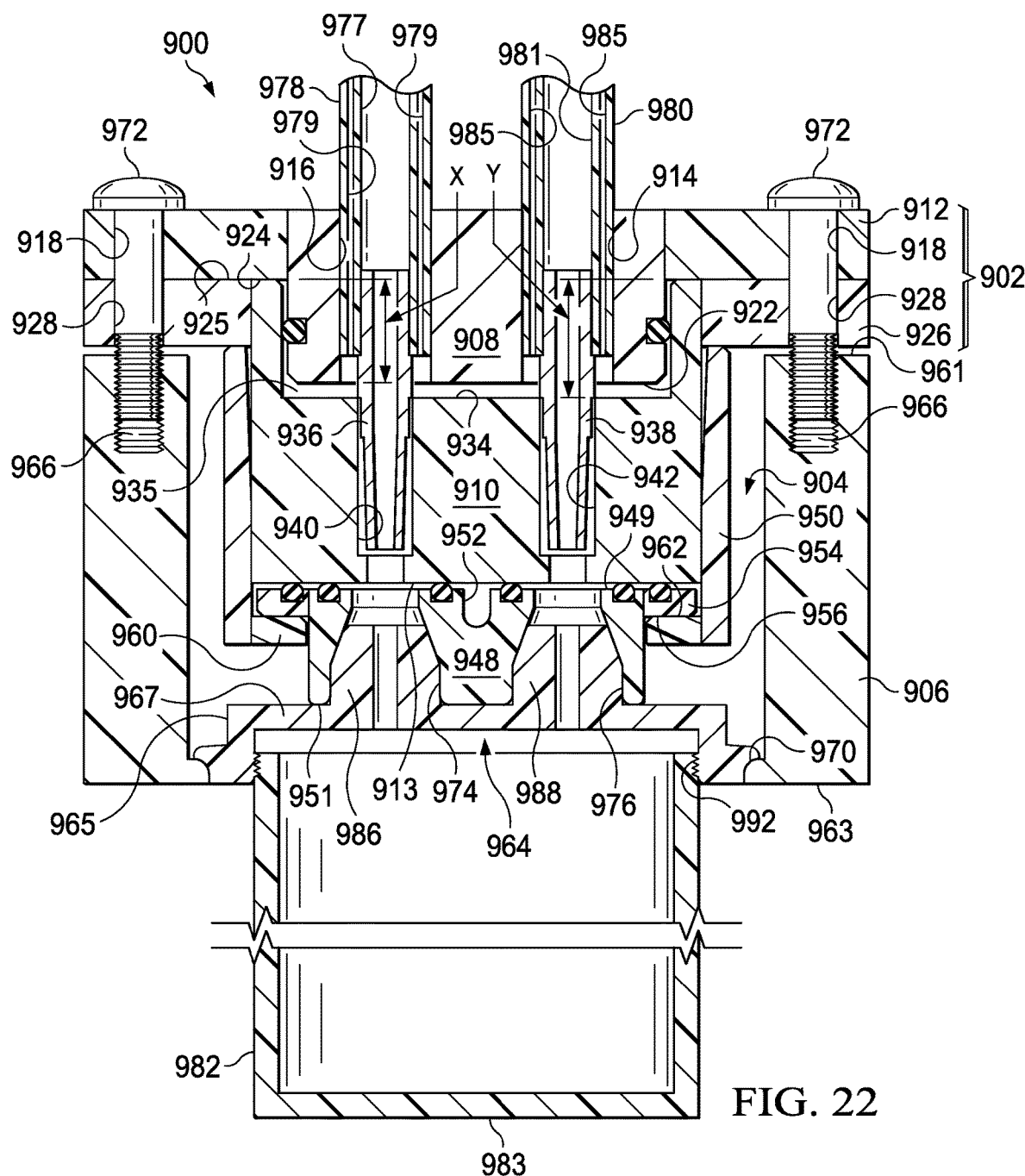

FIG. 20, FIG. 21, and FIG. 22 are schematic cross-sectional views of the collection fitting 900 and the specimen container 982 illustrating additional details that may be associated with some embodiments. In some embodiments, the cap 964 may include a key 984. The key 984 may be formed on a surface of the top wall 967 opposite the side wall 965 so that the key 984 may protrude from the top wall 967. In some embodiments, the key 984 may be sized to fit within the keyhole 953 of the switch 948.

As shown in FIG. 20, a first tube 978 may be coupled to the collection fitting 900, for example, to the first nipple 936. Similarly, a second tube 980 may be coupled to the collection fitting 900, for example, to the second nipple 938. In some embodiments, the first tube 978 may be a multi-lumen tube having a central lumen 977 disposed in a center of the first tube 978 and one or more peripheral lumens 979 disposed about a periphery of the first tube 978. Similarly, the second tube 980 may be a multi-lumen tube having a central lumen 981 disposed in a center of the second tube 980 and one or more peripheral lumens 985 disposed about a periphery of the second tube 980.

The first tube 978 may be secured to the first nipple 936 so that the central lumen 977 of the first tube 978 may be in fluid communication with the first passage 940 through the first nipple 936. In some embodiments, an end of the first nipple 936 may be inserted into the central lumen 977 of the first tube 978. In some embodiments, the first nipple 936 may have a frustoconical shape having the narrower portion separated from the inner wall 934 of the cavity 930. An increasing diameter of the first nipple 936 may limit the amount the first nipple 936 may be inserted into the first tube 978. In this manner, an end of the first tube 978 may be separated from the inner wall 934 of the cavity 930. As a result, the central lumen 977 of the first tube 978 may be in fluid communication through the first nipple 936, and the peripheral lumens 979 of the first tube 978 may be in fluid communication with the gap 935. In some embodiments, a portion of the outer diameter surface of the first tube 978 may seal to the first bore 916.

The second tube 980 may be secured to the second nipple 938 so that the central lumen 981 of the second tube 980 may be in fluid communication with the second passage 942 through the second nipple 938. In some embodiments, an end of the second nipple 938 may be inserted into the central lumen 981 of the second tube 980. In some embodiments, the second nipple 938 may have a frustoconical shape having the narrower portion separated from the inner wall 934 of the cavity 930. An increasing diameter of the second nipple 938 may limit the amount the second nipple 938 may be inserted into the second tube 980. In this manner, an end of the second tube 980 may be separated from the inner wall 934 of the cavity 930. As a result, the central lumen 981 of the second tube 980 may be in fluid communication through the second nipple 938, and the peripheral lumens 985 of the second tube 980 may be in fluid communication with the cavity 930. In some embodiments, a portion of the outer diameter surface of the second tube 980 may seal to the second bore 914.

The peripheral lumens 979 of the first tube 978 may be in fluid communication with the gap 935 if the first tube 978 is fluidly coupled to the first nipple 936. Similarly, the peripheral lumens 985 of the second tube 980 may be in fluid communication with the gap 935 if the second tube 980 is fluidly coupled to the second nipple 938. In this manner, the peripheral lumens 979 and the peripheral lumens 985 may be fluidly coupled through the gap 935.

As shown in FIG. 20, the collection fitting 900 may be disposed with the bypass switch 904 in the bypass position so that the bypass passage 952 may be in fluid communication with the first passage 940 and the second passage 942. If the bypass switch 904 is in the bypass position, the central lumen 977 of the first tube 978 and the central lumen 981 of the second tube 980 are fluidly coupled. In this manner, fluid and reduced pressure may be communicated through the bypass switch 904 between the tissue site and the reduced-pressure source or container.

In some embodiments, the first tube 978 may be fluidly coupled to a reduced-pressure source through a container, and the second tube 980 may be fluidly coupled to a tissue site through a dressing. If the reduced-pressure source is operated, the reduced-pressure source may supply reduced-pressure to the first tube 978 through the central lumen 977 of the first tube 978. The reduced pressure may be communicated from the first tube 978 to the second tube 980 through the bypass passage 952. The second tube 980 may communicate the reduced pressure to the dressing through the central lumen 981 of the second tube 980.

In some embodiments, the reduced-pressure source may provide feedback regarding the provision of reduced pressure therapy by determining a pressure at the tissue site. The reduced-pressure source may have one or more pressure sensors fluidly coupled to the peripheral lumens 979 of the first tube 978. The peripheral lumens 979 of the first tube 978 may be in fluid communication with the peripheral lumens 985 of the second tube 980 through the gap 935, and the peripheral lumens 985 of the second tube 980 may further be in fluid communication with the tissue site through the dressing. The pressure at the tissue site may be communicated to the pressure sensors of the reduced-pressure source along this path, allowing the reduced-pressure source to determine the pressure at the tissue site. In these embodiments, the gap 935 may operate as a sensing bypass to fluidly communicate pressure if the switch 948 is both in the bypass position and in the sampling position.

To take a sample of the liquid from the tissue site, the specimen container 982 may be brought proximate to the device housing 906 of the collection fitting 900. As shown in FIG. 21, the specimen container 982 may be inserted into the collection fitting 900 so that the specimen container 982 engages the bypass switch 904. In some embodiments, the first nipple 986 of the cap 964 may be inserted into the first passage 974 of the switch 948, and the second nipple 988 of the cap 964 may be inserted into the second passage 976 of the switch 948. In some embodiments, the key 984 of the cap 964 may be inserted into the keyhole 953 of the switch 948. The cap 964 may be moved into the device housing 906 until the detent 990 of the cap 964 moves past the detent 970 of the device housing 906, securing the cap 964, and the coupled specimen container 982, to the device housing 906 and the collection fitting 900.

The cap 964 may rotate relative to the device housing 906 while inserted into the device housing 906. The specimen container 982 may be rotated about 90°, rotating the switch 948 through the engaged first nipple 986 and first passage 974 and the second nipple 988 and the second passage 976. In some embodiments, rotational motion may be transferred through the key 984 of the cap 964 and the keyhole 953 of the switch 948. The rotation moves the bypass passage 952 out of fluid communication with the first passage 940 and the second passage 942. As shown in FIG. 22, the rotation also aligns the first passage 974 with the first passage 940 and the second passage 976 with the second passage 942.

Reduced pressure, supplied by the reduced-pressure source may be communicated to the dressing between the central lumens 977, 981 of the first tube 978 and the second tube 980, respectively, through the first passage 974, the second passage 976, and the specimen container 982. As the reduced-pressure draws off fluids, including liquids from the tissue site, the fluids may be communicated through the specimen container 982. The specimen container 982 may fill with liquid from the tissue site for sampling. Once a sufficiently sized sample of fluids has been received by the specimen container 982, the specimen container 982 may be rotated again 90° to bring the bypass passage 952 into fluid communication with the first passage 940 and the second passage 942, allowing fluid communication to occur through the bypass passage 952 as shown in FIG. 20.

Figure 23:
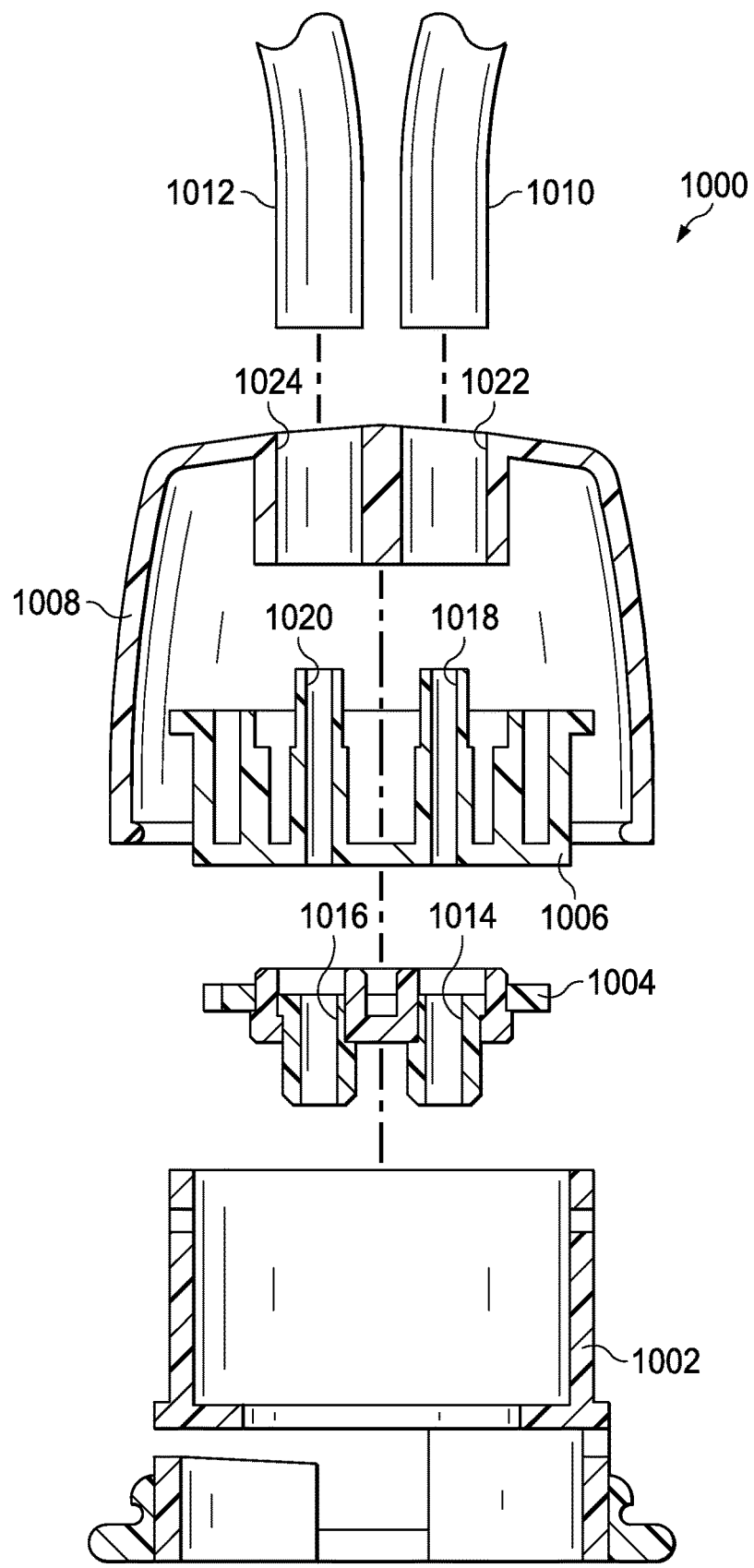
FIG. 23 is an exploded cross-sectional view of another example embodiment of a collection fitting that may be associated with some embodiments of the reduced-pressure therapy system of FIG. 1.

FIG. 23 is a sectional assembly view of a collection fitting 1000 that may be used with a reduced-pressure therapy system, such as the reduced-pressure therapy system 100 of FIG. 1. The collection fitting 1000 may be an example embodiment of the collection fitting 106. The collection fitting 1000 may include a chassis 1002, a switch 1004, a disc cup 1006, and a cap 1008. In some embodiments, the collection fitting 1000 may have a first tube 1010 having a union for coupling to another device and a second tube 1012 having a union for coupling to another device. Generally, the chassis 1002 may be a tubular body having an interior formed by an annular wall. Opposing ends of the chassis 1002 may be open.

The switch 1004 may be a generally disc-like body having a first port 1014 and a second port 1016. The first port 1014 and the second port 1016 may permit fluid communication through the switch 1004. The switch 1004 may be disposed within the chassis 1002 between the open ends of the chassis 1002.

The disc cup 1006 may be a generally cylindrical body and may include a first nipple 1018 and a second nipple 1020. The first nipple 1018 and the second nipple 1020 may permit fluid communication through the disc cup 1006. The disc cup 1006 may also be disposed in the chassis 1002. In some embodiments, the disc cup 1006 may be disposed within the chassis 1002 adjacent to the switch 1004. In some embodiments, the first nipple 1018 may be in fluid communication with the first port 1014 of the switch 1004 if the disc cup 1006 and the switch 1004 are disposed within the chassis 1002. Similarly, the second nipple 1020 may be in fluid communication with the second port 1016 if the disc cup 1006 and the switch 1004 are disposed within the chassis 1002. In other embodiments, the first nipple 1018 and the first port 1014 may not be in fluid communication if the disc cup 1006 and the switch 1004 are disposed within the chassis 1002. Similarly, the second nipple 1020 and the second port 1016 may not be in fluid communication if the disc cup 1006 and the switch 1004 are disposed within the chassis 1002.

The cap 1008 may be a tubular body having an open end and a closed end. The cap 1008 may include a first passage 1022 and a second passage 1024 disposed in the closed end. The first passage 1022 and the second passage 1024 may be elongate members having portions depending into an interior of the cap 1008. In some embodiments, the first passage 1022 and the second passage 1024 may be disposed in a center portion of the closed end of the cap 1008. The cap 1008 may mount to the chassis 1002. In some embodiments, the chassis 1002 may be inserted into the open end of the cap 1008 and coupled to the cap 1008 so that the first passage 1022 may be in fluid communication with the first nipple 1018. Similarly, the second passage 1024 may be in fluid communication with the second nipple 1020. The first passage 1022 and the second passage 1024 may provide a fluid path through the closed end of the cap 1008. The chassis 1002 and the cap 1008 may enclose or partially enclose the switch 1004 and the disc cup 1006.

The first tube 1010 may be a tube having at least one lumen. In some embodiments, the first tube 1010 may be a multi-lumen tube. The first tube 1010 may be coupled to the first passage 1022 of the cap 1008. In some embodiments, the first tube 1010 may be in fluid communication with the first passage 1022 if the first tube 1010 is coupled to the first passage 1022 of the cap 1008.

The second tube 1012 may be a tube having at least one lumen. In some embodiments, the second tube 1012 may be a multi-lumen tube. The second tube 1012 may be coupled to the second passage 1024 of the cap 1008. In some embodiments, the second tube 1012 may be in fluid communication with the second passage 1024 if the second tube 1012 is coupled to the second passage 1024 of the cap 1008.

Figure 24:
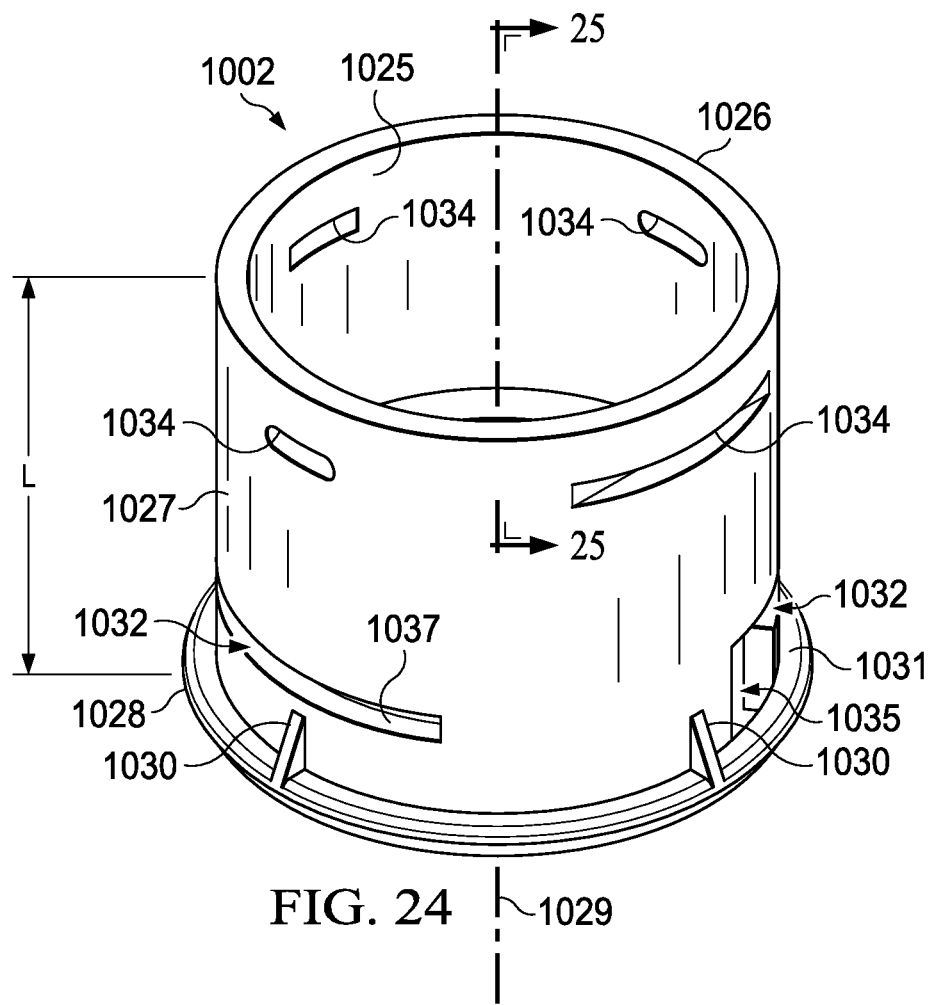
FIG. 24 is a perspective view of an example embodiment of a chassis that may be associated with some embodiments of the collection fitting of FIG. 23.

FIG. 24 is a perspective view of the chassis 1002 illustrating additional details that may be associated with some embodiments. As described above, the chassis 1002 may be a tubular body formed by an annular wall 1026. The annular wall 1026 may have an interior surface 1025, an exterior surface 1027, a circumference, and a length L. The annular wall 1026 may have an axis 1029 passing through a center of the annular wall 1026. The annular wall 1026 may also have an upper end and a lower end. The upper and lower end may be opposite one another and may be considered upper and lower for descriptive purposes relative to the positioning of the chassis 1002 in FIG. 24.

The annular wall 1026 may also include one or more mounting slots 1032 formed in the annular wall 1026. The mounting slot 1032 may pass through the annular wall 1026 from the exterior surface 1027 to the interior surface 1025. The mounting slot 1032 may have an axial portion 1035 that extends from the lower end of the annular wall 1026 parallel to the axis 1029 of the annular wall 1026. The axial portion 1035 of the mounting slot 1032 may extend a distance toward the upper end less than the length L of the annular wall 1026.

The mounting slot 1032 may also include a circumferential portion 1037 extending circumferentially parallel to the circumference of the annular wall 1026. The circumferential portion 1037 of the mounting slot 1032 extends from an end of the axial portion 1035 of the mounting slot 1032. The circumferential portion 1037 of the mounting slot 1032 may extend a circumferential distance less than the circumference of the annular wall 1026. In some embodiments, the circumferential portion 1037 of the mounting slot 1032 may have a wider portion proximate to the union of the circumferential portion 1037 and the axial portion 1035 and a narrower portion proximate to an opposite end of the circumferential portion 1037. In some embodiments, the chassis 1002 may include two mounting slots 1032 that are circumferentially spaced about the annular wall 1026. In other embodiments, the chassis 1002 may have more or fewer mounting slots 1032.

One or more apertures 1034 may be formed in the annular wall 1026. The apertures 1034 may pass through the annular wall 1026 from the exterior surface 1027 to the interior surface 1025 of the annular wall 1026. In some embodiments, the apertures 1034 may be proximate to the upper end of the annular wall 1026. In other embodiments, the apertures 1034 may be adjacent to the upper end of the annular wall 1026. In some embodiments, the apertures 1034 may have an elongated shape including sides parallel to each other and the circumference of the annular wall 1026. The apertures 1034 may also have opposing rounded ends that join to the parallel sides. In some embodiments, the apertures 1034 may be circumferentially spaced around the annular wall 1026. In some embodiments, the apertures 1034 may all be located a same distance from the upper end of the annular wall 1026. In some embodiments, the chassis 1002 includes four apertures 1034. In other embodiments, the chassis 1002 may include more or fewer apertures 1034.

The chassis 1002 may also have a chassis flange 1028. The chassis flange 1028 may be an annular member and may include a shoulder 1031. The chassis flange 1028 may be coupled to the exterior surface 1027 of the annular wall 1026. In some embodiments, the chassis flange 1028 may be coupled to the annular wall 1026 proximate to the lower end of the annular wall 1026. In other embodiments, the chassis flange 1028 may be coupled adjacent to the lower end of the annular wall 1026. As shown in FIG. 24, the chassis flange 1028 may circumscribe the annular wall 1026 adjacent to the mounting slots 1032.

The chassis 1002 may also include one or more gusset plates 1030. The gusset plates 1030 may couple to the shoulder 1031 of the chassis flange 1028. The gusset plates 1030 may further couple to the exterior surface 1027 of the annular wall 1026. The gusset plates 1030 may be circumferentially spaced around the annular wall 1026.

Figure 25:
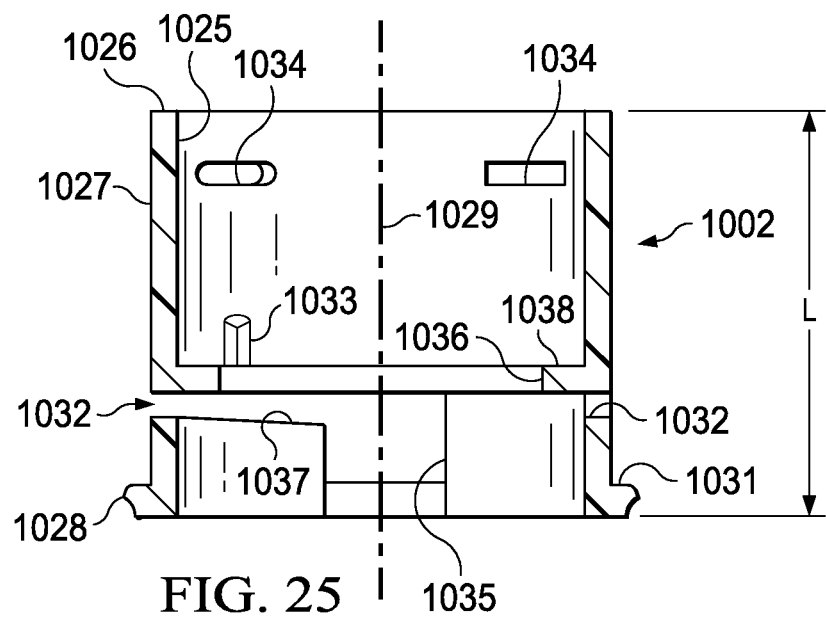
FIG. 25 is a cross-sectional view of the chassis of FIG. 24 taken along line 25-25 of FIG. 24.

FIG. 25 is a cross-sectional view of the chassis 1002 taken along line 25-25 of FIG. 24 illustrating additional details that may be associated with some embodiments. The chassis 1002 may further include a key 1033 and a switch ring 1036. The switch ring 1036 may be an annular member having an outer diameter and an inner diameter. Peripheral portions of the switch ring 1036 may be coupled to the interior surface 1025 of the annular wall 1026. In some embodiments, the switch ring 1036 may be coupled to the annular wall 1026 adjacent to the mounting slots 1032. In other embodiments, the switch ring 1036 may be coupled to the annular wall 1026 proximate to an upper circumferential edge of the mounting slots 1032. The switch ring 1036 may form a shoulder 1038. The shoulder 1038 may be an annular member.

In some embodiments, the key 1033 may be an axial protrusion extending from the shoulder 1038. The key 1033 may extend inwardly from the interior surface 1025 toward the axis 1029 of the annular wall 1026. In some embodiments, the key 1033 may have a width substantially equal to a width of the shoulder 1038. In other embodiments, the key 1033 may have a width less than a width of the shoulder 1038. The key 1033 may have height less than a height of the annular wall 1026 so that the key 1033 may extend from the shoulder 1038 a distance less than the length L of the annular wall 1026. In some embodiments, an end of the key 1033 opposite the shoulder 1038 may be separated from the upper end of the annular wall 1026. In some embodiments, the end of the key 1033 may be separated from a lower edge of the apertures 1034.

Figure 26A:
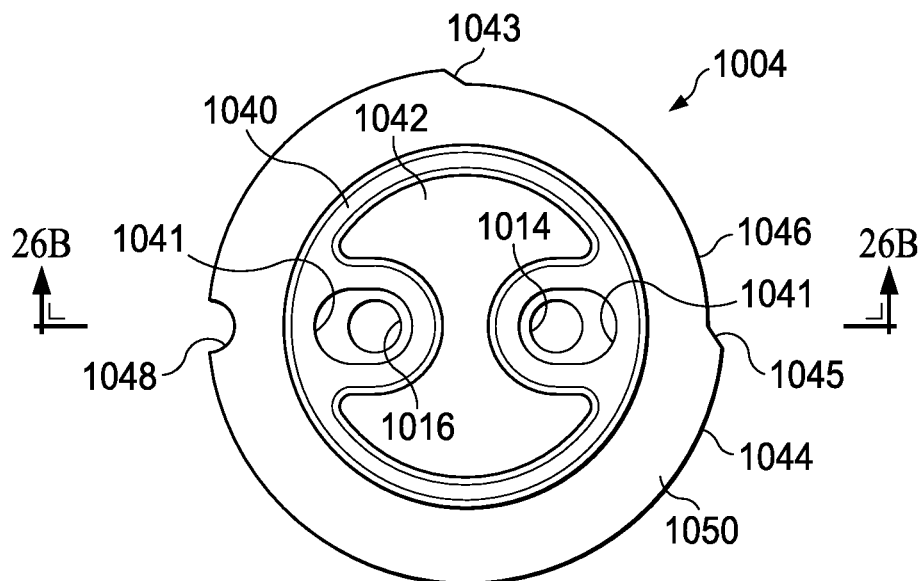
FIG. 26A is a top view of an example embodiment of a bypass switch that may be used with some embodiments of the collection fitting of FIG. 23.

FIG. 26A is a top view of the switch 1004 illustrating additional details that may be associated with some embodiments. The switch 1004 may include an inner base 1040. The inner base 1040 may be a cylindrical body having the first port 1014 and the second port 1016 formed therein. The inner base 1040 may include counterbores 1041 proximate to the first port 1014 and the second port 1016. The counterbores 1041 may have a horizontal dimension larger than the second port 1016 and the first port 1014. The inner base 1040 may further have a bypass passage 1042 formed between the first port 1014 and the second port 1016. In some embodiments, the bypass passage 1042 is a recess formed in a top of the inner base 1040 and may include two semicircular portions on opposing sides of the top of the inner base 1040. The two semicircular portions may be joined by a fluid passage extending between the first port 1014 and the second port 1016 so that the opposing portions of the bypass passage 1042 may be in fluid communication with each other and fluidly isolated from the first port 1014 and the second port 1016.

The switch 1004 may also include a flange 1044 coupled to a center portion of the inner base 1040. The flange 1044 may extend radially outward from the inner base 1040. The flange 1044 may include a shoulder 1050. The shoulder 1050 may be an annular surface. In some embodiments, the flange 1044 may be a generally circular body. In some embodiments, the flange 1044 may include a cut-out 1046. The cut-out 1046 may be a portion of the flange 1044 that recesses radially inward from an outer diameter of the flange 1044. The cut-out 1046 may have an arcuate distance less than a circumference of the flange 1044. In some embodiments, the cut-out 1046 may form a first shoulder 1043 and a second shoulder 1045 on opposite ends of the cut-out 1046. The first shoulder 1043 and the second shoulder 1045 may face each other around a portion of the circumference of the flange 1044. The flange 1044 may also include a notch 1048 formed in the flange 1044. The notch 1048 may have a semicircular shape.

Figure 26B:
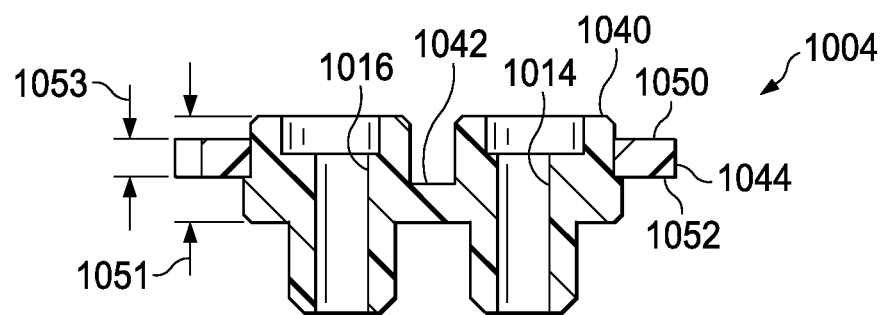
FIG. 26B is a cross-sectional view of the bypass switch of FIG. 26A taken along line 26A-26A of FIG. 26A.

FIG. 26B is a cross-sectional view of the switch 1004 taken along line 26B-26B illustrating additional details that may be associated with some embodiments. The inner base 1040 may have a thickness 1051, and the flange 1044 may have a thickness 1053. In some embodiments, the thickness 1053 may be less than the thickness 1051. The flange 1044 may also include a shoulder 1052. The shoulder 1052 may be an annular member opposite the shoulder 1050. The first port 1014 and the second port 1016 may be substantially tubular bodies depending from the inner base 1040. The first port 1014 and the second port 1016 each have a length greater than a thickness of the inner base 1040 so that the first port 1014 and the second port 1016 may depend from a lower portion of the inner base 1040.

Figure 27:
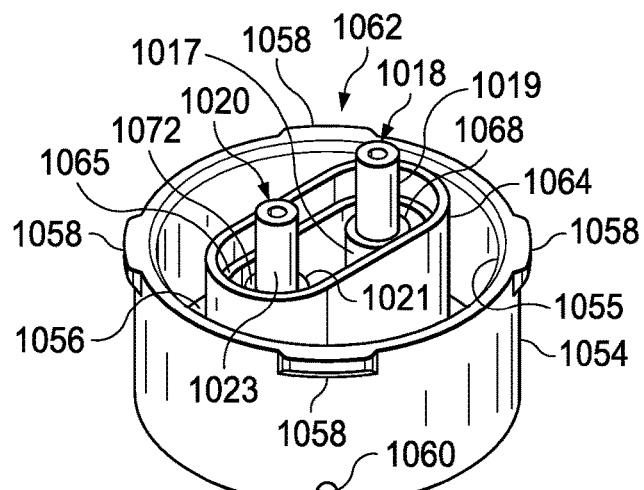
FIG. 27 is a perspective view of an example embodiment of a disc cup that may be used with some embodiments of the collection fitting of FIG. 23.

FIG. 27 is a perspective view of the disc cup 1006 illustrating additional details that may be associated with some embodiments. The disc cup 1006 may include a tubular wall 1054. The tubular wall 1054 may have a bottom wall 1056 coupled to one end of the tubular wall 1054 and an open end 1055 opposite the bottom wall 1056. The tubular wall 1054 may also include a plurality of protrusions 1058. The protrusions 1058 may be coupled to an exterior portion of the tubular wall 1054 proximate to the open end 1055. The protrusions 1058 may be circumferentially spaced around the tubular wall 1054. Each protrusion 1058 may have an arcuate length that is less than a circumference of the tubular wall 1054. The protrusions 1058 protrude radially outward from the tubular wall 1054. The tubular wall 1054 may also include a notch 1060 formed on exterior portion adjacent to the bottom wall 1056. The notch 1060 recesses into the tubular wall 1054.

The disc cup 1006 may also include an inner wall 1064. The inner wall 1064 may have an end coupled to the bottom wall 1056 and may extend upwardly from the bottom wall 1056. In some embodiments, the inner wall 1064 may have a height substantially similar to a height of the tubular wall 1054. In some embodiments, the inner wall 1064 may have a portion extending through the open end 1055. In some embodiments, the inner wall 1064 may be circular and have an interior portion. In the some embodiments, the inner wall 1064 may be ovoid. The inner wall 1064 may have a thickness. In some embodiments, the inner wall 1064 may be partially countersunk so that an end of the inner wall 1064 opposite the bottom wall 1056 may have a shoulder 1065 on an inner dimension of the inner wall 1064. The shoulder 1065 may be an annular member and face the open end 1055. The inner wall 1064 may generally define an interior space that is hollow and may be fluidly separate from an interior space defined by the tubular wall 1054.

The first nipple 1018 may be disposed in the interior portion of the inner wall 1064. The first nipple 1018 may be a generally cylindrical body having a fluid passage extending through the cylindrical body. The first nipple 1018 may have a first portion 1017 having a first diameter and a second portion 1019 having a second diameter. In some embodiments the first diameter may be greater than the second diameter. The first portion 1017 may be coupled to the bottom wall 1056 and extend upwardly therefrom. The second portion 1019 may extend from the first portion 1017 to form a shoulder 1068 where the first portion 1017 and the second portion 1019 join.

The second nipple 1020 may be disposed in the interior portion of the inner wall 1064. The second nipple 1020 may be a generally cylindrical body having a fluid passage extending through the cylindrical body. The second nipple 1020 may have a first portion 1021 having a first diameter and a second portion 1023 having a second diameter. In some embodiments, the first diameter maybe greater than the second diameter. The first portion 1021 may be coupled to the bottom wall 1056 and extend upwardly therefrom. The second portion 1023 may extend from the first portion 1021 to form a shoulder 1072 where the first portion 1021 and the second portion 1023 join.

Figure 28A:
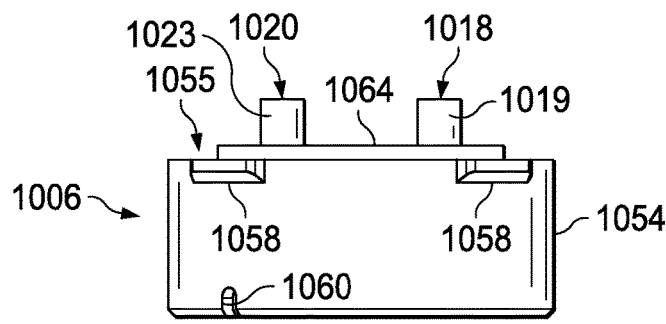
FIG. 28A is a side view of the disc cup of FIG. 27.

FIG. 28A is a side view of the disc cup 1006 illustrating additional details that may be associated with some embodiments. As shown, the first nipple 1018 and the second nipple 1020 may have a length greater than a length of the tubular wall 1054 and the inner wall 1064 so that at least a part of the second portion 1019 and the second portion 1023 may extend above the inner wall 1064.

Figure 28B:
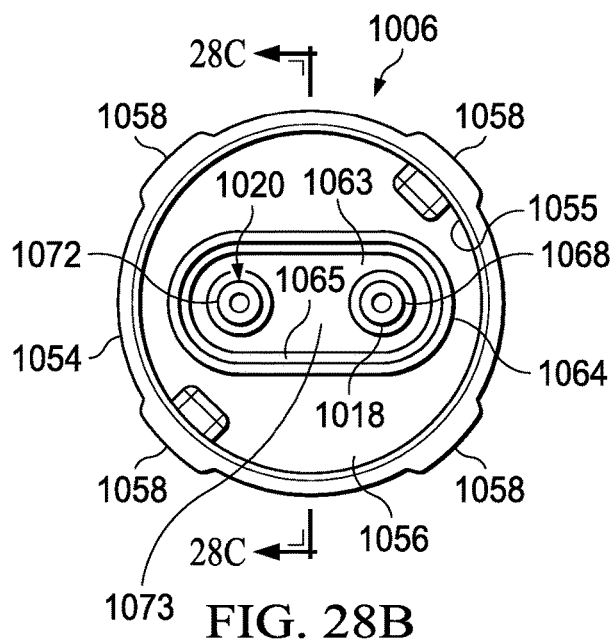
FIG. 28B is a top view of the disc cup of FIG. 27.

FIG. 28B is a top view of the disc cup 1006 illustrating additional details that may be associated with some embodiments. As shown, the inner wall 1064 may surround a center portion 1073 of the bottom wall 1056. The first nipple 1018 and the second nipple 1020 may be coupled to the bottom wall 1056 on opposite sides of the center portion 1073 of the bottom wall 1056. The inner wall 1064 may also surround the first nipple 1018 and the second nipple 1020.

Figure 28C:
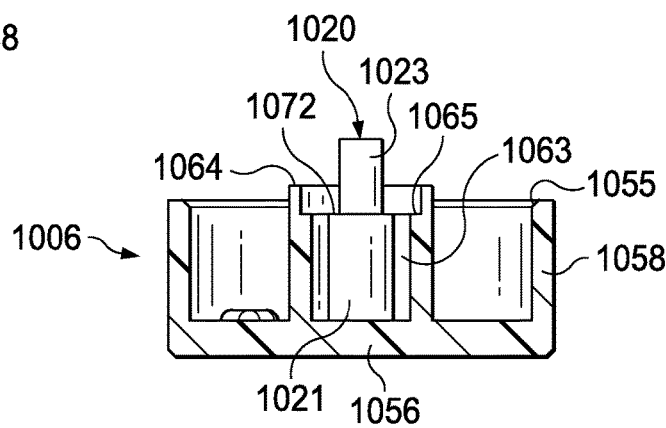
FIG. 28C is a cross-sectional view of the disc cup of FIG. 27 taken along line 28C-28C of FIG. 28B.

FIG. 28C is a cross-sectional view of the disc cup 1006 illustrating additional details that may be associated with some embodiments. As shown, the second nipple 1020 may be coupled to the bottom wall 1056 and be surrounded by the inner wall 1064. In some embodiments, the second nipple 1020 may not couple to or come into contact with the inner wall 1064. In some embodiments, there may be a region of open space between the second nipple 1020 and the inner wall 1064. The region of open space may also be referred to as a sensing bypass 1063.

FIG. 29A is a cross-sectional assembly view of a specimen container assembly 1100 that may be used with a collection fitting, for example the collection fitting 1000. The specimen container assembly 1100 may include a specimen container 1102 and a cap 1104. The specimen container 1102 may be a tubular member having a closed end formed by a bottom wall 1108. The specimen container 1102 may have an end opposite the bottom wall 1108 that may include a threaded portion 1110 on an exterior portion of the specimen container 1102.

The cap 1104 may be a tubular member having into an interior diameter surface and an open end having a thread 1112 formed on the interior diameter surface. The cap 1104 may have a first port 1116 and a second port 1118 opposite the open end. The first port 1116 and the second port 1118 may be disposed proximate to a center of the cap 1104. The first port 1116 may include an extension 1114 depending towards the open end of the cap 1104. The cap 1104 may have an annular wall 1120 surrounding the first port 1116 and the second port 1118. The annular wall 1120 may include tabs 1122 coupled to an upper exterior end of the annular wall 1120. The tabs 1122 may have a circumferential length less than a circumference of the annular wall 1120.

The cap 1104 may have a shoulder 1124 extending between the annular wall 1120 an exterior of the cap 1104.

FIG. 29B is a plan view of a dust cap 1106 that may be used with a specimen container, such as the specimen container assembly 1100. The dust cap 1106 may be an annular member dimension to fit around the annular wall 1120. The dust cap 1106 may have an annular wall 1130 and a dust flange 1128 coupled to the annular wall 1130. The annular wall 1130 may have recesses 1126 formed in the inner diameter. The recesses 1126 may have a dimension substantially similar to the dimensions of the tabs 1122 of the annular wall 1120. The dust cap 1106 may also include a topper 1132 having dimensions configured to fit over the opening open area of the dust cap 1106 and secure to and cover the first port 1116 and the second port 1118.

Figure 30:
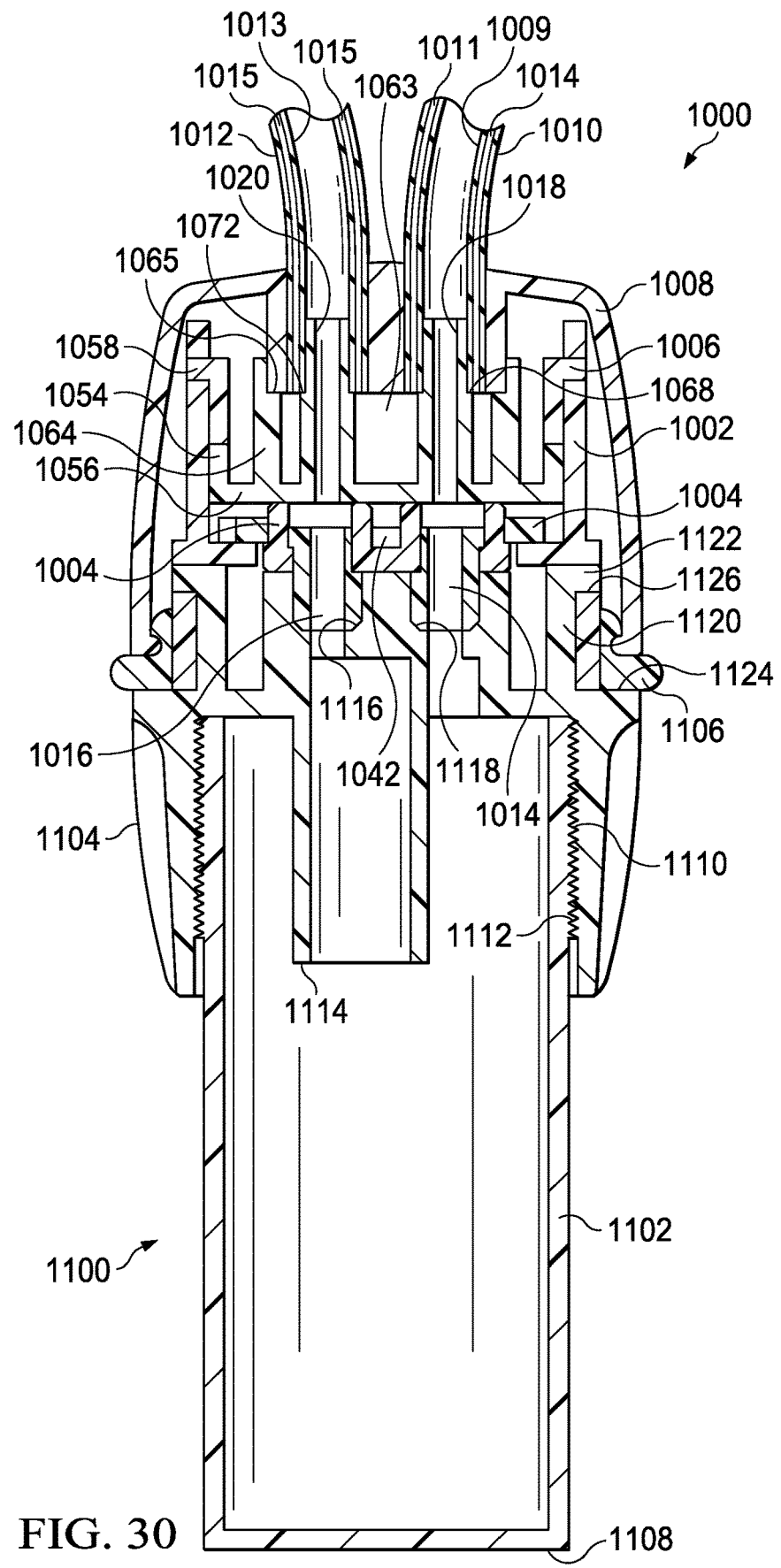
FIG. 30 is a cross-sectional view of the illustrative collection fitting of FIG. 23 assembled with the specimen container of FIG. 29A and the dust cap of FIG. 29B.

FIG. 30 is an assembled sectional view of the specimen container assembly 1100 and the collection fitting 1000 illustrating additional details that may be associated with some embodiments. The specimen container 1102 may be threaded into the cap 1104 through the mating threads 1110 and 1112. The dust cap 1106 may be fitted over the cap 1104 so that the dust flange 1128 rests on the shoulder 1124. To accomplish this the tabs 1122 may be inserted through the recesses 1126 of the dust flange 1128. The dust cap 1106 may then be rotated relative to the cap 1104 to secure the dust cap 1106 to the cap 1104.

To assemble the collection fitting 1000, the switch 1004 may be inserted into the chassis 1002 so that the shoulder 1052 may rest on the shoulder 1038. In some embodiments, the cut-out 1046 of the flange 1044 of the switch 1004 may be aligned with the key 1033 of the chassis 1002. In some embodiments, if the switch 1004 is disposed in the chassis 1002, the key 1033 may be positioned between the opposing shoulders 1043, 1045.

The disc cup 1006 may be inserted into the chassis 1002 after the switch 1004 so that the bottom wall 1056 may rest on the switch 1004. In some embodiments, an upper portion of the key 1033 may be inserted into the notch 1060 of the chassis 1002, preventing rotation of the disc cup 1006 relative to the chassis 1002. The protrusions 1058 may be inserted into the apertures 1034, securing the disc cup 1006 to the chassis 1002. The cap 1008 may be fitted over the chassis 1002 so that the first passage 1022 may rest on the shoulder 1065 of the annular inner wall 1064 of the disc cup 1006. Similarly, the second passage 1024 may also rest on the shoulder 1065 of the annular inner wall 1064 of the disc cup 1006. The first passage 1022 and the second passage 1024 may seal to the shoulder 1065 so that the first passage 1022 and the second passage 1024 may be fluidly isolated from the interior of the cap 1008 and portions of the disc cup 1006 between the tubular wall 1054 and the annular inner wall 1064.

The first tube 1010 may be a multi-lumen conduit having a central lumen 1009 and one or more peripheral lumens 1011. The first tube 1010 may be inserted into the first passage 1022 so that the first nipple 1018 may insert into the central lumen 1009, thereby placing the central lumen 1009 of the first tube 1010 into fluid communication with the first nipple 1018. An end of the first tube 1010 may be in contact with the shoulder 1068, so that an end of the first tube 1010 may be separated from the bottom wall 1056 of the disc cup 1006. Separation of the end of the first tube 1010 from the bottom wall 1056 places the peripheral lumens 1011 into fluid communication with the sensing bypass 1063 between the annular inner wall 1064, the first nipple 1018, and the second nipple 1020.

Similarly, the second tube 1012 may be a multi-lumen conduit having a central lumen 1013 and one or more peripheral lumens 1015. The second tube 1012 may be inserted into the second passage 1024 so that the second nipple 1020 may insert into the central lumen 1013, thereby placing the central lumen 1013 of the second tube 1012 into fluid communication with the second nipple 1020. An end of the second tube 1012 may be in contact with the shoulder 1072, so that an end of the second tube 1012 may be separated from the bottom wall 1056 of the disc cup 1006. Separation of the end of the second tube 1012 from the bottom wall 1056 places the peripheral lumen 1015 into fluid communication with the sensing bypass 1063 between the annular inner wall 1064, the second nipple 1020, and the first nipple 1018. Fluid communication between the peripheral lumens 1011 and the peripheral lumens 1015 may occur through the sensing bypass 1063.

The specimen container assembly 1100 may be inserted into the chassis 1002. A lower end of the cap 1008 may have a detent configured to engage a mating detent on the dust cap 1106, securing the specimen container assembly 1100 to the collection fitting 1000. As shown, the first port 1014 of the switch 1004 may be inserted into the second port 1118 of the cap 1104. Similarly, the second port 1016 of the switch 1004 may be inserted into the first port 1116 of the cap 1104. The insertion may permit rotation of the specimen container assembly 1100 to cause a corresponding rotation of the switch 1004.

In some embodiments, the switch 1004 may be disposed within the chassis 1002 so that the shoulder 1043 of the cut-out 1046 may be in contact with the key 1033. If the key 1033 is in contact with the shoulder 1043 of the cut-out 1046, the switch 1004 may be in a bypass position where the bypass passage 1042 may be in fluid communication with the first nipple 1018 and the second nipple 1020. If the specimen container assembly 1100 is inserted into the collection fitting 1000 and rotated, for example, with a rotation of about 90 degrees, the specimen container assembly 1100 may cause the switch 1004 to rotate about 90 degrees. The 90 degree rotation may cause the switch 1004 to rotate relative to the chassis 1002 so that the key 1033 may be positioned proximate to or adjacent to the shoulder 1045. If the key 1033 is proximate to the shoulder 1045, the switch 1004 may be in a sampling position as shown in FIG. 30. In the sampling position, the first nipple 1018 may be in fluid communication with the first port 1014 and the second nipple 1020 may be in fluid communication with the second port 1016, permitting fluid communication through the switch 1004 into the specimen container 1102. In this manner, the collection fitting 1000 and the specimen container assembly 1100 may permit sampling of fluids while providing reduced-pressure therapy.

In some embodiments, if the specimen container assembly 1100 is coupled to the collection fitting 1000, the tabs 1122 may be inserted into the mounting slots 1032. The tabs 1122 may be moved through the axial portion 1035 of the mounting slots 1032 until the tabs 1122 reach the end of the axial portion 1035 of the mounting slots 1032 adjacent to the circumferential portion 1037. If the specimen container 1102 is rotated to cause rotation of the switch 1004, the tabs 1122 may move circumferentially through the circumferential portion 1037 of the mounting slots 1032. If the tabs 1122 reach the end of the circumferential portion 1037 of the mounting slots 1032, the tabs 1122 may limit further rotation of the specimen container 1102. In some embodiments, the circumferential portion 1037 of the mounting slots 1032, the size of the tabs 1122, the placement of the key 1033, and the length of the cut-out 1046 may be selected to align the first port 1014 with the first nipple 1018 and the second port 1016 with the second nipple 1020 if the tabs 1122 reach an end of the circumferential portion 1037 of the mounting slots 1032. In addition, the tabs 1122 may be fully within the circumferential portion 1037 of the mounting slots 1032, and thereby prevented from axial motion relative to the collection fitting 1000.

Plunger Switch

Figure 31:
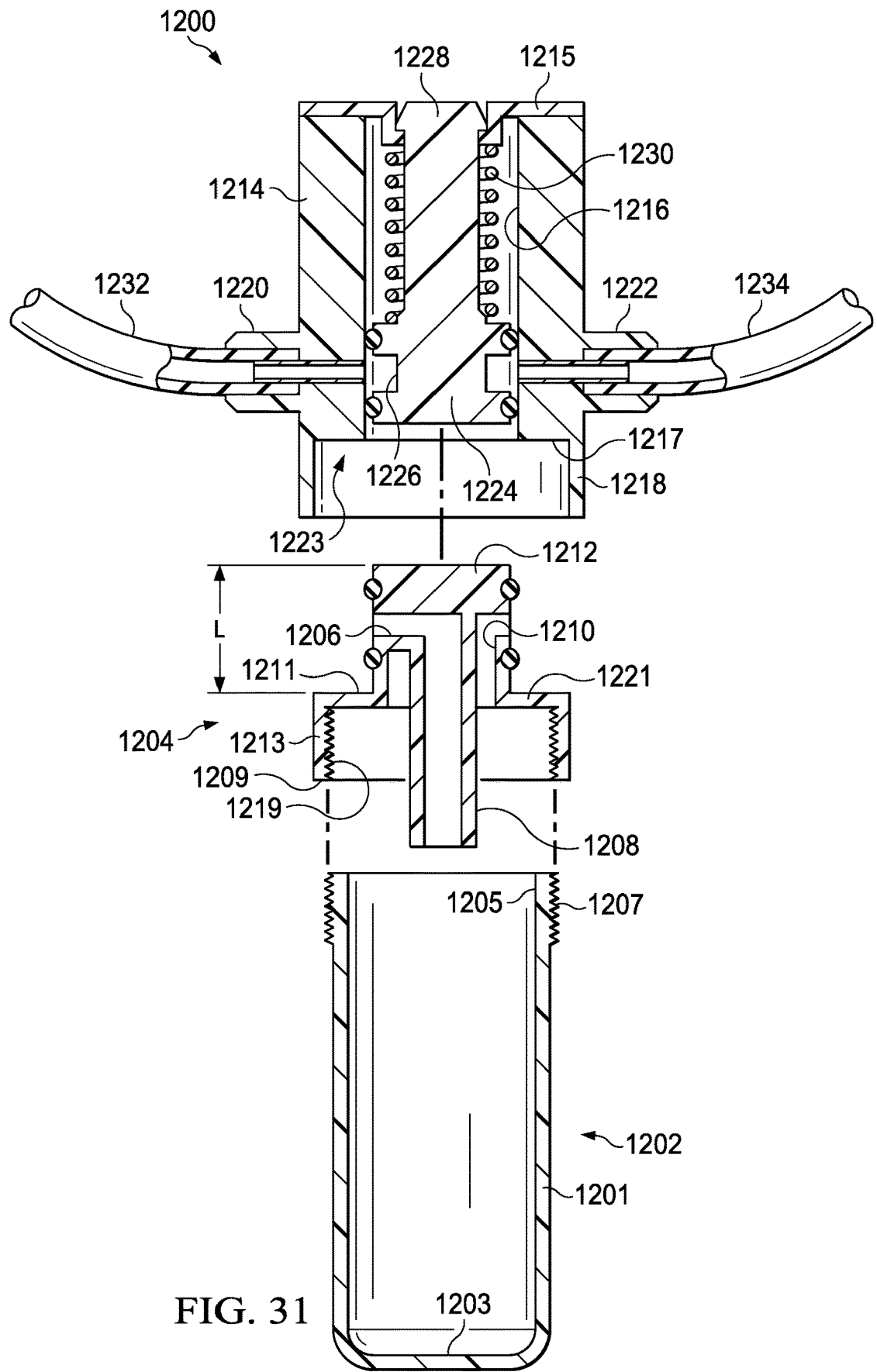
FIG. 31 is an exploded cross-sectional view of another example embodiment of a collection fitting and specimen container that may be associated with some embodiments of the reduced-pressure therapy system of FIG. 1 in accordance with this specification.

FIG. 31 is a sectional view of a collection fitting 1200 that may be used with a reduced-pressure therapy system, such as the reduced-pressure therapy system 100, for example. The collection fitting 1200 may be an example embodiment of the collection fitting 106. The collection fitting 1200 may include a specimen container 1202, such as a vial, or a graduated cylinder, for example. The specimen container 1202 may be a tubular member having a closed end 1203 and an open end 1205 opposite the closed end. In some embodiments, a portion of a tubular wall 1201 of the specimen container 1202 extending toward the closed end 1203 of the specimen container 1202 may have a thread 1207 on an outer diameter surface of the specimen container 1202. The thread 1207 may extend a portion of a distance of the tubular wall 1201 between the open end 1205 and the closed end 1203 of the specimen container 1202 from a location proximate to the open end 1205. In some embodiments, the thread 1207 may extend from a location adjacent to the open end 1205.

The collection fitting 1200 may also include a cap 1204. The cap 1204 may have a closed end 1211 and an open end 1209. The open end 1209 of the cap 1204 may have a tubular wall 1213 having an inner diameter surface. In some embodiments, a diameter of the inner diameter surface may be dimensioned to receive the open end 1205 of the specimen container 1202. In some embodiments, the open end 1209 of the cap 1204 may have a thread 1219 formed on the inner diameter surface of the open end 1209. In some embodiments, the thread 1219 on the inner diameter surface of the cap 1204 may be configured to mate with the thread 1207 on the outer diameter surface of the specimen container 1202.

In some embodiments, the closed end 1211 of the cap 1204 may have an annular wall 1221 extending radially inward from an end of the tubular wall 1213 opposite of the open end 1209. The annular wall 1221 may extend a portion of the distance between the tubular wall 1213 and a center of the cap 1204.

The cap 1204 may have a boss 1212 coupled to radially interior ends of the annular wall 1221 and extending away from the open end 1209 of the cap 1204 parallel to an axis of the cap 1204. The boss 1212 may have a length L between the annular wall 1221 and an end of the boss 1212. A first inlet 1206 and a second inlet 1210 may be formed in the boss 1212. Both the first inlet 1206 and the second inlet 1210 may be fluid passages through the boss 1212 into the open end 1209 of the cap 1204. In some embodiments, both the first inlet 1206 and the second inlet 1210 may have openings in a sidewall of the boss 1212. In some embodiments, the openings of the first inlet 1206 and the second inlet 1210 may be opposite one another. In other embodiments, the openings of the first inlet 1206 and the second inlet 1210 may be adjacent to or proximate to one another. In some embodiments, both the first inlet 1206 and the second inlet 1210 may extend horizontally from a side of the boss 1212 to an elbow. Both the first inlet 1206 and the second inlet 1210 may have openings proximate to the open end 1209 of the cap 1204 that may face a same direction. In some embodiments, the openings into the open end of the cap 1204 of the first inlet 1206 and the second inlet 1210 may be perpendicular to the openings of the first inlet 1206 and the second inlet 1210 into the boss 1212.

In some embodiments, the first inlet 1206 may have a baffle 1208. The baffle 1208 may be a tubular body depending from the boss 1212 toward the open end 1209 of the cap 1204. In some embodiments, the baffle 1208 may have a length such that an end of the baffle 1208 depends below the open end 1209 of the cap 1204. In other embodiments, the baffle 1208 may be a planar wall and may have a length such that an end of the baffle 1208 does not depend below the open end 1209 of the cap 1204. In other embodiments, the baffle 1208 may be positioned between the openings of the first inlet 1206 and the second inlet 1210 facing the open end of the cap 1204.

The collection fitting 1200 may include a housing 1214. In some embodiments, the housing 1214 may be a tubular body. The housing 1214 may have an open end 1223 and a closed end opposite the open end 1223 formed by a wall 1215 having peripheral portions coupled to the tubular body of the housing 1214. The housing 1214 may have a central passage 1216 extending from the open end 1223 of the tubular body to the wall 1215. In some embodiments, the housing 1214 may have an annular wall 1218 depending from the open end 1223 of the housing 1214. The annular wall 1218 may have an inner diameter that is greater than a diameter of the central passage 1216 so that a shoulder 1217 is formed between the annular wall 1218 and the central passage 1216. In some embodiments, the diameter of the inner diameter of the annular wall 1218 may be substantially equal to a diameter of an outer diameter of the open end 1209 of the cap 1204.

The housing 1214 may also include a first union 1220 and a second union 1222. The first union 1220 and the second union 1222 may extend through the tubular body of the housing 1214. In some embodiments, the first union 1220 and the second union 1222 may be positioned on an exterior surface of the housing 1214 proximate to the open end 1223 of the housing 1214. In some embodiments, the first union 1220 and the second union 1222 may be adjacent to the open end 1223 of the housing 1214. The first union 1220 and the second union 1222 may provide a location for fluid coupling of an external device to the housing 1214. Both the first union 1220 and the second union 1222 may include a passage extending into the central passage 1216 of the housing 1214. In some embodiments, the first union 1220 and the second union 1222 may be ports.

A plunger 1224 may be disposed in the central passage 1216 of the housing 1214. The plunger 1224 may be a cylindrical body having a diameter to slidingly engage the central passage 1216. In some embodiments, the plunger 1224 may be configured to fluidly seal to the central passage 1216, preventing fluid communication through the central passage 1216 across the plunger 1224. In some embodiments, the plunger 1224 may have a bypass passage 1226 disposed in the plunger 1224. The bypass passage 1226 may be an annular recess disposed proximate to a center of the plunger 1224. The plunger 1224 may fluidly seal to the central passage 1216 axially above the bypass passage 1226 and axially below the bypass passage 1226. In other embodiments, the bypass passage 1226 may extend through a center of the plunger 1224. The plunger 1224 may be configured to move axially through the central passage 1216 so that the plunger 1224 may variably align the bypass passage 1226 with the first union 1220 and the second union 1222 in a bypass position as shown in FIG. 31.

A stem 1228 may be coupled to the plunger 1224 and extend axially upward from the plunger 1224 through the central passage 1216. The stem 1228 may be a cylindrical body extending from an upper surface of the plunger 1224 toward the wall 1215 of the housing 1214. In some embodiments, the stem 1228 may have an end opposite the plunger 1224 disposed in an opening of the wall 1215 so that the stem 1228 may move axially relative to the wall 1215. A spring 1230 may circumscribe the stem 1228 and have a first end resting on the plunger 1224 and a second end engaged with the wall 1215 of the housing 1214. The spring 1230 may be configured to be compressed between the plunger 1224 and the wall 1215, biasing the plunger 1224 to the bypass position.

A first tube 1232 may be fluidly coupled to the first union 1220. The first tube 1232 may have a single lumen configured to be in fluid communication with the first union 1220. In other embodiments, the first tube 1232 may be a multi-lumen conduit having a central lumen and one or more peripheral lumens. The first tube 1232 may be further coupled to a canister, reduced-pressure source, or other device. A second tube 1234 may be fluidly coupled to the second union 1222. The second tube 1234 may have a single lumen configured to be in fluid communication with the second union 1222. In other embodiments, the second tube 1234 may be a multi-lumen conduit having a central lumen and one or more peripheral lumens. The second tube 1234 may be further coupled to a dressing or other device.

Figure 32A:
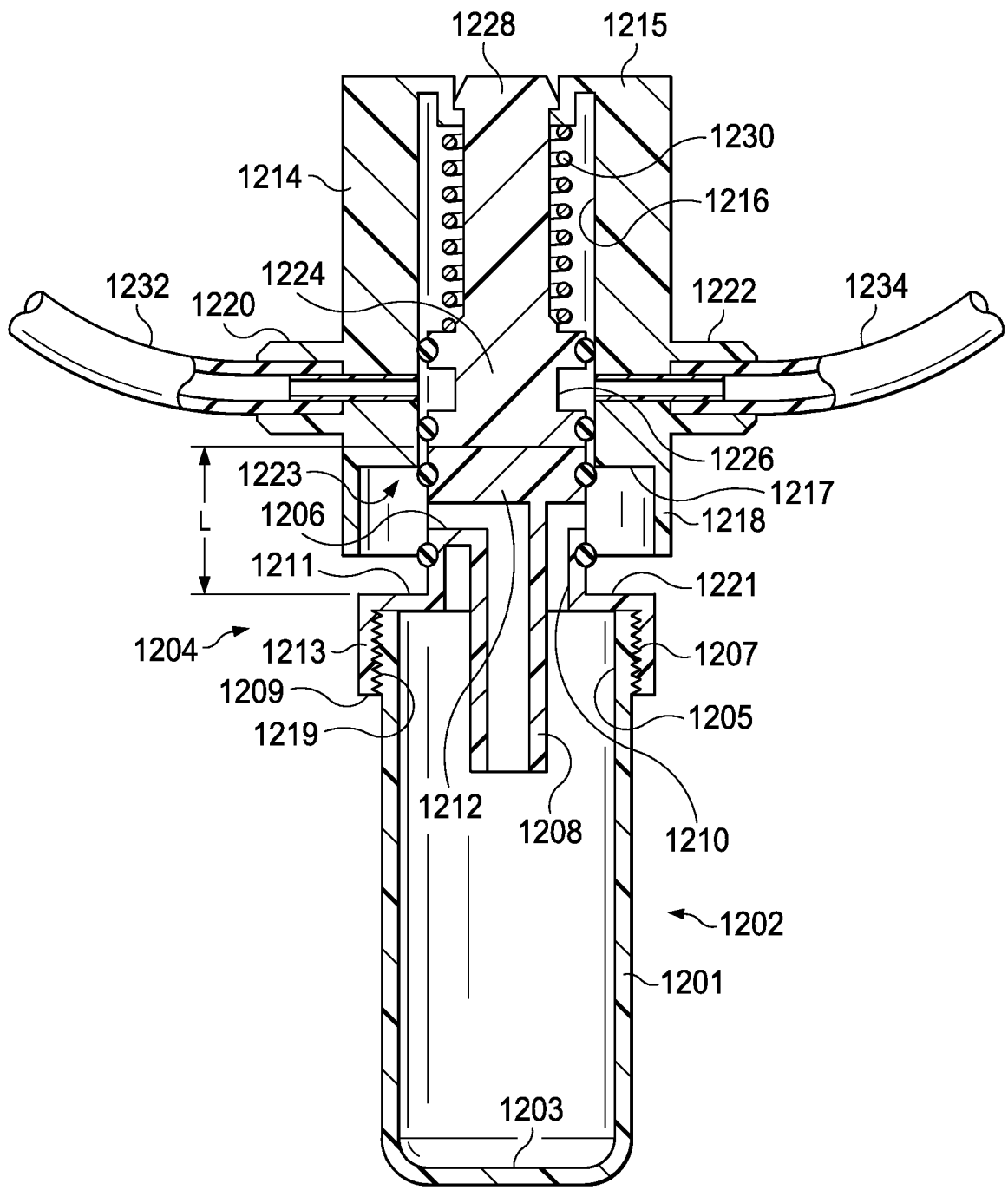
FIG. 32A and FIG. 32B are cross-sectional views illustrating the use of the illustrative collection fitting and specimen container of FIG. 31.

FIG. 32A is a sectional view of the collection fitting 1200 illustrating additional details that may be associated with some embodiments. In some embodiments, the cap 1204 may be secured to the specimen container 1202 so that the specimen container 1202 and the cap 1204 may be manipulated as a single body. The plunger 1224 may be in the bypass position. In the bypass position, the spring 1230 may be in a relaxed position, or a slightly compressed position. The stem 1228 may not substantially protrude beyond the wall 1215 if the plunger 1224 is in the bypass position. In the bypass position, the bypass passage 1226 may be in fluid communication with the first union 1220 and the second union 1222. The first tube 1232 may be coupled to the first union 1220 and further coupled to a canister or reduced-pressure source. The second tube 1234 may be coupled to the second union 1222 and further coupled to a dressing, which may be coupled to a tissue site. The first tube 1232 may be in fluid communication with the first union 1220, and the second tube 1234 may be in fluid communication with the second union 1222.

Operation of the reduced-pressure source may cause fluid flow between the dressing and the reduced-pressure source through the collection fitting 1200. The fluid flow may occur through the first tube 1232, the first union 1220, the bypass passage 1226, the second union 1222, and the second tube 1234. The fluid flow may provide a reduced pressure at the dressing and may cause fluids, including liquids from the tissue site, to move from the dressing through the collection fitting 1200 into a fluid collection apparatus, such as the specimen container 1202 fluidly coupled between the collection fitting 1200 and the reduced-pressure source.

If a sample of fluid from the tissue site is desired, the specimen container 1202 and the cap 1204 may be brought proximate to the housing 1214. In some embodiments, the boss 1212 may be aligned with and placed in contact with the plunger 1224. As shown in FIG. 32A, the boss 1212 may be dimensioned to sealing engage the central passage 1216.

Figure 32B:
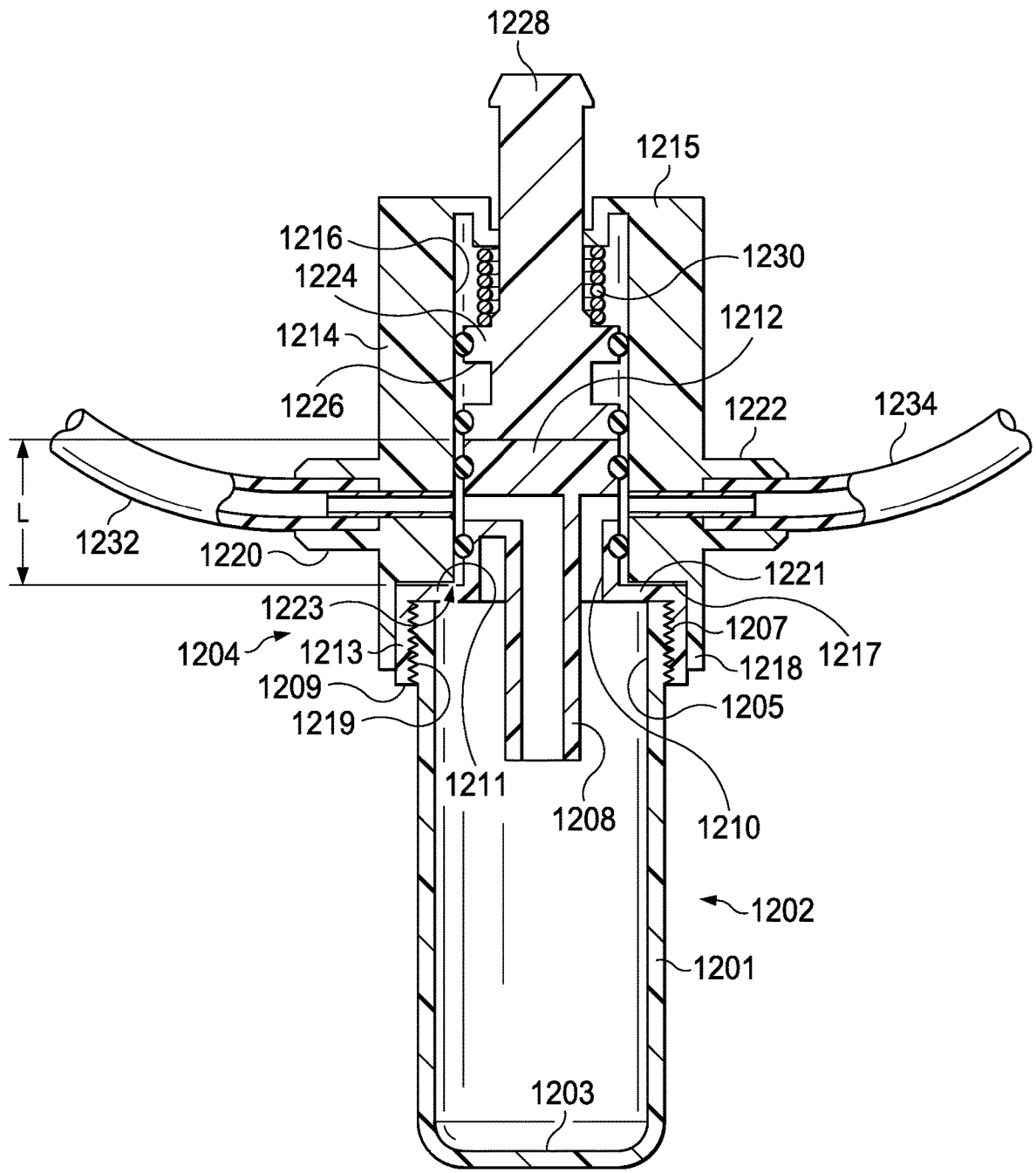

FIG. 32B is a sectional view illustrating additional details of the use of the collection fitting 1200. Here, the boss 1212 may be inserted into the central passage 1216 of the housing 1214. The insertion of the boss 1212 into the central passage 1216 may cause the plunger 1224 to move axially upward, compressing the spring 1230. Movement of the plunger 1224 axially upward may move the bypass passage 1226 out of fluid communication with the first union 1220 and the second port 1220.

The boss 1212 may be inserted into the central passage 1216 until the closed end 1203 of the cap 1204 may contact the shoulder 1217 of the housing 1214 adjacent to the annular wall 1218. The insertion may place the cap 1204 within a space bounded by the annular wall 1218. In addition, the length L of the boss 1212 may extend into the central passage 1216, moving the plunger 1224 a distance substantially equal to L into the central passage 1216. The movement of the plunger 1224 into the central passage 1216 may also compress the spring 1230 a distance substantially equal to L and move an end of the stem 1228 beyond the wall 1215. The positioning of the end of the stem 1228 beyond the wall 1215 may indicate that the collection fitting 1200 is in a sampling position.

If in the sampling position of FIG. 32B, the first inlet 1206 of the cap 1204 may be positioned proximate to the first union 1220. In some embodiments, the first inlet 1206 may be in fluid communication with the first union 1220. Similarly, the second inlet 1210 may be in fluid communication with the second union 1222. In the sampling position, fluid communication may occur between the first tube 1232 and the second tube 1234 through the first union 1220, the first inlet 1206, the specimen container 1202, the second inlet 1210, and the second union 1222.

Operation of the reduced-pressure source may continue while the boss 1212 is inserted into the central passage 1216. If the boss 1212 is inserted into the central passage 1216, the boss 1212 may fluidly seal to the central passage 1216 around the first inlet 1206 and the second inlet 1210. The reduced-pressure source may supply reduced pressure to the dressing and the tissue site through the collection fitting 1200 and the specimen container 1202. As fluids, including liquids from the tissue site, are drawn through the second tube 1234 by the reduced pressure, the fluids may flow into the specimen container 1202 through the second inlet 1210. The baffle 1208 may prevent liquids from flowing directly between the second inlet 1210 and the first inlet 1206. The specimen container 1202 and the cap 1204 may be left in the sampling position of FIG. 32B until the specimen container 1202 contains a desired amount of fluids from the tissue site.

If the specimen container 1202 is full, or a sufficient sample has been received, the specimen container 1202 may be removed from the housing 1214. The compression of the spring 1230 the distance L may cause the spring 1230 to exert a counteracting force that is proportional to the spring force of the spring 1230 and the distance L. The counteracting force may urge the plunger 1224 to return to the bypass position as shown in some embodiments of FIG. 32A. If the plunger 1224 returns to the bypass position of FIG. 32A, the bypass passage 1226 may again be in fluid communication with the first union 1220 and the second union 1222. In this manner, reduced-pressure therapy may be supplied without significant interruption during the sampling process.

The systems and methods described herein may provide significant advantages, some of which have already been mentioned. For example, the reduced-pressure therapy system 100 provides a mechanism by which to sample fluid or liquid from a tissue site. The reduced-pressure therapy system 100 also provides a sampling mechanism to allow for sampling of fluids in a discrete time. Further, the reduced-pressure therapy system 100 prevents potential contamination of wound fluid with moisture-reducing substances in a fluid collection apparatus. In addition, the reduced-pressure therapy system 100 provides a mechanism to sample fluid while still providing feedback pressure to a therapy unit. Still further, the reduced-pressure therapy system 100 may provide a sampling mechanism that allows for fluid sampling without risking a leak or discontinuing reduce pressure therapy.

It should be apparent from the foregoing that an invention having significant advantages has been provided. While shown in only a few forms, the systems and methods illustrated are susceptible to various changes and modifications without departing from the spirit thereof.

I claim:

1. A collection fitting for sampling a fluid from a tissue site, the collection fitting comprising:
    a tee-fitting having a first arm, a second arm, and a third arm, a first lumen extending through the tee-fitting from the first arm to the second arm, a second lumen extending through the tee-fitting from the first arm to the third arm, and a third lumen extending through the tee-fitting from the second arm to the third arm, wherein the first lumen is an independent fluid path from the second lumen and the third lumen, and wherein the first lumen is configured to be unaffected by sampling the fluid from the tissue site; and
    a container union coupled to the third arm.

2. The collection fitting of claim 1, wherein the first lumen extending through the tee-fitting from the first arm to the second arm is a pressure sensing lumen.

3. The collection fitting of claim 1, wherein the container union comprises a valve configured to be fluidly coupled to a specimen container.

4. The collection fitting of claim 1, wherein the container union comprises a valve, the valve comprising:
    a valve housing having a first end, a second end, and a passage, the first end coupled to the third arm so that the passage is in fluid communication with the second and third lumens in the third arm; and
    a flap coupled to the second end of the valve housing and configured to selectively permit fluid communication through the second end.

5. The collection fitting of claim 4, wherein the flap is biased to prevent fluid communication through the second end.

6. The collection fitting of claim 4, wherein the flap is coupled to a biasing member configured to bias the flap to a closed position, and further comprising an actuator having at least one rod configured to engage the flap to move the flap to an open position, the actuator configured to be coupled to a specimen container.

7. The collection fitting of claim 1, wherein the container union comprises a valve configured to be fluidly coupled to a specimen container, the valve comprising:
    a valve housing having a passage;
    a wall disposed in the passage;
    at least two flaps coupled to the valve housing, each flap configured to selectively block a portion of the passage between the valve housing and the wall;
    at least two biasing members, each coupled to a respective flap and the valve housing to bias the respective flap to a closed position; and
    an actuator having at least two rods coupled to an end of the actuator and positioned to engage a respective flap to move the respective flap to an open position.

8. The collection fitting of claim 1, wherein the container union comprises a valve configured to be fluidly coupled to a specimen container, the valve comprising:
a valve housing;
a valve member disposed within the valve housing; and
a biasing member disposed within the valve housing between the valve member and an end of the valve housing, the biasing member configured to urge the valve member into sealing engagement with the valve housing.

9. The collection fitting of claim 8, further comprising an actuator configured to be coupled to the specimen container, the actuator comprising:
an actuator housing having a protrusion extending from an end of the actuator housing, the actuator housing configured to engage the valve housing; and
wherein the protrusion is configured to be inserted into the valve housing to contact the valve member and move the valve member out of sealing engagement with the valve housing.

10. The collection fitting of claim 9, wherein the valve member is spherical.

11. The collection fitting of claim 9, wherein the valve member is conical.

12. The collection fitting of claim 1, wherein the second lumen extending through the tee-fitting between the first arm and the third arm and the third lumen extending through the tee-fitting between the second arm and the third arm each have a 90 degree elbow.

13. The collection fitting of claim 1, wherein the tee-fitting comprises a triangular body.

14. The collection fitting of claim 13, wherein the second lumen extending through the tee-fitting between the first arm and the third arm and the third lumen extending through the tee-fitting between the second arm and the third arm form an angle of about 30 degrees with the first lumen extending through the tee-fitting between the first arm and the second arm.

15. A system for sampling a fluid from a tissue site, the system comprising:
a collection fitting comprising:
a tee-fitting having a first arm having a first union, a second arm having a second union, and a third arm, a first lumen extending through the tee-fitting from the first arm to the second arm, a second lumen extending through the tee-fitting from the first arm to the third arm, and a third lumen extending through the tee-fitting from the second arm to the third arm, wherein the first lumen is an independent fluid path from the second lumen and the third lumen; and
a container union coupled to the third arm,
a reduced-pressure source configured to be fluidly coupled to the first union; and
a specimen container configured to be coupled to the container union;
wherein the first lumen is configured to be unaffected by sampling with the specimen container.

16. The system of claim 15, further comprising a multi-lumen tube fluidly coupling the first union to the reduced-pressure source and a multi-lumen tube fluidly coupling the second union to the tissue site.

17. The system of claim 15, further comprising:
a dressing configured to be coupled to the tissue site; and
a storage container fluidly coupled between the reduced-pressure source and the collection fitting.

18. The system of claim 15, wherein the first lumen extending through the tee-fitting from the first arm to the second arm is a pressure sensing lumen.

19. The system of claim 15, wherein the container union comprises a valve configured to be fluidly coupled to the specimen container.

20. The system of claim 15, wherein the container union comprises a valve, the valve comprising:
a valve housing having a first end, a second end, and a passage, the first end coupled to the third arm so that the passage is in fluid communication with the second and third lumens in the third arm; and
a flap coupled to the second end of the valve housing and configured to selectively permit fluid communication through the second end.

21. The system of claim 20, wherein the flap is biased to prevent fluid communication through the second end.

22. The system of claim 20, wherein the flap is coupled to a biasing member configured to bias the flap to a closed position, and further comprising an actuator having at least one rod configured to engage the flap to move the flap to an open position, the actuator configured to be coupled to the specimen container.

23. The system of claim 15, wherein the container union comprises a valve configured to be fluidly coupled to the specimen container, the valve comprising:
a valve housing having a passage;
a wall disposed in the passage;
at least two flaps coupled to the valve housing, each flap configured to selectively block a portion of the passage between the valve housing and the wall;
at least two biasing members, each coupled to a respective flap and the valve housing to bias the respective flap to a closed position; and
an actuator having at least two rods coupled to an end of the actuator and positioned to engage a respective flap to move the respective flap to an open position.

24. The system of claim 15, wherein the container union comprises a valve configured to be fluidly coupled to the specimen container, the valve comprising:
a valve housing;
a valve member disposed within the valve housing; and
a biasing member disposed within the valve housing between the valve member and an end of the valve housing, the biasing member configured to urge the valve member into sealing engagement with the valve housing.

25. The system of claim 24, further comprising an actuator configured to be coupled to the specimen container, the actuator comprising:
an actuator housing having a protrusion extending from an end of the actuator housing, the actuator housing configured to engage the valve housing; and
wherein the protrusion is configured to be inserted into the valve housing to contact the valve member and move the valve member out of sealing engagement with the valve housing.

26. The system of claim 25, wherein the valve member is spherical.

27. The system of claim 25, wherein the valve member is conical.

28. The system of claim 15, wherein the second lumen extending through the tee-fitting between the first arm and the third arm and the third lumen extending through the tee-fitting between the second arm and the third arm each have a 90 degree elbow.

29. The system of claim 15, wherein the tee-fitting comprises a triangular body.

30. The system of claim 29, wherein the second lumen extending through the tee-fitting between the first arm and the third arm and the third lumen extending through the tee-fitting between the second arm and the third arm form an angle of about 30 degrees with the first lumen extending through the tee-fitting between the first arm and the second arm.

\* \* \* \* \*

UNITED STATES PATENT AND TRADEMARK OFFICE
CERTIFICATE OF CORRECTION

PATENT NO. : 10,667,735 B2
APPLICATION NO. : 14/488498
DATED : June 2, 2020
INVENTOR(S) : Christopher Brian Locke It is certified that error appears in the above-identified patent and that said Letters Patent is hereby corrected as shown below:

On the Title Page

On Page 3, Column 2, item (56) under (Other Publications)
Line 50, delete "Hypermia" and insert -- Hyperemia --, therefor.

In the Specification

Column 8
Line 4, delete "hydroxy apatites," and insert -- hydroxyapatites, --, therefor.

Column 36
Line 52, after "In" delete "the".

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*